US008337834B2

(12) United States Patent
Fraser et al.

(10) Patent No.: US 8,337,834 B2
(45) Date of Patent: *Dec. 25, 2012

(54) METHODS OF MAKING ENHANCED, AUTOLOGOUS FAT GRAFTS

(75) Inventors: John K. Fraser, San Diego, CA (US); Marc H. Hedrick, Encinitas, CA (US)

(73) Assignee: Cytori Therapeutics, Inc., San Diego, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 13/042,334

(22) Filed: Mar. 7, 2011

(65) Prior Publication Data

US 2011/0158968 A1 Jun. 30, 2011

Related U.S. Application Data

(60) Continuation of application No. 12/886,353, filed on Sep. 20, 2010, now Pat. No. 7,901,672, which is a continuation of application No. 10/614,648, filed on Jul. 7, 2003, now Pat. No. 8,119,121, which is a division of application No. 10/316,127, filed on Dec. 9, 2002, now abandoned.

(51) Int. Cl.
 *C12N 5/00* (2006.01)
(52) U.S. Cl. ........... 424/93.7; 435/366; 435/325; 606/1; 606/131; 604/19; 604/22
(58) Field of Classification Search ........................ None
See application file for complete search history.

(56) References Cited

U.S. PATENT DOCUMENTS

| | | |
|---|---|---|
| 4,000,275 A | 12/1976 | Lunn |
| 4,418,691 A | 12/1983 | Yannas et al. |
| 4,458,678 A | 7/1984 | Yannas et al. |
| 4,734,269 A | 3/1988 | Clarke et al. |
| 4,820,626 A | 4/1989 | Williams et al. |
| 4,834,703 A | 5/1989 | Dubrul et al. |
| 4,883,755 A | 11/1989 | Carabasi et al. |
| 4,897,185 A | 1/1990 | Schuyler et al. |
| 4,963,489 A | 10/1990 | Naughton et al. |
| 5,035,708 A | 7/1991 | Alchas et al. |
| 5,079,160 A | 1/1992 | Lacy et al. |
| 5,092,883 A | 3/1992 | Eppley et al. |
| 5,143,063 A | 9/1992 | Fellner |
| 5,158,867 A | 10/1992 | McNally et al. |
| 5,226,914 A | 7/1993 | Caplan et al. |
| 5,261,612 A | 11/1993 | Ftaiha |
| 5,312,380 A | 5/1994 | Alchas et al. |
| 5,372,945 A | 12/1994 | Alchas et al. |
| 5,409,833 A | 4/1995 | Hu et al. |
| 5,436,135 A | 7/1995 | Tayot et al. |
| 5,470,307 A | 11/1995 | Lindall |
| 5,486,359 A | 1/1996 | Caplan et al. |
| 5,591,625 A | 1/1997 | Gerson et al. |
| 5,654,186 A | 8/1997 | Cerami et al. |
| 5,686,262 A | 11/1997 | Fink et al. |
| 5,686,289 A | 11/1997 | Humes et al. |
| 5,688,531 A | 11/1997 | Benayahu |
| 5,728,739 A | 3/1998 | Ailhaud et al. |
| 5,736,396 A | 4/1998 | Bruder et al. |
| 5,744,360 A | 4/1998 | Hu et al. |
| 5,783,408 A | 7/1998 | Hamilton et al. |
| 5,786,207 A | 7/1998 | Katz et al. |
| 5,811,094 A | 9/1998 | Caplan et al. |
| 5,817,050 A | 10/1998 | Klein |
| 5,827,735 A | 10/1998 | Young et al. |
| 5,827,740 A | 10/1998 | Pittenger |
| 5,827,897 A | 10/1998 | Ailhaud et al. |
| 5,837,235 A | 11/1998 | Mueller et al. |
| 5,837,444 A | 11/1998 | Shah |
| 5,837,539 A | 11/1998 | Caplan et al. |
| 5,851,832 A | 12/1998 | Weiss et al. |
| 5,854,292 A | 12/1998 | Ailhaud et al. |
| 5,869,037 A | 2/1999 | Crystal et al. |
| 5,906,934 A | 5/1999 | Grande et al. |
| 5,908,784 A | 6/1999 | Johnstone et al. |
| 5,916,743 A | 6/1999 | Lake et al. |
| 5,952,215 A | 9/1999 | Dwulet et al. |
| 5,968,356 A | 10/1999 | Morsiani |

(Continued)

FOREIGN PATENT DOCUMENTS

EP 0 418 979 3/1991
(Continued)

OTHER PUBLICATIONS

Angele, P. et al., "Engineering of Osteochondral Tissue with Bone Marrow Mesenchymal Progenitor Cells in a Derivatized Hyaluronan-Celatin Composite Sponge," *Tissue Engineering*, 1999, 5:545-53.

Ankrom, Michael A., "Age-related changes in human oestrogen receptor function and levels in osteoblasts," *Biochem J.* 333:787-794.

Athanasopoulos, T., Fabb, S., and Dickson, G. (2000) "Gene therapy vectors based on adeno-associated virus: characteristics and applications to acquired and inherited diseases (review)" Int J Mol Med 6, 363-75.

ATTC Preservation Methods: Freezing and Free-Drying, ATCC, 2nd Edition, 1991.

Avital, I., D. Inderbitzin, et al. (2001) "Isolation, characterization and transplantation of bone marrow-derived hepatocyte stem cells" Biochem Biophys Res Commun 288(1): 156-64.

Badiavas, et al. "Participation of bone marrow derived cells in cutaneous would healing." Journal of Cellular Physiology. 196(2): 245-250 (2003).

Bagnato, A. and Spinella, F. (2003) "Emerging role of endothelin-1 in tumor angiogenesis" Trends Endocrinol Metab 14, 44-50.

Bailey, A. J. et al., "Age-Related Changes in the Biochemical Properties of Human Cancellous Bone Collagen: Relationship to Bone Strength," *Calcified Tissue International*, 1999, 65:203-10.

(Continued)

*Primary Examiner* — Leon Blaine Lankford, Jr.
(74) *Attorney, Agent, or Firm* — Knobbe Martens Olson & Bear LLP

(57) ABSTRACT

Cells present in processed lipoaspirate tissue are used to treat patients. Methods of treating patients include processing adipose tissue to deliver a concentrated amount of stem cells obtained from the adipose tissue to a patient. The methods may be practiced in a closed system so that the stem cells are not exposed to an external environment prior to being administered to a patient. Compositions that are administered to a patient include a mixture of adipose tissue and stem cells so that the composition has a higher concentration of stem cells than when the adipose tissue was removed from the patient.

22 Claims, 7 Drawing Sheets

U.S. PATENT DOCUMENTS

| | | | |
|---|---|---|---|
| 5,980,887 | A | 11/1999 | Isner et al. |
| 6,010,696 | A | 1/2000 | Caplan et al. |
| 6,020,196 | A | 2/2000 | Hu et al. |
| 6,030,836 | A | 2/2000 | Thiede et al. |
| 6,086,582 | A | 7/2000 | Altman et al. |
| 6,090,121 | A | 7/2000 | Weber et al. |
| 6,139,757 | A | 10/2000 | Ohmura |
| 6,197,325 | B1 | 3/2001 | MacPhee et al. |
| 6,200,606 | B1 | 3/2001 | Peterson et al. |
| 6,206,873 | B1 | 3/2001 | Paolini et al. |
| 6,261,549 | B1 | 7/2001 | Fernandez et al. |
| 6,316,247 | B1 | 11/2001 | Katz et al. |
| 6,322,784 | B1 | 11/2001 | Pittenger et al. |
| 6,368,356 | B1 | 4/2002 | Zhong et al. |
| 6,387,369 | B1 | 5/2002 | Pittenger et al. |
| 6,429,013 | B1 | 8/2002 | Halvorsen et al. |
| 6,576,464 | B2 | 6/2003 | Gold et al. |
| 6,589,728 | B2 | 7/2003 | Csete et al. |
| 6,623,959 | B2 | 9/2003 | Harris |
| 6,777,231 | B1 | 8/2004 | Katz et al. |
| 6,804,558 | B2 | 10/2004 | Haller et al. |
| 7,078,230 | B2 | 7/2006 | Wilkison |
| 7,390,484 | B2 | 6/2008 | Fraser et al. |
| 7,651,684 | B2 | 1/2010 | Hedrick et al. |
| 7,767,452 | B2 | 8/2010 | Kleinsek |
| 7,771,716 | B2 | 8/2010 | Hedrick et al. |
| 7,887,795 | B2 | 2/2011 | Fraser et al. |
| 7,901,672 | B2 * | 3/2011 | Fraser et al. .......... 424/93.7 |
| 8,119,121 | B2 * | 2/2012 | Fraser et al. .......... 424/93.7 |
| 2001/0000802 | A1 | 5/2001 | Soykan et al. |
| 2001/0009757 | A1 | 7/2001 | Bischof et al. |
| 2002/0103542 | A1 | 8/2002 | Bilbo |
| 2002/0111694 | A1 | 8/2002 | Ellingsen et al. |
| 2003/0014126 | A1 | 1/2003 | Patel et al. |
| 2003/0069168 | A1 | 4/2003 | Xu et al. |
| 2003/0082152 | A1 | 5/2003 | Hedrick et al. |
| 2003/0100105 | A1 | 5/2003 | Poo et al. |
| 2003/0152558 | A1 | 8/2003 | Luft et al. |
| 2003/0161816 | A1 | 8/2003 | Fraser et al. |
| 2003/0161817 | A1 | 8/2003 | Young et al. |
| 2003/0211085 | A1 | 11/2003 | Sanberg et al. |
| 2003/0211602 | A1 | 11/2003 | Atala |
| 2003/0212024 | A1 | 11/2003 | Keating et al. |
| 2004/0067218 | A1 | 4/2004 | Casteilla et al. |
| 2005/0084961 | A1 | 4/2005 | Hedrick et al. |
| 2007/0212676 | A1 | 9/2007 | Takakura et al. |

FOREIGN PATENT DOCUMENTS

| | | |
|---|---|---|
| EP | 0 446 450 | 9/1991 |
| EP | 0 448 770 | 10/1991 |
| EP | 0 512 769 | 11/1992 |
| EP | 0 515 726 | 12/1992 |
| EP | 0 570 331 | 11/1993 |
| EP | 0 987 325 | 3/2000 |
| EP | 1 077 254 | 2/2001 |
| EP | 1 011 752 | 10/2004 |
| EP | 1 712 616 | 10/2006 |
| JP | 59-090649 | 5/1984 |
| JP | 01-141583 | 6/1989 |
| JP | 02-002884 | 1/1990 |
| JP | 02-295484 | 12/1990 |
| JP | 04-183381 | 6/1992 |
| JP | 04-267873 | 9/1992 |
| JP | 08-259604 | 10/1996 |
| JP | 11-57731 | 3/1999 |
| JP | 2000-325068 | 11/2000 |
| JP | 2003-024040 | 1/2003 |
| JP | 2001-231539 | 8/2003 |
| JP | 2004-272762 | 9/2004 |
| WO | WO 86/01111 | 2/1986 |
| WO | WO 87/03812 | 7/1987 |
| WO | WO 94/02156 | 2/1994 |
| WO | WO 94/27698 | 12/1994 |
| WO | WO 96/38482 | 12/1996 |
| WO | WO 97/18299 | 5/1997 |
| WO | WO 97/26326 | 7/1997 |
| WO | WO 97/39104 | 10/1997 |
| WO | WO 97/40137 | 10/1997 |
| WO | WO 97/41208 | 11/1997 |
| WO | WO 97/49827 | 12/1997 |
| WO | WO 98/04682 | 2/1998 |
| WO | WO 98/20731 | 5/1998 |
| WO | WO 98/32333 | 7/1998 |
| WO | WO 98/51317 | 11/1998 |
| WO | WO 99/01145 | 1/1999 |
| WO | WO 99/02654 | 1/1999 |
| WO | WO 99/03973 | 1/1999 |
| WO | WO 99/11789 | 3/1999 |
| WO | WO 99/28444 | 6/1999 |
| WO | WO 00/53795 | 9/2000 |
| WO | WO 01/21767 | 3/2001 |
| WO | WO 01/62901 | 8/2001 |
| WO | WO 02/055678 | 7/2002 |
| WO | WO 02/064157 | 8/2002 |
| WO | WO 02/068010 | 9/2002 |
| WO | WO 02/075302 | 9/2002 |
| WO | WO 02/081007 | 10/2002 |
| WO | WO 03/001329 | 1/2003 |
| WO | WO 03/022988 | 3/2003 |
| WO | WO 03/024215 | 3/2003 |
| WO | WO 03/039481 | 5/2003 |
| WO | WO 03/053346 | 7/2003 |
| WO | WO 03/053362 | 7/2003 |
| WO | WO 03/080801 | 10/2003 |
| WO | WO 2004/013275 | 2/2004 |
| WO | WO 2004/029230 | 4/2004 |
| WO | WO 2004/052418 | 6/2004 |
| WO | WO 2004/072828 | 8/2004 |
| WO | WO 2004/074457 | 9/2004 |
| WO | WO 2004/093934 | 11/2004 |
| WO | WO 2004/101015 | 11/2004 |
| WO | WO 2005/012480 | 2/2005 |
| WO | WO 2005/034843 | 4/2005 |
| WO | WO 2005/035738 | 4/2005 |
| WO | WO 2005/063967 | 7/2005 |
| WO | WO 2005/035742 | 4/2007 |

OTHER PUBLICATIONS

Banfi, A., Bianchi, G., Galotto, M., Cancedda, R., and Quarto, R. (2001) "Bone marrow stromal damage after chemo/radiotherapy: occurrence, consequences and possibilities of treatment" Leuk Lymphoma 42, 863-70.

Barghorn, A. et al., "a-Smooth Muscle Actin Distribution in the Pulmonary Vasculature Comparing Hypoplastic and Normal Fetal Lungs," *Pediatric Pathology & Laboratory Medicine*, 1998, 18:5-22.

Barker, J.N., Davies, S.M., DeFor, T., Ramsay, N. K., Weisdorf, D.J. and Wagner, J.E. (2001) "Survival after transplantation of unrelated donor umbilical cord blood is comparable to that of huan leukocyte antigen-matched unrelated donor bone marrow: results of a matched-pair analysis" Blood 97, 2957-61.

Barry, F.P., Boynton, R.E., Haynesworth, S., Murphy, J.M., and Zaia, J. (1999) "The monoclonal antibody SH-2, raised against human mesenchymal stem cells, recognizes an epitope on endoglin (CD105)" Biochem Biophys Res Commun 265, 134-9.

Bartynski, J.M., S. Marion et al. (1990) "Histopathologic evaluation of adipose autografts in a rabbit ear model" Otolaryngol Hea Neck Surg 102(4): 314-21.

Bastard, J. P. et al., "A Mini-Liposuction Technique Adapted to the Study of Human Adipocyte Glucose Transport System," *Diabetologia*, 36(Suppl. 1):A135, 1993.

Baylink, David J., "Glucocorticoid-Induced Osteoporosis," *The New England Journal of Medicine*, 1983, 309:306-8.

Becerra, José et al., "Demineralized Bone Matrix Mediates Differentiation of Bone Marrow Stromal Cells In Vitro: Effect of Age of Cell Donor," *Journal of Bone and Mineral Research*, 1996, 11:1703-14.

Beecken, W.D., Kramer, W., and Jonas, D. (2000) "New molecular mediators in tumor angiogenesis" J Cell Mol Med 4, 262-269.

Beiser, Ian H. And Irvin O. Kanat, "Subchondral Bone Drilling: A Treatment for Cartilage Defects," *Journal of Foot Surgery*, 1990, 29:595-601.

Bennett, JH, et al., 1991 *J. Cell Sci.* "Adipocytic cells cultured from marrow have osteogenic potential," 99(Pt1):131-139.

Berdel, W.E., Fink, U., Thiel, E., Stunkel, K., Greiner, E., Schwarzkopf, G., Reichert, A. and Rastetter, J. (1982) "Purification of human monocytes by adherence to polymeric fluorocarbon. Characterization of the monocyte-enriched cell fraction" Immunobiology 163, 511-520.

Beresford, et al., 1986 *Endo*. "1,25-Dihydroxyvitamin D3 and Human Bone-Derived Cells in Vitro: Effects on Alkaline Phosphatase, Type I Collagen and Proliferation," 119:1776-1785.

Bergeon, M.T. (1967) "Collagen: a review" J Okla State Med Assoc 60(6): 330-2.

Bernlohr, David A. et al., "Tissue Specific Expression of p422 protein, A putative Lipid Carrier, In Mouse Adipocytes," *Biochem. Biophys. Res. Comun.* 1985 132:850-855.

Bickenbach, J.R. and Dunnwald, M. (2000) "Epidermal stem cells: characteristics and use in tissue engineering and gene therapy" Adv Dermatol 16, 159-83.

Bjornson, et al., 1999 Science "Turning Brain into Blood: A Hematopoetic Fate Adopted by Adult Neural Stem Cells in Vivo," 283:534-537.

Björntrop, et al. "Isolation and characterization of cells from rat adipose tissue developing into adipocytes." J. Lipid Res. 19:316-324 (1978).

Block, C.A., C.S. Cooper (2003) "Long-term Efficacy of periurethral collagen injection for the treatment of urinary incontinence secondary to myelomeningocele" J Urol 169(1): 327-329.

Goering, G. and A.J. Huffstadt (1967) "The use of derma-fat grafts in the face" Br J Plast Surg 20(2): 172-8.

Boerner, C.F. (1988) "Allergic response to a porcine collagen corneal shield. Case report" Arch Opthalmol 106(2): 171.

Bond et al., 1999, "Human Subcutaneouspreadipocytes Differentiate Into osteoblasts," *FASEB Journal* 13:600A.

Bonner-Weir, S. and Sharma, A. (2002) "Pancreatic stem cells" J Pathol 197, 519-526.

Boskey, et al., 1985, "The Effect of Osteocalcin on In Vitro Lipid-Induced Hydroxyapatite Formation and Seeded Hydroxyapatite Growth," *Calc. Tiss. Int.* 37:75.

Botta, M., Manetti, F., and Corelli, F. (2000) "Fibroblast growth factors and their inhibitors" Curr. Pharm. Des 6, 1897-1924.

Breen, Ellen C. et al., "TGFb Alters Growth and Differentiation Related Gene Expression in Proliferating Osteoblasts In Vitro, Preventing Development of the Mature Bone Phenotype," *Journal of Cellular Physiology*, 1994, 160:323-35.

Bruder, et al., 1997 J. Cell Biochem. "Growth Kinetics, Self-Renewal, and the Osteogenic Potential of Purified Human Mesenchymal Stem Cells During Extensive Subcultivation and Following Cryopreservation," 64:278-294.

Bruder, Scott P. et al., "Bone Regeneration by Implantation of Purified, Culture-Expended Human Mesenchymal Stem Cells," *Journal of Orthopaedic Research*, 1998, 16:155-62.

Bulleid, J.J., D.C. John et al (2000) "Recombinant expression systems for the production of collagen" Biochem Soc Trans 28(4): 350-3.

Burres, S. (2001) "Soft-tissue augmentation with fascian" Clin Plast Surg 28(1): 101-10.

Buschmann, I.R. Busch, H.J., Mies, G., and Hossmann, K.A. (2003) "Therapeutic induction of arteriogenesis in hypoperfused rat brain via granulocyte-macrophage colony-stimulating factor" Circulation 108, 610-615.

Butler-Browne, et al., 1990 *Anat. Embryol.* (*Berl*) "Myosin heavy and light chain expression during human skeletal muscle development and precocious muscle maturation induced by thyroid hormone," 181:513-522.

Butnariu-Ephrat, Miriam et al., "Resurfacing of Goat Articular Cartilage by Chondrocytes Derived From Bone Marrow," *Clinical Orthopaedics and Related Research*, 1996, 330:234-43.

Campion, Dennis R., "The Muscle Satellite Cell: A Review," *Internationals Review of Cytology*, 1984, 87:225-51.

Caplan, A.I. and Bruder, S.P. (2001) "Mesenchymal stem cells: building blocks for molecular medicine in the 21st century" Trends Mol Med 7, 259-64.

Caplan, Arnold I., "Mesenchymal Stem Cells," *Journal of Orthopaedic Research*, 1991, 9:641-50.

Caplan, Arnold I., "The Mesengenic Process," *Clinics in Plastic Surgery*, 21:429-35, 1994.

Carano, R.A. and Filvaroff, E.H. (2003) "Angiogenesis and bone repair" Drug Discov. Today 8, 980-989.

Carmeliet, P. (2000) "Mechamisms of angiogenesis and arteriogenesis" Nat Med 6, 389-395.

Carmeliet, P. and A. Luttun (2001) "The emerging role of the bone marrow-derived stem cells in (therapeutic angiogenesis" Thromb Haemost 86(1): 289-97.

Carpandena, C.A. "Collagen alterations in adipose autograft's." Aesthetic Plastic Surgery vol. 18, 11-15 (1994).

Carranza-Bencano, A. et al., "Comparative Study of the Reconstruction of Articular Cartilage Defects with Free Costal Perichondrial Grafts and Free Tibial Periosteal Grafts: An Experimental Study on Rabbits," *Calcified Tissue International*, 1999, 65:402-7.

Castro, et al. "Failure of Bone Marrow Cells to Transdifferentiate into Neural Cells in Vivo." Science. 297:1299 (2002).

Castro, et al. "Response to Comment on 'Failure of Bone Marrow Cells to Transdifferentiate into Neural Cells in Vivo.'" Science. 299:1184c (2003).

Castro-Malaspina, H., W. Ebell, et al. (1984) "Human bone marrow fibroblast colony-forming units (CFU-F" Prog Clin Ciol Res 154: 209-36.

Cheifetz, S. et al., "Endoglin Is a Component of the Transforming Growth Factor-β Receptor System in Human Endothelial Cells," *J. Biol. Chem.*, 1992 267:19027-19030.

Chen, J. et al. Intravenous Administration of Human Bone Marrow Stromal Cells Induces Angiogenesis in the Ischemic Boundary Zone After Stroke in Rats, Circulation Research, Apr. 2003, vol. 92, pp. 692-699.

Chen, J. et al. Intravenous Bone Marrow Stromal Cell Therapy Reduces Apoptosis and Promotes Endogenous Cell Proliferation After Stroke in Femal Rat, J. Neuroscience Research, Sep. 2003, vol. 73 pp. 778-786.

Chen, Theresa L. et al., "1α,25-Dihydroxyvitamin D3 Receptors in Cultured Rat osteoblast-like Cells," J. Biol. Chem. 1983 258:4350-4355.

Chen, Xiaoli et al., "Differentiation-dependent expression of obese (ob) gene by preadipocytes and adipocytes in primary cultures of porcine stromal-vascular cells," *Biochimica et Biophysica Acta*, 1997, 1359:136-42.

Cheng S-L., et al., 1994 *Endo* "Differentiation of Human Bone Marrow Osteogenic Stromal Cells in Vitro: Induction of the Osteoblast Phenotype by Dexamethasone," 134: 277-286.

Chimal-Monroy, Jesús and Lino Díaz de Leé ón, "Expression of N-cadherin, N-CAM, fibronectin tenascin is stimulated by TGF-b1, b2, b3 and b5 during the formation of precartilage condensations," *The International Journal of Developmental Biology*, 1999, 43:59-67.

Cho,S.W. et al. "Engineering of volume-stable adipose tissues." *Biomaterials* 26, 3577-3585 (2005).

Cho,S.W. et al. "Enhancement of adipose tissue formation by implantation of adipogenic-differentiated preadipocytes." *Biochem Biophys Res Commun* 345, 588-594 (2006).

Choi et al. "Adipose tissue engineering using mesenchymal stem cells attached to injectable PLGA spheres." *Biomaterials* 26, 5855-5863 (2005).

Choi,Y.S. et al. "Adipogenic differentiation of adipose tissue derived adult stem cells in nude mouse." *Biochem Biophys Res Commun* 345, 631-637 (2006).

Chyun, et al., 1984 *Endo*. "Cortisol Decreases Bone Formation by Inhibiting Periosteal Cell Proliferation," 114:477-480.

Civin, C.I.,. Strauss, L.C., Fackler, M.J., Trischmann, T.M., Wiley, J.M., and Loken, M.R. (1990) "Positive stem cell selection-basic science" Prog Clin Biol Res 333, 387-401.

Clarke, D. and Frisen, J. (2001) "Differentiation potential of adult stem cells" Curr Opin Genet Dev 11, 575-80.

Clavijo-Alvarez,J.A. et al. "A novel perfluoroelastomer seeded with adipose-derived stem cells for soft-tissue repair." *Plast Reconstr Surg* 118, 1132-1142 (2006).

Coleman III, et al. "Autologous Collagen? Lipocytic Dermal Augmentation. A Histopathologic Study". J. Dermatol Surg Oncol. vol. 19, 1032-1040 (1993).

Coleman, S.R. (1995) "Long-term survival of fat transplants: controlled demonstrations" Aesthetic Plast Surg 19(5): 421-5.

Coleman, S.R. (2001). "Structural fat grafts: the ideal filler?" Clin Plast Surg 28(1): 111-9.

Coleman, W.P., 3rd (1991) "Autologous fat transplantation" Plast Reconstr Surg 88(4): 736.

Commons, G.W., Halperin, B., and Chang, C.C. (2001) "Large-volume liposuction: a review of 631 consecutive cases over 12 years" Plast Reconstr Surg 108, 1753-63.

Conget, A and JJ Minguell 1999 *J. Cell. Physiol* "Phenotypical and Functional Properties of Human Bone Marrow Mesenchymal Progenitor Cells," 181:67-73.

Connolly, J.F. (1998) "Clinical use of marrow osteoprogenitor cells to stimulate osteogenesis" Clin Orthop(355 Suppl): S257-66.

Considine, et al., "Paracrine stimulation of preadipocyte-enriched cell cultures by mature adipocytes," *American Journal of Physiology* 1996 270(5) E895-E899.

Cooper, et al., 1999 *J. Endocrinol.* "Glucocorticoid activity, inactivity and the osteoblast," 163: 159-164.

Crandall, David L. et al., "Identification of Estrogen Receptor b RNA in Human Breast and Abdominal Subcutaneous Adipose Tissue," *Biochemical and Biophysical Research Communications*, 248:523-6, 1998.

Crevensten et al. "Intervertebral Disc Cell Therapy for Regeneration: Mesenchymal Stem Cell Implantation in Rat Intervertebral Discs." Annals of Biomedical Engineering. 32(3):430-434 (2004).

Cronin,K.J. et al. "New murine model of spontaneous autologous tissue engineering, combining an arteriovenous pedicle with matrix materials." *Plast Reconstr Surg* 113, 260-269 (2004).

Dani, et al., "Differentiation of embryonic stem cells into adipocytes in vitro," *J.Cell Sci.* 1997 110, 1279-1285.

Davis, P.F. and Z.M. Mackie (1981) "A simple procedure for the separation of insoluble collagen and elastin" Anal Biochem 115(1): 11-7.

De Ugarte, D.A., Ashjian, P.H., Elbarbary, A., and Hedrick, M.H. (2003) "Future of fat as raw material for tissue regeneration" Ann Plast Surg 50, 215-9.

Deng, Weiwen et al., "In Vitro Differentiation of Human Marrow Stromal Cells into Early Progenitors of Neural Cells by Conditions That Increase Intracellular Cyclic AMP," *Biochemical and Biophysical Research Communications*, 2001, 282:148-52.

Dengler T et al. 2002. Stem Cell Therapy for the Infarcted Heart ("Cellular Cardiomyoplasty"), Herz 27:598-610.

Denker, A.E., et al., 1995 *Differentiation* "Formation of cartilage-like spheroids by micromass cultures of murine C3H101/2 cells upon treatment with transforming growth factor-b1," 59: 25-34.

Denker, et al., 1999 *Differentiation* "Chondrogenic differentiation of murine C3H10T1/2 multipotential mesenchymal cells: I. Stimulation by bone morphogenetic protein-2 in high-density micromass cultures," 64:67-76.

Dennis, James E. et al., "A Quadripotential Mesenchymal Progenitor Cell Isolated from the Marrow of an Adult Mouse," *Journal of Bone and Mineral Research*, 1999, 14:700-9.

Dias, Peter et al., "The Molecular Basis of Skeletal Muscle Differentiation," *Seminars in Diagnostic Pathology*, 1994, 11:3-14.

Diefenderfer, David L. and Carl T. Brighton, "Microvascular Pericytes Express Aggrecan Message Which is Regulated by BMP-2," *Biochemical and Biophysical Research Communications*, 2000, 269:172-8.

Dimri, et, al., 1995 *Proc. Natl. Acad. Sci. USA* "A biomarker that identifies a senescent human cells in culture and in aging skin in vivo," 92: 9363-9367.

D'Ippolito, G., Schiller, P.C., Ricordi, C., Roos, B.A., and Howard, G.A. (1999) "Age-related osteogenic potential of mesenchymal stromal stem cells from human vertebral bone marrow" J Bone Miner Res 14, 1115-22.

Donovan, D., Brown, N. J., Bishop, E.T. and Lewis, C.E. (2001) "Comparison of three in vitro human 'angiogenesis' assays with capillaries formed in vivo" Angiogenesis 4, 113-121.

Dragoo et al. "Tissue-engineered cartilage and bone using stem cells from human infrapatellar fat pads." The Journal of Bone and Joint Surgery. 85(5):740-747 (2003).

Ducy, et, al., 1997 *Cell* "Osf2/Cbfa1: A Transcriptional Activator of Osteoblast Differentiation," 89:747-754.

Eisenberg, Shlomo, "High density lipoprotein metabolism," *Journal of Lipid Research*, 1984, 25:1017-58.

Engleholm, S.A., Spang-Thomsen, M., Brunner N., Nohr, I., and Vindelov, L.L. (1985) "Disaggregation of human solid tumors by combined mechanical and enzymatic methods" Br J Cancer 51, 93-8.

Enomoto, Hirayuki et al., "Cbfa1 Is a Positive Regulatory Factor in Chondrocyte Maturation," J. Biol. Chem. 2000 275:8695-8702.

Entenmann, et al., "Relationship between replication and differentiation cultured human adipocyte precursor cells," *American Phys. Soc.* 1996 270,C1011-C1016.

Eppley, B.L., Smith, P.G., Sadove, A.M., and Delvino, J.J. (1990) "Experimental effects of graft revascularization and consistency on cervicofacial fat transplant survival" J Oral Maxillofac Surg 48, 54-62.

Eremia, S. and N. Newman (2000). "Long-term follow-up after autologous fat grafting: analysis of results from 116 patients followed at least 12 months after receiving the last of a minimum of two treatments" Dermatol Surg 26(12): 1150-8.

Erickson et al. "Chondrogenic potential of adipose tissue derived stromal cells in vitro and in vivo." Biochemical and Biophysical Research Communications. 290(2):763-769 (2002).

Ersek, Robert A. "Transplantation of Purified Autologous Fat: A 3-Year Follow-Up is Disappointing." Plast. Reconst. Surg. 87(2):219-228 (1991).

Eschenhagen, T., Didie, M., Muzel, FI, Schubert, P., Schneiderbanger, K., and Zimmermann, W.H. (2002) "3D engineered hear tissue for replacement therapy" Basic Res Cardiol 97 Suppl 1, 1146-1152.

Eslami Varzaneh, et al., "Extracellular Matrix Components Secreted by Microvascular Endothelial Cells Stimulate Preadipocyte Differentiation In Vitro," *Metabolism* 1994 43 (7), 906-912.

Fain et al. "Comparison of the Release of Adipolines by Adipose Tissue, Adipose Tissue Matrix, and Adipocytes from Visceral and Subcutaneous Abdominal Adipose Tissues of Obese Humans." Endocrinology. 145(5):2273-2282, at 2278, col. 2 (2004).

Fajas, Lluis, et al., "Transcriptional control of adipogenesis," *Current Opinion in Cell Biology*, 1998, 10:165-73.

Falla, N., Van V., Bierkens, J., Borremans, B., Schoeters, G., and Van Gorp, J. (1993) "Characterization of a 5-flurorouracil-enriched osteoprogenitor population of the murine bone marrow" Blood 82, 3580-91.

Farndale, Richard W. et al., "Improved quantitation and discrimination of sulphated glycosaminoglycans by use of dimethylene blue," *Biochimica et Biophysica Acta*, 1986, 883:173-7.

Ferrari G., et al., 1998 *Science* "Muscle Regeneration by Bone Marrow-Derived Myogenic Progenitors," 279: 1528-1530.

Folkman, J. (1995) "Angiogenesis in cancer, vascular, rheumatoid and other disease" Nat Med 1, 27-31.

Ford, C.N., P.A. Staskowski et al. (1995) "Autologous collagen vocal fold injection: a preliminary clinical study" Laryngoscope 105(9 Pt 1): 944-8.

Formanek, M., Temmel, A., Knerer, B., Willheim, M., Millesi, W., and Kornfehl, J. (1998) "Magnetic cell separation for purification of human oral keratinocytes: an effective method for functional studies without prior cell subcultivation" Eur Arch Otorhinolaryngol 255, 211-215.

Fortier, Lisa, et al., 2000, "Isolation and chondrocytic differentiation of equine bone marrow-derived mesenchymal stem cells," *Am. J. Vet. Res.* 59:1182-1187.

Fraser JK. Adipose Tissue: Challenging the Marrow Monopoly. Cytotherapy. 4(6):509-510 (2002).

Frederikson and McKay 1988 *J. Neurosci.* "Proliferation and Differentiation of Rat Neuroepithelial Precursor Cells in vivo," 8:1144-1151.

Fridman, et al., 1992 *Int. J. Cancer* "Malignant Transformation of NIH-3T3 Cells After Subcutaneous co-Injection With A Reconstituted Basement Membrane (Matrigel)," 51(5), 740-44.

Fukuda, K. (2001). "Development of regenerative cardiomyocytes from mesenchymal stem cells for cardiovascular tissue engineering" Artif Organs 25(3): 187-93.

Fülöp, Csaba et al., "Expression of Alternatively Spliced Epidermal Growth Factor-like Domains in Aggrecans of Different Species," *The Journal of Biological Chemistry*, 1993, 268:17377-83.

Fulton et al., "Fat Grafting" *Fundamentals of Cosmetic Surgery.* 19(3):523-530 (Jul. 2001).

Ganey et al. "A potential role for cell-based therapeutics in the treatment of intervertebral disc herniation." Eur Spine J. 11(Suppl. 2):S206-214 (2002).

Ganey et al. "Intervertebral Disc Repair Using Adipose Tissue-Derived Stem and Regenerative Cells." 34(21):2297-2304 (2009).

Garcia-Olmo et al., "Autologous Stem Cell Transplantation for Treatment of Rectovaginal Fistula in Perianal Crohn's Disease: A New Cell-Based Therapy", Int. J Colorectal Dis (2003), 18:451-454.

Gaustad, K.G., Boquest, A.C., Anderson, B.E., Gerdes, A.M., and Collas, P. (2004) "Differentiation of human adipose tissue stem cells using extracts of rat cardiomyocytes" Biochem. Biophys. Res Commun. 314, 420-427.

Geiselhart, A., Neu, S., Buchholz, F., Lang, P., Niethammer, D., and Handgretinger, R. (1996) "Postive selection of CD56+ lymphocytes by magnetic cell sorting" Nat Immun. 15, 227-233.

Gimble et al. "Adipose-Derived Adult Stem Cells: Isolation, Characterization, and Differentiation Potential." Cytotherapy. 5(5):362-369 (2003).

Gimble, Jeffery M. et al., "Adipose tissue-derived therapeutics," *Expert Opin. Biol.,* 2003, 3(5)705-713.

Glowacki, J., "Influence of Age on Human Marrow," *Calcified Tissue International*, 1995, 56(Supp. 1):S50-1.

Greenberg, A.W. and Hammer, D.A. (2001) "Cell separation mediated by differential rolling adhesion" Biotechnol Bioeng 73 111-24.

Grigoradis A., et al., 1988 *J. Cell Biol.* "Differentiation of Muscle, Fat, Cartilage, and Bone from Progenitor Cells Present in a Bone-derived Clonal Cell Population: Effect of Dexamethasone," 106: 2139-2151.

Grigoriadis, Agamemnon E. et al., "Analysis of chondroprogenitor frequency and cartilage differentiation in a novel family of clonal chondrogenic rat cell lines," *Differentiation*, 1996, 60:299-307.

Groutz, A., J.G. Blavias et al (2000) "Outcome results of transurethral collagen injection for female stress incontinence: assessment by urinary incontinence score" J Urol 164(6): 2006-9.

Guerrerosantos, J., A. Gonzalez-Mendoza, et al. (1996). "Long-term survival of free fat grafts in muscle: an experimental study in rats." Aesthetic Plast Surg 20(5): 403-8.

Guerriero, V and JR Florini 1980 *Endocrinology* "Dexamethasone Effects on Myoblast Proliferation and differentiation," 106:1198-1202.

Haab, F., P.E. Zimmern et al (1997) Urinary stress incontinence due to intrinsic sphincteric deficiency: experience with fat and collagen periurethral injections: J Urol 157(4): 1283-6.

Hagege, A.A., Carrion, C., Menasche, P., Vilquin, J.T., Duboc, D., Marolleau, J.P., Desnos, M., and Bruneval, P. (2003) "Viability and differentiation of autologous skeletal myoblast grafts in ischaemic cardiomyopathy" Lancet 361, 491-2.

Hak et al., "Toxic effects of DMSO on cultured beating heart cells at temperatures above zero," Cryobiology, 1973, 10:244-250.

Hall, BK 1981 "Intracellular and extracellular control of differentiation of cartilage and bone," Histochem. J. 13:599-614.

Hamano et al. The induction of angiogenesis by the implantation of autologous bone marrow cells: A novel and simple therapeutic method. Surgery. 130(1):44-54 (2001).

Hamel, M., T. Shaarawy et al (2001) "Deep sclerectomy with collagen implant in patients with glaucoma and high myopia" J Cataract Refract Surg 27(9): 1410-7.

Hardingham, Tim et al., "Studies on the Synthesis, Secretion and Assembly of Proteoglycan Aggregates by Chondrocytes," *Matrices and Cell Differentiation*, 1984, 151:17-29.

Hauner H. et al., "Glucocorticoids and Insulin Promote the Differentiation of Human Adipocyte Precursor Cells into Fat Cells," *Journal of Clinical Endocrinology and Metabolism*, 64:832-5, 1987.

Hauner, et al., "Endothelin-1 Inhibits the Adipose Differentiation of Cultured Human Adipocyte Precursor Cells," *Metabolism* 1994 43(2) pp. 227-232.

Hauner, Hans et al., "Promoting Effect of Glucocorticoids on the Differentiation of Human Adipocyte Precursor Cells Cultured in a Chemically Defined Medium," *Journal of Clinical Investigation*, 84:1663-70, 1989.

Hausman, et al., "The Influence of Extracellular Matrix Substrata on Preadipocyte Development in Serum-Free Cultures of Stromal-Vascular Cells," *J. Anim.Sci.* 1996 74(9), 2117-2128.

Haynesworth, S. E. et al., "Cell Surface Antigen on Human Marrow-Derived Mesenchymal Cells are Detected by Monoclonal Antibodies," *Bone*, 1992, 13:69-80.

Hemmrich,K. et al. "Implantation of preadipocyte-loaded hyaluronic acid-based scaffolds into nude mice to evaluate potential for soft tissue engineering." *Biomaterials 26*, 7025-7037 (2005).

Hemstreet, G.P. 3, Enoch, P.G., and Pretlow, T.G. 2 (1980) "Tissue disaggregation of human renal cell carcinoma with further isopyknic and isokinetic gradient purification" Cancer Res 40, 1043-9.

Herman, Ira M. And Patricia D'Amore, "Microvascular Pericytes Contain Muscle and Nonmuscle Actins," *J. Cell Biol.* 1985 101:43-52.

Hess, D.C. et al. Hematopoietic Origin of Microglial and Perivascular Cells in Brain, Experimental Neurology, Apr. 2004, vol. 186, pp. 134-144.

Hironori et al. The Japan Endocrine Society Journal. 80(1):90 (Apr. 2004).

Hong et al. "Adipose tissue engineering by human adipose-derived stromal cells." *Cells Tissues Organs* 183, 133-140 (2006).

Horwitz, E. M., D.J. Prockop, et al. (1999). "Transplantability and therapeutic effects of bone marrow-derived mesenchymal cells in children with osteogenesis imperfecta." Nat Med 5(3): 309-13.

Horwitz, E.M., Prockop, D.J., Gordon, P.L., Koo, W. W., Fitzpatrick, L.A., Neel, M.D., McCarville, M.E., Orchard, P.J., Pyeritz, R.E., and Brenner, M.K. (2001) "Clinical responses to bone marrow transplantation in children with severe osteogenesis imperfecta." Blood 97(5), 1227-31.

Hsiung, M. W., P. Woo et at (2000) "Fat augmentation for glottic insufficiency" Laryngoscope 110(6): 1026-33.

Huang, J.I., S.R. Beanes, et al. (2002) "Rat extramedullary adipose tissue as a source of osteochondrogenic progenitor cells" Plast Reconstr Surg 109(3): 1033-41; discussion 1042-3.

Huibregtse, Barbara, et al., 1998, "Effect of Age and Sampling Site on the Chondro-Osteogenic Potential of Rabbit Marrow-derived Mesenchymal Progenitor Cells," *Journal of Orthopaedic Research*. 18:18-24.

Hui-Ling et al., "Increased expression of G in mouse embryo stem cells promotes terminal differentiation to adipocytes," *American Physiological Society* 1993 265(6), C1729-C1735.

Hur et al. Akt Is a Key Modulator of Endothelial Progenitor Cell Trafficking in Ischemic Muscle. Stem Cells. 25:1769-1778 (2007).

Huss, Ralf, "Isolation of Primary and Immortalized CD34-Hematopoietic and Mesenchymal Stem Cells from Various Sources," *Stem Cells*, 2000, 18:1-9.

Hutley, L.J., A.C. Herington, et al. (2001) "Human adipose tissue endothelial cells promote preadipocyte proliferation" Am J. Physiol Endocrinol Metab 281(5): E1037-44.

Iwasaki, Motoki et al., "Regulation of Proliferation and Osteochondrogenic Differentiation of Periosteum-Derived Cells by Transforming Growth Factor-b and Basic Fibroblast Growth Factor," *Journal of Bone and Joint Surgery*, 1995, 77A:543-54.

Jackson et al. Regeneration of ischemic cardiac muscle and vascular endothelium by adult stem cells. Journal Clinical Investigation. 107(11): 1395-1402 (2001).

Jaiswal, et al., 1997 "Osteogenic Differentiation of Purified, Culture-Expanded Human Mesenchymal Stem Cells In Vitro," J. Cell Biochem. 64:295-312.

Jaiswal, R.K., Jaiswal, J., Bruder, S.P., Mbalaviele, G., Marshak, D.R., and Pittenger, M.F. (2000) "Adult human mesenchymal stem cell differentiation to the osteogenic or adipogenic lineage is regulated by mitogen-activated protein kinase" J Biol Chem 275, 9645-52.

Jiang, Y., Jahagirdar, B.N., Reinhardt, R.L., Schwartz, R.E., Keene, C.D., Ortiz-Gonzalez, X.R., Reyes, M. Lenvik, T., Lund, T., Blackstad, M., Du, J., Aldrich, S., Lisberg, A., Low, W.C., Largaespada, D.A., and Verfaillie, C.M. (2002a) "pluripotency of mesenchymal stem cells derived from adult marrow" Nature 418, 41-9.

Jiang, Y., Vaessen, B., Lenvik, T., Blackstad, M., Reyes, M., and Verfaillie, C.M. (2002b) "Multipotent progenitor cells can be isolated from postnatal murine bone marrow, muscle, and brain" Exp Hematol 30, 896-904.

Johnson, P. R. et al., "Uncontrolled adipocyte proliferation is not the primary lesion in the genetically-obese Zucker rat," *International Journal of Obesity*, 5:563-70, 1981.

Johnstone B., et al., 1998 "In Vitro Chondrogenesis of Bone Marrow-Derived Mesenchymal Progenitor Cells," Exp. Cell Res. 238: 265-272.

Joyner, C.J., Triffitt, J., Puddle, B., and Athanasou, N.A. (1999) "Development of a monoclonal antibody to the aP2 protein to identify adipocyte precursors in tumours of adipose differentiation" Pathol. Res Pract. 195, 461-466.

Jurgens et al. "Effect of tissue-harvesting site on yield of stem cells derived from adipose tissue: implications for cell-based therapies." Cell Tiss. Res. 332:415-426 (2008).

Kale et al. "Bone marrow stem cells contribute to repair of the ischemically injured renal tubule" J. Clinical Investigation, vol. 112, No. 1 42-49 (Jul. 2003).

Kamer, F.M. and M.M. Churukian (1984) "Clinical use of injectable collagen. A three-year retrospective review" Arch Otolaryngol 110(2): 93-8.

Kamihata et al. "Improvement of collateral perfusion and regional function by implantation of peripheral blood mononuclear cells into ischemic hibernating myocardium." Thromb Vascular Biology. 22:1804-1810 (2002).

Kang et al. "Improvement of neurological deficits by intracerebral transplantation of human adipose tissue-derived stromal cells after cerebral ischemia in rats." Experimental Neurology. 183(2):355-366 (2003).

Kang et al. "Interactions between human adipose stromal cells and mouse neural stem cells in vitro." Developmental Brain Research. 145(1): 141-149 (2003).

Kania, et al., 1990 "The *Drosophila* segmentation gene *runt* encodes a novel nuclear regulatory protein that is also expressed in the developing nervous system," Genes Dev. 4:1701-1713.

Karlsson et al., "Long-term storage of tissues by cryopreservation: critical issues," Biomaterials 1996, 17(3):243-256.

Katz, a.J., Hedrick, M.H., Llull, R., and Futrell, J.W. (2001) "A novel device for the simple and efficient refinement of liposuctioned tissue" Plast Reconstr Surg 107, No. 2, 595-597.

Katz, Adam J. et al., "Emerging Approaches to the Tissue Engineering of Fat," *Clinics in Plastic Surgery*, 1999, 26:587-603.

Katz, B.E., Bruck, M.C. and Coleman, W. P. 3 (2001b) "The benefits of powered liposuction versus traditional liposuction: a paired comparison analysis" Dermatol Surg 27, 863-7.

Kaushal, S., Amiel, G.E., Guleserian, K.J., Shapira, O.M., Perry, T., Sutherland, F.W., Rabkin, E., Moran, A.M. Schoen, F.J., Atala, A., Soker, S., Bischoff, J., and Mayer, J.E., Jr. (2001) "Functional small-diameter neovessels cretaed using endothelial progenitor cells expanded ex vivo" Nat Med 7, 1035-40.

Kawamoto, A., Tkebuchava, T., Yamaguchi, J., Nishimura, H., Yoon, Y.S., Milliken, C., Uchida, S., Masuo, O., Iwaguro, H., Ma, H., Hanley, A., Silver, M., Kearney, M., Lorsordo, D.W., Isner, J.M. and Asara, T. (2003) "Intramyocardial transplantation of autologous endothelial progenitor cells for therapeutic neovascularization of myocardial ischemia" Circulation 107, 461-8.

Kehlen, A. et al., 2000 *J. Cell Biochem.* "Increased Lymphocytic Aminopeptidase N/CD13 Promoter Activity After Cell-Cells Contact," 80:115-123.

Kern, P.A., A. Knedler, et al. (1983) Isolation and culture of microvascular endolthellium from human adipose tissue: J Clin Invest 71(6): 1822-9.

Killinger, D. W. et al., "Influence of Adipose Tissue Distribution on the Biological Activity of Androgens," *Annals New York Academy of Sciences*, 595:199-211, 1990.

Killinger, Donald W. et al., "The Relationship Between Aromatase Activity and Body Fat Distribution," *Steroids*, 50:61-72, 1987.

Kim, et al. "Wound healing effect of adipose-derived stem cells: A critical role of secretory factors on human dermal fibroblasts." Journal of Dermatological Science. 48(1): 15-24 (2007).

Kimura et al. "Adipose tissue engineering based on human preadipocytes combined with gelatin microspheres containing basic fibroblast growth factor." *Biomaterials* 24, 2513-2521 (2003).

Kirsch, Thorsten and Klaus von der Mark, "Remodelling of collagen types I, II and X and calcification of human fetal cartilage," *Bone and Mineral*, 1992, 18:107-17.

Klein, A.W. (2001) "Skin filling. Collagen and other injectables of the skin" Dermatol Clin 19(3): 491-508, ix.

Kosher, RA, et al., 1986 *J. Cell Biol.* "Collagen Gene Expression During Limb Cartilage Differentiation," 102:1151-1156.

Kosher, Robert A. and Michael Solursh, "Widespread Distribution of Type II Collagen during Embryonic Chick Development," *Developmental Biology*, 1989, 131:558-66.

Koufman, J.A. (1991) "Lipoinjection for vocal cord paralysis" Laryngoscope 101(12 Pt 1): 1385.

Kuri-Harcuch, W. et al., 1984, *Differentiation* "Extracellular matrix production by mouse 3T3-F442A cells during adipose differentiation in culture," 28.

Lafontan, M. et al., "Réflexions sur une nouvelle approche de chirurgie plastique réparatrice: la réimplantation de fragments de tissu adipeux prélevés par liposuccion," *Ann. Chir. Plast. Esthet.*, 34:77-81, 1989.

Lam, Anson and Ronald Moy, "The Potential for Fat Transplantation," *J. Dermatol. Surg. Oncol.*, 18:432-4, 1992.

Lamouille, S., Mallet, C., Feige, J.J., and Bailly, S. (2002) "Activin receptor-like kinase 1 is implicated in the maturation phase of angiogenesis" Blood 100, 4495-4501.

Lanier, L.L. et al, 1991 *J. Immunol.* "Molecular and Functional Analysis of Human Natural Killer Cell-Associated Neural Cells Adhesion Molecule (N-Cam/CD56)," 146:4421-4426.

Lasch, J., Kullertz, G., and Opalka, J.R. (2000) "Separation of erythrocytes into age-related fractions by density or size? Counterflow centrifugation" Clin Chem Lab Med 38, 629-632.

Latoni, J.D., D.M. Marshall et al (2000 "Overgrowth of fat autotransplanted for correction of localized steroid-induced atrophy" Plast Reconstr Surg 106(7): 1566-9.

Lawson-Smith, M.J. And McGeachie, J.K. 1998 *J. Anat.* "The identification of myogenic cells in skeletal muscle, with emphasis on the use of tritiated thymidine autoradiography and desmin antibodies," 192:161-171.

Lazarus, Hillard M. et al., "Human Bone Marrow-Derived Mesenchymal (Stromal) Progenitor Cells (MPCs) Cannot Be Recovered from Peripheral Blood Progenitor Cell Collections," *Journal of Hematotherapy*, 1997, 6:447-55.

Leboy, et al., 1991 *J. Cell Physiol.* "Dexamethasone Induction of Osteoblast mRNAs in Rat Marrow Stromal Cell Cultures," 146:370-378.

Leboy, Phoebe S. et al., "Ascorbic Acid Induces Alkaline Phosphatase, Type X Collagen, and Calcium Deposition in Cultured Chick Chondrocytes," *The Journal of Biological Chemistry*, 1989, 264:17281-6.

Lecoeur, L. and J. P. Ouhayoun, "In vitro induction of osteogenic differentiation from non-osteogenic mesenchymal cells," *Biomaterials*, 18:989-93, 1997.

Lee, J. H., Z. Ilic, et al. (1996) "Cell kinetics of repair after allyl alcohol-induced liver necrosis in mice" Int J Exp Pathol 77(2): 63-72.

Lee, P.E., R.C. Knug, et al. (2001) "Periurethral autologous fat injection as treatment for female stress urinary incontinence: a randomized double-blind controlled trial" J Urol 165(1): 153-8.

Lee, Yun-Shain and Cheng-Ming Chuong, "Adhesion Molecules in Skeletogenesis: I. Transient Expression of Neural Cell Adhesion Molecules (NCAM) in Osteoblasts During Endochondral and Intramembranous Ossification," *Journal of Bone and Mineral Research*, 1992, 7:1435-46.

Lehner, M. and Holter, W. (2002) "Endotoxin-free purification of monocytes for dendritic cell generation via discontinuous density gradient centrifugation based on diluted Ficoll-Paque Plus" Int Arch Allergy Immunol 128, 73-76.

Lendahl, et al., 1990 *Cell* "CNS Stem Cells Express a New Class of Intermediate Filament Protein," 60:585-595.

Lennon, D.P., Haynesworth, S.E., Young, R.G., Dennis, J.E., and Caplan, A.I. (1995) "A chemically defined medium supports in vitor proliferation and maintains the osteochondral potential of rat marrow-derived mesenchymal stem cells" Exp Cell Res 219, 211-22.

Lennon, Donald P. et al., "Human and Animal Mesenchymal Progenitor Cells from Bone Marrow: Identification of Serum for Optimal Selection and Proliferation," *In Vitro Cell. Dev. Biol.—Animal*, 1996, 32:602-11.

Lenoir, N. 2000 *Science* "Europe Confronts The Embryonic Stem Cell Research Challenge," 287:1425-1427.

Lev, Robert and S. S. Spicer, "Specific Staining of Sulphate Groups with Alcian Blue at Low pH," *J. Histochem. Cytochem.*, 1964, 12:309-10.

Lin, et al. "Hematopoietic Stem Cells Contribute to the Regeneration of Renal Tubules After Renal Ischmia-Reperfusion Injury in Mice." Journal of the American Society of Nephrology. 14: 1188-1199 (2003).

Linsenmayer, Thomas et al., 1998, "Type X Collagen: A Hypertrophic Cartilage-Specific Molecule," *Pathol. Immunopathol.* 7:14-19.

Liu, S.H., R.S. Yang et al (1995) "Collagen in tendon, ligament and bone healing. A current review" Clin Orthop (318): 265-78.

Loncar, D., "Ultrastructural analysis of differentiation of rat endoderm in vitro. Adipose vascular-stromal cells induce endoderm differentiation, which in turn induces differentiation of the vascular-stromal cells into chondrocytes," *J. Submicrosc. Cytol. Pathol.*, 24:509-19, 1992.

Long, Michael W. et al., "Age-Related Phenotypic Alterations in Populations of Purified Human Bone Precursor Cells," *The Journals of Gerontology*, 1999, 54A:B54-62.

Lucas, P. A. et al., "Isolation of Putative Mesenchymal Stem Cells from Rat Embryonic and Adult Skeletal Muscle," *In Vitro Cell Dev. Biol.*, 1992, 28:154A.

Lucas, Paul A. et al., "Mesenchymal Stem Cells From Granulation Tissue," *J. Cell Biochem*, 1993 17E:122, R212.

Lumelsky, N., et al. 2001 *Science* "Differentiation of Embryonic Stem Cells to Insulin-Secreting Structures Similar to Pancreatic Islets," 292:1389-1394.

Lund et al. "Granulocyte colony-stimulating factor mobilized CFU-F can be found in the peripheral blood but have limited expansion potential." Haematologica. 93(6):908-912 (2008).

Luskey, B.D., Lim, B., Apperley, J.F., Orkin, S.H., and Williams, D.A. (1990) "Gene transfer into murine hematopoietic stem cells and bone marrow stromal cells" Ann NY Acad Sci 612, 398-406.

Lynch, et al., 1995, *Exp. Cell Res.* "The Influence of Type I Collagen on the Development and Maintenance of the Osteoblast Phenotype in Primary and Passaged Rat Calvarial Osteoblasts: Modification of Expression of Genes Supporting Cell Growth, Adhesion, and Extracelluar Matrix Mineralization," 216:35-45.

MacDougald, Ormond A. and M. Daniel Lane, "Transcriptional Regulation of Gene Expression During Adipocyte Differentiation," *Annu. Rev. Biochem.*, 1995, 64:345-73.

Mainwaring, G. and Rowley, A.F. (1985) "Separation of leucocytes in the dogfish (*Scyliorhinus canicula*) using density gradient centrifugation and differential adhesion to glass coverslips" Cell Tissue Res 241, 283-90.

Majeska, Robert J. and Gideon A. Rodan, "The Effect of 1,25(OH)2D3 on Alkaline Phosphates in Osteoblastic Osteosarcoma Cells," *J. Biol. Chem.* 1982 257:3362-3365.

Majumdar, M.K., Thiede, M.A., Mosca, J.D., Moorman, M., and Gerson, S.L. (1998) "Phenotypic and functional comparison of cultures of marrow-derived mesenchymal stem cells (MSCs) and stromal cells" J Cell Physiol 176, 57-66.

Malaval, et al., 1994 J. Cell. Physiol. "Cellular Expression of Bone-Related Proteins During In Vitro Ostegenesis in Rat Bone Marrow Stromal Cell Culture," 158:555-572.

Manduca, et al., 1992 *Eur. J. Cell Biol.* "Chondrogenic differentiation in chick embryo osteoblast cultures," 57:193-201.

Marchlinski, F.E., Falcone, R., Iozzo, R.V., Reichek, N., Vassallo, J.A., and Eysmann, S.B. (1987) "Experimental myocardial cryoinjury: local electromechanical changes, arrhythmogenicity, and methods for determining depth of injury" Pacing Clin Electrophysiol 10, 886-901.

Marko, et al., "Isolation of a Preadipocyte Cell Line from Rat Bone Marrow and Differentiation to Adipocytes," *Endocrinology* 1995 136(10), 4582-4588.

Martin, et al., 1999 *Exp. Cell Res.* "Mammalian Chondrocytes Expanded in the Presence of Fibroblast Growth Factor 2 Maintain the Ability to Differentiate and Regenerate Three-Dimensional Cartilaginous Tissue," 253:681-688.

Martinez-Estrada et al. "Human adipose tissue as a source of Flk-1 <+> cells: new method of differentiation and expansion." Cardiovascular Research. 65(2):328-333 (2005).

Masuda, et al. "Photocured, styrenated gelatin-based microspheres for de novo adipogenesis through corelease of basic fibroblast growth factor, insulin, and insulin-like growth factor I." *Tissue Eng* 10, 523-535 (2004).

Masuda et al. "Novel strategy for soft tissue augmentation based on transplantation of fragmented omentum and preadipocytes." *Tissue Eng* 10, 1672-1683 (2004).

Megeney, et al., 1996 *Genes Dev.* "MyoD is required for myogenic stem cell function in adult skeletal muscle," 10:1173-1183.

Mezey, et al. "Comment on 'Failure of Bone Marrow Cells to Transdifferentiate into Neural Cells in Vivo.'" Science. 299-1184b (2003).

Miller, J.J. and J.C. Poop (2002) "Fat hypertrophy after autologous fat transfer" Opthal Plast Reconstr Surg 18(3): 228-31.

Mills, J.D., Fischer, D., and Villaneuva, F.S. (2000) "Coronary collateral development during chronic ischemia: serial assessment using harmonic myocardial contrast echocardiography" J Am Coll Cardiol 36(2):618-24.

Miranville, et al. "Improvement of postnatal neovascularization by human adipose tissue-derived stem cells." Circulation, American Heart Association. 110(3):349-355 (2004).

Miranville et al. "Human adipose tissue-derived stem cells improve blood flow in the ischemic mouse hind-limb" Circulation, vol. 108, No. 17, Supp. IV, 164 (Oct. 2003).

Miranville et al. "Human adipose tissue-derived stem cells improve postnatal neovascularization." International Journal of Obesity. 28(Suppl 1):S100 (May 2004).

Mizuno, H., P.A. Zuk, et al. (2002) "Myogenic differentiation by human processed lipoaspirate cells" Plast Reconstr Surg 109(1): 199-209; discussion 210-1.

Molkentin and Olson 1996 *Curr. Opin. Genet. Dev.* "Defining the regulatory networks for muscle development," 6:445-453.

Monteiro, P., Antunes, A., Goncalves, L.M., and Providencia, L.A. (2003) "Long-term clincal impact of coronary-collateral vessels after acute myocardial infarction" Rev. Port. Cardiol 22, 1051-1061.

Morizono, K., De Ugarte, D.A., Zhu, M., Zuk, P., Elbarbary, A., Ashjian, P., Benhaim, P. Chen, I.S., and Hedrick, M.H. (2003) "Multilineage cells from adipose tissue as gene delivery vehicles" Hum Gene Ther 14, 59-66.

Mosca, J.D. Hedricks, J.K. Buyaner, D., Davis-Sproul, J., Chuang, L.C., Majumdar, M.K., Chopra, R., Barry, F., Murphy, M., Thiede, M.A. Junker, U., Rigg, R.J., Forestell, S.P., Bohnlien, E., Storb, R., and Sandmaier, B.M. (2000) "Mesenchymal stem cells as vehicles for gene delivery" Clin Orthop 71-90.

Mullen, Richard J. et al., "NeuN, a neuronal specific nuclear protein in vertebrates," *Development*, 1992, 116:201-11.

Muller et al. "Selection of ventricular-like cardiomyocytes from ES cells in vitro." The FASEB Journal. 14:2540-2548 (2000).

Mullins, R.J., C. Richards et al. (1996) "Allergic reactions to oral, surgical and topical bovine collagen. Anaphylactic risk for surgeons" Aust N Z J Ophthalmol 24(3): 257-60.

Mundlos, et al., 1997 *Cell* "Mutations Involving the Transcription Factor CBFA12 Cause Cleidocranial Dysplasia," 89:773-779.

Muramatsu, T., Nakamura, A., and Park, H.M. (1998) "In vivo electroportion: a powerful and convenient means of nonviral gene transfer to tissues of living animals (Review)" Int J Mol Med 1, 55-62.

Murayama, T., O.M. Tepper, et al. (2002) "Determination of bone marrow-derived endothelial progenitor cells significance in angiogenic growth factor-induced neovascularization in vivo" Exp Hematol 30(8): 967-72.

Murry, C.E., Wiseman, R.W., Schwartz, S.M., and Hauschka, S.D. (1996) skeletal myoblast transplantation for repair of myocardial necrosis: J Clin Invest 98, 2512-23.

Murry CE et al. 2004. Hematopoietic stem cells do not transdifferentiate into cardiac myocytes in myocardial infarcts. Nature 428: 664-668.

Muschler, G.F., Nitto, H., Boehm, C.A., and Easley, K.A. (2001) "Age-and gender-related changes in the cellularity of human bone marrow and the prevalence of osteoblastic progenitors" J Orthop Res 19(1), 117-25.

Myllyharju, J. (2000) "Recombinant collagen trimers from insect cells and yeast" Methods Mol Biol 139: 39-48.

Nagle, R. B. et al., "Factor VII-Associated Antigen in Human Lymphatic Endothelium," *Lymphology*, 1987, 20:20-4.

Nagy, J.A., Dvorak, A. M., and Dvorak, H.F. (2003) VEGF-A (164/165) and PIGF: roles in angiogenesis and arteriogenesis: Trends Cardiovasc Med 13, 169-175.

Nakahara, H. et al., "Bone and Cartilage Formation in Diffusion Chambers by Subcultured Cells Derived from the Periosteum," *Bone*, 1990, 11:181-8.

Nakajima, I. et al., 1998, "Adipose tissue extracellar matrix: newly organized by adipocytes during differentiation," *Differentiation* 63:193-200.

Nakano, Hirotaka et al., "RT-PCR Suggests Human Skeletal Muscle Origin of Alveolar Soft-Part Sarcoma," *Oncology*, 2000, 58:319-23.

Nambu et al. Japanese Society for Biomaterials, Conference Proceedings. 25:96 (2003).

Nathan, Suresh et al. "Cell-Based Therapy in the Repair of Osteochrondral Defects: A Novel Use for Adipose Tissue", Tissue Engineering, vol. 9, No. 4, 2003.

Nehls, A. and D Drenckhahn 1991 *J. Cell Biol.* "Heterogeneity of Microvascular Pericytes for Smooth Muscle Type Alpha-Actin," 113:147-154.

Nerem, R.M. and Ensely, A.E. (2004) "The tissue engineering of blood vessels and the heart" Am J Transplant 4 Supp 6, 36-42.

Nguyen, A., K.A. Pasyk et al. (1990) "Comparative study of survival of autologous adipose tissue taken and transplanted by different techniques" Plast Reconstr Surg 85(3): 378-86; discussion 387-9.

Nishimori, M. Yamada, Y., Hoshi, K., Akiyama, Y., Hosi, Y., Morishima, Y., Tsuchida, M., Fukuhara, S., and Kodera,Y. (2002) "Health-related quality of life of unrelated bone marrow donors in Japan" Blood 99(6), 1995-2001.

Novakofski, Jan E., "Primary Cell Culture of Adipose Tissue," *Biology of the Adipocyte: Research Approaches*, Van Nostrand Reinhold Company, NY, 1987 160-97.

O'Driscoll, Shawn W., "Current Concepts Review: The Healing and Regeneration of Articular Cartilage," *Journal of Bone and Joint Surgery*, 1998, 80A:1795-812.

Odorico, J.S., Kaufman, D.S., and Thomson, J.A. (2001) "Multilineage differentiation from human embryonic stem cells lines" Stem Cells 19, 193-204.

Ohgushi, H. And Caplan, A.I. (1999) "Stem cell technology and bioceramics: from cell to gene engineering" J Biomed Mater Res 48, 913-27.

Olson, E. N. et al., "Know Your Neighbors: Three Phenotypes in Null Mutants of the Myogenic bHLH Gene MRF4," *Cell*, 1996, 85:1-4.

Ooi, K., M.P. Lacy et al (1991) "salt-soluble collagen and elastin in the human aorta and pulmonary artery" Exp Mol Pathol 55(1): 25-9.

Orlic, D., J. Kajstura, et al. (2001) "Bone marrow cells regenerate infarcted myocardium" Nature 410(6829): 701-5.

Orlic, D., J. Kajstura, et al. (2001) "Transplanted adult bone marrow cells repair myocardial infarcts in mice" Ann N Y Acad Sci 938: 221-9, discussion 229-30.

Owen, TA, et al., 1990 *J. Cell Physiol*. "Progressive Development of the Rat Osteoblast Phenotype in Vitro: Reciprocal Relationships in Expression of Genes Associated with Osteoblast Proliferation and Differentiation During Formation of the Bone Extracellular Matrix," 143:420-430.

Pairault, Jacques and Howard Green, "A study of the adipose conversion of suspended 3T3 cells by using glycerophosphate dehydrogenase as differentiation marker," *Proc. Natl. Acad. Sci. USA*, 1979, 76:5138-42.

Palma, P.C., C.L. Riccetto, et al. (1997) "Repeated lipoinjections for stress urinary incontinence" J Endourol 11(1): 67-70.

Park, S. R. et al., "Interconversion Potential of Clone Human Marrow Adipocytes In Vitro," *Bone*, 1999, 24:549-54.

Patrick et al. "Long-term implantation of preadipocyte-seeded PLGA scaffolds." Tissue Eng. 8(2):283-93 (2002).

Patrick et al. "Preadipocyte Seeded PLGA Scaffolds for Adipose Tissue Engineering." Tissue Eng. 5(2): 139-151 (1999).

Paul S.R., et al., 1991 *Blood* "Stromal Cell-Associated Hematopoiesis: Immortalization and Characterization of Primate Bone Marrow-Derived Stromal Cell Line," 77: 1723-33.

Pedersen, S. B. et al., "Identification of oestrogen receptors and oestrogen receptor mRNA in human adipose tissue," *European Journal of Clinical Investigation*, 26:262-9, 1996.

Pera, M.F., Reubinoff, B., and Trounson, A. (2000) "Human embryonic stem cells" J Cell Sci 113 (Pt 1) 5-10.

Periasamy, Muthu et al., "Regulation of myosin heavy-chain gene expression during skeletal-muscle hypertrophy," *Biochem. J.* 1989 257:691-698.

Perin et al. "Transendocardial, autologous bone marrow cell transplantation for severe, chronic ischemic heart failure." Circulation. 107(18):2294-2302 (2003).

Pettengell et al. "Peripheral Blood Progenitor Cell Transportation in Lymphoma and Leukemia Using a Single Apheresis." Blood. 82:3770-3777 (1993).

Pettersson, Per et al., "Adipocyte Precursor Cells in Obese and Nonobese Humans," *Metabolism*, 34:808-12, 1985.

Pettersson, Per et al., "Cells in Human Adipose Tissue Developing into Adipocytes," *Acta Med Scand*, 1984, 215:447-51.

Pierelli, Luca et al., "CD34+/CD105+ cells are enriched in primitive circulating progenitors residing in the G0 phase of the cell cycle and contain all bone marrow and cord blood CD34+/CD38low/-precursors," *British Journal of Haematology*, 2000, 108:610-20.

Piersma et al. "Migration of fibroblastoid stromal cells in murine blood." Cell Tissue Kinet. 18:589-595 (1985).

Pipp, F., Heil, M., Issbrucker, K., Ziegelhoeffer, T., Martin, S., Van den, H.J., Weich, H., Fernandez, B., Golumb, G., Carmeliet, P., Schaper, W., and Clauss, M. (2003) "VEGF-1-selective VEGF homologue PIGF is arteriogenic: evidence for a monocyte-mediated mechanism" Circ. Res 92, 378-385.

Pittenger, M.F., A.M. Mackay, et al. (1999) "Multilineage potential of adult human mesenchymal stem cells" Science 284(5411): 143-7.

Planat-Bernard, et al. "Plasticity of Human Adipose Lineage Cells toward Endothelial Cells Physiological and Therapeutic Perspectives." Circulation, American Heart Association. 109(5):656-663 (2004).

Planat-Benard et al. "Spontaneous Cardiomyocyte Differentiation from Adipose Tissue Stroma Cells." Circulation Research. 94(2):223-229 (2004).

Pollard, a. et al., "Controlled Conversion of an Immortalized Mesodermal progenitor Cell Towards osteogenic, Chondrogenic, or Adipogenic Pathways," *J. Cell Biol.* 1995 130;1461-1472.

Price, Paul A. and Sharon A. Baukol, "1,25-Dihydroxyvitamin D3 Increases Synthesis of the Vitamin K-dependent Bone Protein by Osteosarcoma Cells," *The Journal of Biological Chemistry*, 1980, 255:11660-3.

Price, Paul A. et al., "Matrix GLA Protein, A New γ-Carboxyglutamic Acid-Containing Protein Which is Associated With The Organic Matrix of Bone," *Biochem. Biophys. Res. Commun.*, 1983 117:765-771.

Price, Paul A., "GLA-Containing Proteins of Bone," *Connective Tissue Research*, 1989, 21:51-60.

Prince, H.M., Bashford, J., Wall, D., Rischin, D., Parker, N., Toner, G.C., Seymour, J.F., Blakey, D., Haylock, D., Simmons, P., Francis, P., Wolf, M., Januszewicz, E.H., Richardson, G., Scarlett, J., and Briggs, P. (2002) "Isolex 300i CD34-selected cells to support multiple cycles of high-dose therapy" Cytotherapy 4, 137-45.

Probst, M. et al., "Homologous bladder augmentation in dog with the bladder acellular matrix graft," *BJU International*, 2000, 85:362-71.

Prockop D.J. 1997 *Science* "Marrow Stromal Cells as Stem Cells for Nonhematopoietic Tissues," 276: 71-74.

Prockop, D.J., S.A. Azizi, et al. (2000) Potential use of marrow stromal cells as therapeutic vectors for diseases of the central nervous system: Prog Brain Res 128:293-7.

Puma, S.K. and M. Babu (2000) "Collagen based dressings—a review" Burns 26(1): 54-62.

Qian, X., Jin, L., and Lloyd, R.V. (1998) Percoll Density Gradient-Enriched Populations of Rat Pituitary Cells: Interleukin 6 Secretion, Proliferative Activity, and Nitric Oxide Synthase Expression: Endocr. Pathol. 9, 339-346.

Quirici, N., Soligo, D., Bossolasco, P., Servida, F., Lumini, C., and Deliliers, G.L. (2002) "Isolation of bone marrow mesenchymal stem cells by anti-nerve growth factor receptor antiobidies" Exp Hematol 30, 783-91.

Rajnoch, C., Chachques, J.C., Berrebi, A., Bruneval, P., Benoit, M.O., and Carpentier, A. (2001) "Cellular therapy reverses myocardial dysfunction" J Thorac Cardiovasc Surg 121(5), 871-8.

Ramsay, T. G. et al., "Pre-Adipocyte Proliferation and Differentiation in Response to Hormone Supplementation of Decapitated Fetal Pig Sera," *J. Anim. Sci.,* 64:735-44, 1987.

Rando, et al., 1995 *Exp. Cell Res.* "The Fate of Myoblasts Following Transportation into Mature Muscle," 220:383-389.

Rando, Thomas A. and Helen M. Blau, "Primary Mouse Myoblast Purification, Characterization, and Transplantation for Cell-mediated Gene Therapy," *J. Cell Biol* 1994 125:1275-1287.

Rangappa, S., Fen, C., Lee, E.H., Bongso, A., and Wei, E.S. (2003) "Transformation of adult mesenchymal stem cells isolated from the fatty tissue into cardiomyocytes" Ann Thorac. Surg 75, 775-779.

Rehman, et al. "Angiogenic potential of subcutaneous adipose stromal cells for autologous cell therapy." Journal of the American College of Cardiology. 41(6)(Suppl A): 308A (Mar. 19, 2003).

Rehman, et al. "Secretion of angiogenic and antiapoptotic factors by human adipose stromal cells." Circulation. 109(10):1292-1298 (2004).

Reinecke H et al. 2002. Skeletal muscle stem cells do not transdifferentiate into cardiomyocytes after cardiac grafting. J. Mol. Cell. Cardiol. 34: 241-249.

Remacle, M., G. Lawson et al (1999) "Correcting vocal fold immobility by autologous collagen injection for voice rehabilitation. A short-term study." Ann Otol Rhinol Laryngol 108(8): 788-83.

Remme, W.J. (2000) "Overview of the relationship between ischemia and congestive heart failure" Clin Cardiol 23, 4-8.

Reyes, M., Lund, T., Lenvik, T., Aguiar, D., Koodie, L., and Verfaillie, C.M. (2001) "Purification and ex vivo expansion of postnatal human marrow mesodermal progenitor cells" Blood 98, 2615-2625.

Richardson, J. B. et al., "Repair of human articular cartilage after implantation of autologous chondrocytes," *The Journal of Bone and Joint Surgery*, 1999, 81:1064-8 ).

Rickard, David J. et al., "Isolation and Characterization of Osteoblast Precursor Cells from Human Bone Marrow," *Journal of Bone and Mineral Research*, 1996, 11:312-24.

Rodriguez et al. "The human adipose tissue is a source of multipotent stem cells." Biochimie. 87(1):125-128 (2005).

Rubens, F. D. et al., "Tissue Factor Expression by Cells Used for Sodding of Prosthetic Vascular Grafts," *Journal of Surgical Research*, 72:22-8, 1997.

Russell, S.W., Doe, W.F., Hoskins, R.G. and Cochrane, C.G. (1976) "Inflammatory cells in solid murine neoplasms. I. Tumor disaggregation and identification of constituent inflammatory cells" Int J Cancer 18, 322-30.

Seelbach, A., et al., 1997 *Cell and Tiss. Res.* "The Fibroblast-specific MAb AS02: a novel tool for detection and elimination of human fibroblasts," 290:593-599.

Safford et al. "In vivo engraftment and differentiation of murine adipose derived stromal cells" Blood, vol. 100, No. 11, 731a, (Nov. 2002).

Safford, Kristine M. et al., "Neurogenic differentiation of murine and human adipose-derived stromal cells," *Biochemical and Biophysical Research Communications*, 2002, 371-379.

Saito et al. "Transcoronary implantation of bone marrow stromal cells ameliorates cardiac function after myorcardial infarction." The Journal of Thoracic and Cardiovascular Surgery. 126(1):114-122 (2003).

Sanchez-Ramos, et al., 2000 "Adult Bone Marrow Stromal Cells Differentiate into Neural Cells in Vitro," Exp. Neurol. 164:247-256.

Sarnat, Harvey B. et al., "Neuronal nuclear antigen (NeuN): a marker of neuronal maturation in the early human fetal nervous system," *Brain & Development*, 1998, 20:88-94.

Sattler et al. "Liporecycling: a technique for facial rejuvination and body contouring" Dermantol. Surg. vol. 26, No. 12, 1140-1144 (Dec. 2000).

Savitz et al. "Cell Transplantation for stroke." Annals of Neurology. 52(3):266-275 (2002).

Scherberich, A. and A. Beretz (2000) "Culture of vascular cells in tridimensional (3-D) collagen: a methodological review" Therapie 55(1): 35-41.

Schoeller et al. "Histomorphologic and volumetric analysis of implanted autologous preadipocyte cultures suspended in fibrin glue: a potential new source for tissue augmentation." Aesthetic Plastic Surgery. 25(1):57-63 (2001).

Scholz, D., Cai, W.J., and Schaper, W. (2001) "Arteriogenesis, a new concept of vascular adaptation in occlusive disease" Angiogenesis 4, 247-257.

Scholz, D., Elasaesser, H., Sauer, A., Friedrich, C., Luttun, A., Carmeliet, P., and Schaper, W. (2003) "Bone marrow transplantation abolishes inhibition of arteriogenesis in placenta growth factor (PlGF)—mice" J Mol Cell Cardiol 35, 177-184.

Scholz,D., Ziegelhoeffer, T., Helisch, A., Wagner, S., Friedrich, C., Podzuweit, T. And Schaper, W. (2002) "Contribution of arteriogenesis and angiogenesis to postocculsive hindlimb perfusion in mice" J Mol Cell Cardiol 34, 775-787.

Schwartz, R.E., Reyes, M., Koodie, L., Jiang, Y., Blackstad, M., Lund, T., Lenvik, T., Johnson, S., Hu, W.S. and Verfaillie, C.M. (2002) "Multipotent adult progenitor cells from bone marrow differentiate into functional hepatocyte-like cells" J Clin Invest 109, 1291-302.

Schwartzmann, M. (2000) "Use of collagen membranes for guided bone regeneration: a review" Implant Dent 9(1): 63-6.

Schweitzer, C.M., Van Der, Schoot, Ce, Drager, A.M., Van der Valk, P., Zevenbergen, A., Hooibrink, B., Westra, A.H., and Langenhuijsen, M.M. (1995) "Isolation and culture of human bone marrow endothelial cells" Exp Hematol 23, 41-8.

Sclafani, A.P. and T. Romo, 3rd (2001) "Collagen, human collagen and fat: the search for a three-dimensional soft tissue filler" Facial Plast Surg 17(1): 79-85.

Sclafani, A.P., T. Romo, 3rd et al. (2002) "Rejuvenation of the aging lip with an injectable acellular dermal graft (cymetra)" Arch Facial Plast Surg 4(4): 252-7.

Scott, Douglas M. et al., "Collagen Synthesis in Cultured Osteoblast-like Cells," *Archives of Biochemistry and Biophysics*, 1980, 201:384-91.

Seale and Rudnicki 2000 *Dev. Biol.* "A New Look at the Origin, Function, and "Stem-Cell" Status of Muscle Satellite Cells," 218:115-124.

Sekiya, I., Larson, B.L., Smith, J.R., Pochampally, R., Cui, J.G., and Prockop, D.J. (2002) "Expansion of human adult stem cells from bone marrow stroma: conditions that maximize the yields of early progenitors and evaluate their quality" Stem Cells 20, 530-541.

Sergeant, P., Blackstone, E., and Meyns, B. (1997) "Early and late outcome after CABG in patients with evolving myocardial infarction" Eur J Cardiothorac. Surg 11, 848-856.

Shalhoub, Victoria et al., "Downregulation of Cell Growth and Cell Cycle Regulated Genes during Chick Osteoblast Differentiation with the Reciprocal Expression of Histone Gene Variants," *Biochemistry*, 1989, 28:5318-22.

Shi, Q., S. Rafil, et al. (1998) "Evidence for circulating bone marrow-derived endothelial cells" Blood 92(2): 362-7.

Shigematsu, S., Yamauchi, K., Nakajima, K., Iijima, S., Aizawa, T., and Hashizume, K. (1999) "IGF-1 regulates migration and angiogenesis of human endothelial cells" Endocr. J 46 Suppl, S59-S62.

Shillabeer, et al., "A novel method for studying preadipocyte differentiation in vitro," *Intl. J. Obesity* 1996 20(Supp. 3), S77-S83.

Shore, J.W. (2000) "Injectable lyophilized particulate human fascia lata (Fascian) for lip, perioral and glabellar enhancement" Opthal Plast Reconstr Surg 16(1): 23-7.

Shukunami C., et. al., 1996 *Journ. of Cell Bio.* "Chrondrogenic Differentiation of Clonal Mouse Embryonic Cell Line ATDC5 In Vitro: Differentiation-dependent Gene Expression of Parathyroid Hormone (PTH)/PTH-related Peptide Receptor," 133:2:457-468.

Shukunami, C., et al., 1998 *Exp. Cell Res.* "Sequential Progression of the Differentiation Program by Bone Morphogenetic Protein-2 in Chondrogenic Cell Line ATDC5," 241:1-11.

Siffert, Robert S., "The Role of Alkaline Phosphatase in Osteogenesis," *The Journal of Experimental Medicine*, 1951, 93:415-26.

Silberstein, L., et al., 1986 *Cell* "Developmental Progression of Myosin Gene Expression in Cultured Muscle Cells," 46:1075-1081.

Silver, F.H. and G. Pins (1992) "Cell growth on collagen: a review of tissue engineering using scaffolds containing extracellular matrix" J Long Term Eff Med Implants 2(1): 67-80.

Sivan-Loukianova et al. "CD34+ Blood cells accelerate vascularization and healing of diabetic mouse skin wounds" J. Vascular Research, vol. 40, No. 4, 368-377 (Jul.-Aug. 2003).

Šmahel, J., "Aspiration lipectomy and adipose tissue injection: pathophysiologic commentary," *European Journal of Plastic Surgery*, 14:126-31, 1991.

Smith et al., 2000, "Mesenchymal Stem Cells Derived From Bone Marrow and Human Adipose Tissue Exhibit Multilineage Potential," *Journal of Investigative Medicine*, 95A.

Smith, J.W. (1997) "Apheresis techniques and cellular immunomodulation" Ther. Apher. 1, 203-206.

Smith, R.J. and Sweetenham, J.W. (1995) "A mononuclear cell dose of 3×10(8)/kg predicts early multilineage recovery in patients with malignant lymphoma treated with carmustine, etoposide, Ara-C and melphalan (BEAM) and peripheral blood progenitor cell transplantation" Exp Hematol 23, 1581-8.

Smits, G., Holzgreve, W., and Hahn, S. (2000) "An examination of different Percoll density gradients and magnetic activated cell sorting (MACS) for the enrichment of fetal erythroblasts from maternal blood" Arch. Cynecol. Obstet. 263, 160-163.

Soda, et al., 1983, "Adipocyte stem cell: A brief review," *Int. J. of Cell Cloning*, 1:79-84.

Sodian, R., Lemke, T., Fritsche, C., Hoerstrup, S.P, Fu, P., Potapov, E.V., Hausmann, H., and Hetzer, R. (2002) "Tissue-engineering bioreactors: a new combined cell-seeding and perfusion system for vascular tissue engineering" Tissue Eng 8, 863-870.

Soli, M., Blanco, L., Riggert, J., Martinez, Clavel, A., Lucas, C., Lunghi, M., Belloni, M., Wolf, C., van Waeg, G., and Antoon, M. (2001) "A multicentre evaluation of a new filtration protocol for leucocyte depletion of high-haematocrit red blood cells collected by an utomated blood collection system" Vox Sang. 81, 108-112.

Sorisky et al., "From preadipocyte to Adipocyte: Differentiation-Directed Signals of Insulin from the Cell Surface to the Nucleus," *Critical Review in Clinical Laboratory Sciences* 1999 36(1), 1-34.

Speranza, M.L. and G. Valentini (1986) "A simple procedure for the purification of neutral salt soluble type I collagen from skin" Ital J Biochem 35(1): 42-8.

Springhorn, Jeremy P. et al., "Human Capillary Endothelial Cells from Abdominal Wall Adipose Tissue: Isolation Using an Anti-Pecam Antibody," *In Vitro Cellular & Developmental Biology-Animal*, 31:473-81, 1995.

Stamm, C., Westphal, B., Kleine, H.D., Petzsch, M., Kittner, C., Klinge, H., Schumichen, C., Nienaber, C.A., Freund, M. and Steinhoffm G. (2003) "Autologous bone-marrow stem-cell transplantation for myocardial regeneration" Lancet 4, 45-46.

Stashower et al., 1999, "Stromal progenitor cells present within liposuction and reduction abdominoplasty fat for autologous transfer to aged skin," *Dermatologic Surgery*, 25:12:945-949.

Stosich et al. "Adipose tissue engineering from human adult stem cells: clinical implications in plastic and reconstructive surgery." Plast Reconstr Surg 119, 71-83 (2007).

Strauer, B.E., M. Brehm, et al. (2002) "Repair of infarcted myocardium by autologous intracoronary mononuclear bone marrow cell transplantation in humans" Circulation 106(15): 1913-8.

Strutt et al., 1996, "Growth and differentiation of human adipose stromal cells in culture," *methods in Molecular Medicine: Human Cell Culture Protools*, 41-51.

Suga, S., et al., 1996,"*Eur. J. Cell Biol.*" Intracellular localization of antigens recognized by anti-vimentin monoclonal antibodies (mAbs): Cross-reactivities of anti-vimentin mAbs with other cellular components 70:84-91.

Sundberg, C., Kowanetz, M., Brown, L.F., Detmar, M., and Dvorak, H.F. (2002) "Stable expression of antiopoietin-1 and other markers by cultured pericytes: phenotypic similarities to a subpopulation of cells in maturing vessels during later stages of angiogenesis in vivo" Lab invest 82, 387-401.

Syrjälä, M. et al., "A flow cytometric assay of CD34-postitive cell populations in the bone marrow," *British Journal of Haematology*, 1994, 88:679-84.

Tabata,Y. et al. "De novo formation of adipose tissue by controlled release of basic fibroblast growth factor." *Tissue Eng.* 6:6279-289 (2000).

Tacchetti, C, et al., 1992 *Exp Cell Res.* "Cell Condensation in Chondrogenic Differentiation," 200:26-33.

Tacchetti, C. et al., "In Vitro Morphogenesis of Chick Embryo Hypertrophic Cartilage," *The Journal of Cell Biology*, 1987, 105:999-1006.

Takasaki, et al (1995) "Human type VI collagen: purification from human subcutaneous fat tissue and an immunohistochemical study of morphea and systemic sclerosis" J Dermatol 22(7): 480-5.

Takahashi, T., C. Kalka, et al. (1999) "Ischemia and cytokine-induced mobilization of bone marrow-derived endothelial progentiro cells for neovascularization" Nat Med 5(4): 434-8.

Tapscott, et al., 1988 *Science* "MyoD1: A Nuclear Phosphoprotein Requiring a Myc Homology Region to Convert Fibroblasts to Myoblasts," 242:405-411.

Tavassoli et al., 1981, "The Nature of Fibroblasts Derived From Adipose Tissue In-Vitro," *Clinical Research*, 29:5:871A.

Tavassoli, Mehdi, "In Vivo Development of Adipose Tissue Following Implantation of Lipid-Depleted Cultured Adipocyte," *Experimental Cell Research*, 137:55-62, 1982.

Thomas, E.D. (1994) "Stem Cell Transplantation: Past, Present and Future" Stem Cells 12: 539-544.

Thornell, et al., 1984 *J. Neurol. Sci.* "Development of Fiber Types in Human Fetal Muscle," 66:107-115.

Toma, J.G., Akhavan, M., Fernandes, K.J., Barnabe-Heider, F., Sadikot, A., Kaplan, D.R. and Miller, F.D. (2001) "Isolation of multipotent adult stem cells from the dermis of mammalian skin" Nat Cell Biol 3, 778-84.2.

Tontonoz, Peter et al., "mPPARg2: tissue-specific regulator of an adipocyte enhancer," *Genes & Development*, 1994, 8:1224-34.

Torio-Padron et al. "Engineering of adipose tissue by injection of human preadipocytes in fibrin." Aesthetic Plast Surg 31, 285-293 (2007)[3].

Tosh, et al. "Conversion of pancreatic cells to hepatocytes." Biochem Soc Trans 30:51-55 (2002).

Totonoz, et al., 1995 *Nucl. Acid Res* "mPPARg2: tissue-specific regulator of an adipocyte enhancer."

Trayhurn, P. and Margaret Ashwell, "Control of white and brown adipose tissues by the autonomic nervous system," *The Proceedings of the Nutrition Society*, 1987, 46:135-42.

Tsonis and Goetinck 1990 *Exp. Cell Res.* "Cell Density Dependent Effect of a Tumor Promoter on Proliferation and Chondrogenesis of Limb Bud Mesenchymal Cells," 190:247-253.

Twentyman, P.R. And Yuhas, J.M. (1980) "Use of bacterial neutral protease for disaggregation of mouse tumours and multicellular tumor spheroids" Cancer Lett 9, 225-8.

Uitto, J. (1971) "Collagen biosynthesis in human skin. A review with emphasis on scleroderma" Ann Clin Res 3(5): 250-8.

Urban et al. "Degeneration of the intervertebral disc." Arthritis Research & Therapy. 5(3):120-130 (2003).

Urbich et al. "Endothelial Progenitor Cells." Trends in Cardiovascular Medicine. 14(8):318-322 (2004).

Van et al., 1978, "Complete Differentiation of Adipocyte Precursors," *Cell Tissue*, 195:317-329.

Van Merris, V., Meyer, E., Dosogne, H., and Burvenich, C. (2001) "Separation of bovine bone marrow into maturation-related myeloid cell fractions" Vet. Immunol. Immunopathol. 83, 11-17.

Vandenburgh, Herman H. and Patricia Karlisch, "Longitudinal Growth of Skeletal Myotubes In Vitro in a New Horizontal Mechanical Cell Stimulator," *In Vitro Cellular & Developmental Biology*, 1989, 25:607-16.

Vassaux, et al., "Proliferation and differentiation of Rat Adipose Precursor Cells in Chemically Defined Medium: Differential Action of Anti-Adipogenic Agents," *Journal of Cellular Physiology* 1994 161(2), 249-256.

von der Mark, et al., 1977 *Nature* "Relationship between cell shape and type of collagen synthesised as chondrocytes lose their cartilage phenotype in culture," 267:531-532.

von Heimburg, D. et al. "Human preadipocytes seeded on freeze-dried collagen scaffolds investigated in vitro and in vivo." *Biomaterials* 22, 429-38 (2001).

Vukicevic et al., 1992 *Exp. Cell Res* "Identification of Multiple Active Growth factors in Basement Membrane Matrigel Suggests Caution in Interpretation of Cellular Activity Related to Extracellular Matrix Components,", 202(1), 1-8.

Wabitsch, et al., "Biological Effects of Human Growth Hormone in Rat Adipocyte Precursor Cells and Newly Differentiated Adipocytes in primary Culture," *Metabolism* 1996 vol. 45,No. 1 pp. 34-42.

Wakitani, Shigeyuki et al., "Mesenchymal Cell-Based Repair of Large, Full-Thickness Defects of Articular Cartilage," *The Journal of Bone and Joint Surgery*, 1994, 76A:579-92.

Wakitani, Shigeyuki et al., "Myogenic Cells Derived from Rat Bone Marrow Mesenchymal Stem Cells Exposed to 5-Azacytidine," *Muscle & Nerve*, 1995, 18:1417-26.

Walther, W. and Stein, U. (2000) Viral vectors for gene transfer: a review of their use in the treatment of human diseases: Drugs 609, 249-71.

Walton et al. "De novo adipose formation in a vascularized engineered construct." *Microsurgery* 24, 378-384 (2004).

Wang, L., Zeng, H., Wang, P., Soker, S., and Mukhopadhyay, D. (2003) "Neuropilin-1 mediated vascular permeability factor/vascular endothelial growth factor-dependent endothelial cell migration" J Biol Chem 278, 48848-48860.

Watts, M.J., Somervaille, T.C., Ings, S.J., Ahmed, F., Khwaja, A., Yong, K. and Linch, D.C. (2002) "Variable product purity and functional capacity after CD34 selection: a direct comparison of the CliniMACS (v2.1) and Isolex 300i(v2.5) clinical scale devices" Br J Haematol 118, 117-23.

Weiner, Francis R. et al. "Regulation of collagen Gene Expression in 3T3-L1 Cells. Effects of Adipocyte Differentiation and Tumor necrosis Factor a," Biochem 1989 28:4094-4099.

Weintraub, et al., 1991 *Science* "The myoD Gene Family: Nodal Point During Specification of the Muscle Cell Lineage," 251:761-766.

Weintraub, Harold et al. "Tissue-specific gene activation by MyoD: determination of specificity by *cis*-acting repression elements," *Genes & Development*, 1994, 8:2203-11.

Werlich, T., K.J. Stiller, et al. (1999) "Experimental studies on the stem cell concept of liver regeneration II" Exp Toxicol Pathol 51(1): 93-8.

Williams, Irene H. and S. Efthimios Polakis, "Differentiation of 3T3-L1 Fibroblasts to Adipocytes, the Effect of Indomethacin, Prostaglandin $E_1$ and Cyclic AMP on the Process of Differentiation" *Biochem Biophys. Res.Commun.* 1977 77:175-186.

Williams, John T. et al., "Cells Isolated from Adult Human Skeletal Muscle Capable of Differentiating into Multiple Mesodermal Phenotypes," *The American Surgeon*, 65:22-6, 1999.

Williams, S.K., McKenney, S. and Jarrell, B.E. (1995) "Collagenase lot selection and purification for adipose tissue digestion" Cell Transplant 4, 281-9.

Williams, Stuart K. et al., "Liposuction-derived human fat used for vascular graft sodding contains endothelial cells and not mesothelial cells as the major cell type," *Journal of Vascular Surgery*, 19:916-23, 1994.

Wise, Leigh S. and Howard Green, "Participation of One Isozyme of Cytosolic Glycerophosphate Dehydrogenase in the Adipose Conversion of 3T3 Cells," *J. Biol. Chem.* 1979 254:273-275.

Wlodarski, Krzysztof H., "Section III. Basic Science and Pathology. Properties and Origin of Osteoblasts," *Clinical Orthopaedics and Related Research*, 252:276-93, 1990.

Wollert et al. "Intracoronary autologous bone-marrow cell transfer after myocardial infarction: the BOOST randomised controlled clinical trial." The Lancet Limited. 364(9429):141-148 (2004).

Woodbury, et al., 2000 *J. Neurosci. Res. Science* "Adult Rat and Human Bone Marrow Stromal cells Differentiate Into Neurons," 61:364-370 Young, 2000 *Science* "A Time for Restraint," 287:1424.

Wu et al. "Preparation and assessment of glutaraldehyde-crosslinked collagen-chitosan hydrogels for adipose tissue engineering." *J Biomed Mater Res A* 81, 59-65 (2007).

Xiong, B., Gong, L.L., Zhang, F., Hu, M.B. and Yuan, H.Y. (2002) "TGF beta1 expression and angiogenesis in colorectal cancer tissue" World J Gastroenterol. 8, 496-498.

Yavorkovsky, L., E. Lai, et al. (1995) "Participation of small intraportal stem cells in the restitutive response of the liver to periportal necrosis induced by allyl alochol" Hepatology 21(6): 1702-12.

Ye, Q., Zund, G., Benedikt, P., Jockenhoevel, S., Hoerstrup, S.P., Sakyama, S., Hubbell, J.A. and Turina, M. (2000) "Fibrin gel a three dimensional matrix in cardiovascular tissue engineering" Eur J Cardiothorac Surg 17, 587-91.

Yin, L., D. Lynch, et al. (1999) "Participation of different cell types in the restitutive response of the rat liver to periportal injury induced by allyl alcohol" J Hepatol 31(3): 497-507.

Yokoyama, T., N. Yoshimural et al (2001) "Persistence and survival of autologous muscle derived cells versus bovine collagen as potential treatment of stress urinary incontinence" J Urol 165(1): 271-6.

Yoo, Jung U. and Brian Johnstone, "The Role of Osteochondral Progenitor Cells in Fracture Repair," *Clinical Orthopaedics and Related Research*, 1998, 355S:S73-81 ).

Yoon, Kyonggeun et al., "Characterization of the Rat osteocalcin Gene: Stimulation of Promoter Activity by 1,25-Dihydroxyvitamin D3," *Biochem.* 1988 27:8521-8526.

Young, "A Time for Restraint", 2000 Science 287:1424.

Young et al., "Mesenchymal Stem Cells Reside Within the Connective Tissues of Many Organs," *Developmental Dynamics* 1995 202(2), 137-144.

Young, H.E., Steele, T.A., Bray, R.A., Hudson, J., Floyd, J.A., Hawkins, K., Thomas K., Austin, T., Edwards, C. Cuzzourt, J., Duenzl, M., Lucas, P.A., and Black, A.C., Jr. (2001) "Human reserve pluripotent mesenchymal stem cells are present in the connective tissues of skeletal muscle and dermis derived from fetal, adult and geriatric donors" Anat Rec 264, 51-62.

Young, Henry E. et al., "Human Pluripotent and Progenitor Cells Display Cell Surface Cluster Differentiation Markers CD10, CD13, CD56, and MHC Class-I," *Proc. Soc. Exp. Biol. Med.*, 1999, 221:63-71.

Zalin, RJ 1987 *Exp. Cell Res.* "The Role of Hormones and Prostanoids in the in Vitro Proliferation and differentiation of Human Myoblasts," 172:265-281.

Zezulak, Kathleen M. and Howard Green, "Specificity of Gene Expression in Adipocytes," *Molecular and Cellular Biology*, 1985, 5:419-21.

Zimmerman, W.H., Diddie, N., Wasmeier, G.H. Nixdorff, U., Hess, A., Meinychenko, I., Boy, O., Neuhuber, W.L., Weyand, M., and Eschenhagen, T. (2002) "Cardiac grafting of engineered heart tissue in syngenic rats" Circulation 106, 1151-1157.

Zimmermann, W.H., Melnychenko, I., and Eschenhagen, T. (2004) "Engineered heart tisue for regeneration of diseased hearts" Biomaterials 25, 1639-1647.

Zohar, R. et al., "Analysis of intracellular osteopontin as a marker of osteoblastic cell differentiation and mesenchymal cell migration," *European Journal of Oral Sciences*, 1998, 106(Supp. 1):401-7.

Zuk, Patricia A. et al., "Human Adipose Tissue Is A Source of Multipotent Stem Cells," *Molecular Biology of the Cell*, 2002, 13:4279-4295.

Zuk, Patricia Z. et al., "Multilineage Cells from Human Adipose Tissue: Implication for Cell-Based Therapies," *Tissue Engineering*, Apr. 2001, 7:211-28.

Zvaifler, et al., 2000, "Mesenchymal precursor cells in the blood of normal individuals," *Arthritis Res.* 2:477-488.

Supplemental European Search Report for European Patent Application No. EP 02805648 dated Sep. 5, 2006.

International Search Report for International Patent Application No. PCT/US02/29207 dated Dec. 17, 2002.
International Search Report for International Patent Application No. PCT/US02/39465 dated Jun. 22, 2006.
International Search Report for International Patent Application No. PCT/US02/40921dated Jul. 30, 2003.
International Search Report for International Patent Application No. PCT/US04/20594 dated Apr. 6, 2005.
International Search Report for International Patent Application No. PCT/US04/21391 dated Apr. 4, 2005.
International Preliminary Report on Patentability for PCT/US04/21415 dated Jan. 18, 2007, containing Written Opinion dated Dec. 30, 2005.
International Search Report for International Patent Application No. PCT/US04/21417 dated Apr. 12, 2005.
International Search Report for International Patent Application No. PCT/US04/21418 dated Dec. 22, 2005.
International Search Report for International Patent Application No. PCT/US04/21480 dated Apr. 4, 2005.
International Preliminary Report on Patentability for International Patent Application No. PCT/US04/21483 dated Jan. 18, 2007, containing Written Opinion dated Apr. 13, 2006.
International Preliminary Report on Patentability for International Patent Application No. PCT/US04/21549 dated Jan. 18, 2007, containing Written Opinion dated Feb. 7, 2006.
International Search Report for International Patent Application No. PCT/US2004/005117 dated Apr. 6, 2006.
Supplemental Partial European Search Report for European Patent Application No. 2805565.5 dated Mar. 6, 2007.
Supplemental European Search Report for European Patent Application No. 4777155.5 dated Aug. 4, 2006.
Examination Report for European Patent Application No. 4756641.9 dated Jan. 19, 2007.
Supplemental European Search Report for European Patent Application No. 4756641.9 dated Oct. 18, 2006.
International Search Report for International Patent Application No. PCT/US2006/021017 dated Oct. 20, 2006.
International Search Report for International Patent Application No. PCT/US2006/040221 dated Feb. 27, 2007.
International Search Report for International Patent Application No. PCT/US2005/001267 dated Apr. 28, 2006.
Supplemental Partial European Search Report for European Patent Application No. 04777586.1 dated Jun. 5, 2007.
Supplemental European Search Report for European Patent Application No. 2805565.5 dated Jul. 4, 2007.
International Search Report for International Patent Application No. PCT/US2005/046296 dated Jun. 26, 2007.
Supplemental European Search Report for European Patent Application No. 4777586.1 dated Aug. 3, 2007.
Supplemental European Search Report for European Patent Application No. 04713403.6 dated Jul. 11, 2007.
Supplemental European Search Report for European Patent Application No. 04756623.7 dated Oct. 10, 2007.
Supplemental European Search Report for European Patent Application No. 04756607.0 dated Nov. 14, 2007.
European Search Report for European Application No. 07124088.1 dated Apr. 25, 2008.
International Search Report for International Application No. PCT/US05/18605 dated Jul. 3, 2008.
International Search Report for International Application No. PCT/US04/21419 dated Jul. 3, 2008.
Supplemental European Search Report for European Application No. 04777546.5 dated Jun. 10, 2009.
Supplemental European Search Report for European Application No. 04756626.0 dated Sep. 2, 2009.
Supplemental European Search Report for European Application No. 04776784.3 dated Nov. 5, 2009.
Supplemental European Search Report for European Application No. 05754073.4 dated Aug. 7, 2009.
Bianco et al., Apr. 2008, Mesenchymal stem cells: revisiting history, concepts, and assays, Cell Stem Cell, 2:313-319.

Casteilla et al., Apr. 26, 2011, Adipose-derived stromal cells: their identity and uses in clinical trials, an update, World J. Stem Cells, 3(4):25-33.
Fraser et al. "Adult Stem Cell Therapy for the Heart." The International Journal of Biochemistry & Cell Biology. 36(4):658-666 (2004).
Hauner et al. "Cultures of Human Adipose Precursor Cells." Methods in Molecular Biology. 155(1):239-247 (2001).
Horwitz et al., 2005, Clarification of the nomenclature for MSC: The International Society for Cellular Therapy position statement, 7(5):393-395.
Luttun et al. (2002) "Revascularization of ischemic tissues by PIGF treatment, and inhibition of tumor angiogenesis, arthritis and atherosclerosis by anti-Fltl" Nat Med 8, 831-40.
Mohr et al. (2001) "Simultaneous immunomagnetic CD34+ cell selection and B-cell depletion in peripheral blood progenitor cell samples of patients suffering from B-cell non-Hodgkin's lymphoma" Clin Cancer Res 7, 51-57.
Sommer et al. "Current Concepts of Fat Graft Survival: Histology of Aspirated Adipose Tissue and Review of the Literature." Dermatologic Surgery. 26(12):1159-1166 (2000).
Partial European Search Report for European Application No. 10183850.6 dated Jun. 17, 2011.
European Search Report for European Application No. 10184623.6 dated May 26, 2011.
Extended European Search Report for European Application No. 10183690.6 dated Aug. 22, 2011.
Extended European Search Report for European Application No. 10183737.5 dated Aug. 22, 2011.
Abbate, A., Biondi-Zoccai, G.G. and Baldi, A. (2002) "Pathophysiologic role of myocardial apoptosis in post-infarction left ventricular remodeling" J Cell Physiol 193, 145-53.
Aharinejad, S., Mars, S.C., Jr., Bock P., Mason-Savas, A., MacKay, C.A. Larson, E.K., Jackson, M.E., Luftensteiner, M. and Weisbauer, E. (1995) "CSF-1 treatment promotes angiogenesis in the metaphysics of osteopetrotic (toothless, tl) rats" Bone 16, 315-324.
Ahrens, Patricia Buckley et al., "Stage-Related Capacity for Limb Chondrogenesis in Cell Culture," *Developmental Biology*, 1977, 60:69-82.
Ailhaud, et al., 1983, "Hormonal requirements for growth and differentiation of OB17 preadipocyte cells in vitro," *Diabete & Metabolisme*, vol. 9:125-133.
Ailhaud, et al., 1985, "Lipoprotiene lipase et differenciation adipocytaire," *Reprod. Nutr. Develop.*, vol. 25:153-158.
Alameddine, Hala S. et al., "Regeneration of Skeletal Muscle Fibers from Autologous Satellite Cells Multiplied In Vitro. An Experimental Model for Testing Cultured Cell Myogenicity," *Muscle & Nerve*, 1989, 12:544-55.
Alhadlaq et al. "Engineered adipose tissue from human mesenchymal stem cells maintains predefined shape and dimension: implications in soft tissue augmentation and reconstruction." *Tissue Eng* 11, 556-566 (2005).
Angele, P. et al., "Engineering of Osteochondral Tissue with Bone Marrow Mesenchymal Progenitor Cells in a Derivatized Hyaluronan-Gelatin Composite Sponge,"*Tissue Engineering*, 1999, 5:545-53.
Ankrom, Michael A., "Age-related changes in human oestrogen function and levels in osteoblasts," *Biochem J.* 333:787-794, 1998.
Aragona, F. L. D'Urso et al (1998) "Immunologic aspects of bovine injectable collagen in humans. A review" Eur Urol 33(2): 129-33.
Arvidsson, A., Collin, T., Kirik, D., Kokaia, Z., and Lindvall, O. (2002) "Neuronal replacement from endogenous precursors in the adult brain after stroke" Nat Med 8, 963-70.
Ashjian, P.H. Elbarbary, A.S., Edmonds, B., DeUgarte, D., Zhu, M., Zuk, P.A., Lorenz, H.P., Benhaim, P., and Hedrick, M.H. (2003). "In vitro differentiation of human processed lipoaspirate cells into early neural progenitors" Plast Reconstr Surg 111 1922-31.

Asken, S. (1990) "Microliposuction and autologous fat transplantation for aesthetic enhancement of the aging face" J Dermatol Surg Oncol 16(10): 965-72.

Aso, Hisashi, et al., "A Preadipocyte Clonal Line from bovine Intramuscular Adipose Tissue: Nonexpression of GLUT-4 protein during Adipocyte Differentiation," *Biochem. Biophys. Res. Commun.* 213:369-375.

Asou, Y., Rittling, S.R., Yoshitake, H., Tsuji, K., Shinomiya, K., Nifuji, A., Denhardt, D.T., and Noda, M. (2001) "Osteopontin facilitates angiogenesis, accumulation of osteoclasts, and resorption in ectopic bone" Endocrinology 142, 1325-1332.

Assady, S., Maor, G., Amit, M., Itskovitz-Eldor, J., Skorecki, K.L., and Tzukerman, M. (2001) "Insulin production by human embryonic stem cells" Diabetes 50, 1691-7.

Assmus, B., Schachinger, V., Teupe, C., Britten, M., Lehmann, R., Dobert, N., Grunwald, F., Aicher, A., Urbich, C., Martin, H., Hoelzer, D., Dimeler, S., and Zeiher, A.M. (2002) Transplantation of Progenitor Cells and Regeneration Enhancement in Acute Myocardial Infarction (TOPCARE-AMI) Circulation 106, 3009-17.

\* cited by examiner

METHODS OF MAKING ENHANCED, AUTOLOGOUS FAT GRAFTS

CROSS-REFERENCE TO RELATED APPLICATIONS

This application is a continuation of, and claims priority under 35 U.S.C. §120, to U.S. patent application Ser. No. 12/886,353, filed Sep. 20, 2010, and this application is a continuation of, and claims priority under 35 U.S.C. §120, to U.S. patent application Ser. No. 10/614,648, filed Jul. 7, 2003, which is a divisional of U.S. application Ser. No. 10/316,127, filed Dec. 9, 2002. The aforementioned patent applications are hereby expressly incorporated by reference in their entireties.

BACKGROUND OF THE INVENTION

1. Field of the Invention

This invention generally relates to cells derived from adipose tissue, and more particularly, to adipo-derived stem cells, methods of using adipo-derived stem cells, compositions containing adipo-derived stem cells, and systems for preparing and using adipo-derived stem cells.

2. Description of the Related Art

Regenerative medicine can be defined as harnessing the body's regenerative mechanisms in a clinically targeted manner, using them in ways that are not part of the normal healing mechanism or by artificially amplifying normal mechanisms. One classic example of this process is found in bone marrow transplantation where hematopoietic stem and progenitor cells are harvested from a donor and placed into a recipient in whom the normal hematopoietic regenerative mechanisms have been ablated or substantially depleted or impaired, thereby replacing or regenerating the blood-forming capacity of the recipient (Thomas 1994). In recent clinical and pre-clinical studies this approach has been extended to the non-hematopoietic stem cell component of bone marrow with studies regenerating (or attempting to regenerate) tissues including bone (Connolly 1998; Horwitz, Prockop et al. 1999; Horwitz, Prockop et al. 2001), heart (Fukuda 2001; Orlic, Kajstura et al. 2001; Orlic, Kajstura et al. 2001; Strauer, Brehm et al. 2002), and liver (Avital, Inderbitzin et al. 2001). These studies have been based on the detection of the presence of non-hematopoietic stem cells and endothelial precursor cells in bone marrow (Prockop, Azizi et al. 2000) (Pittenger, Mackay et al. 1999) (Shi, Rafii et al. 1998; Carmeliet and Luttun 2001).

These studies used bone marrow transplant recipient animals in which donor and host cells could be distinguished by genetic markers to show that some fraction of new blood vessel development in the recipients was derived from the donor marrow cells (Carmeliet and Luttun 2001) (Takahashi, Kalka et al. 1999; Murayama, Tepper et al. 2002). While this work definitively demonstrates that marrow contains such cells it has generally been extended to mean that marrow is therefore the only tissue that contains relevant numbers of such cells to the extent that when an investigator detects endothelial precursor cells (EPCs) or marrow stem cells (MSCs) in the circulation it is automatically assumed that these cells are necessarily marrow-derived. Thus, the concept that cell populations from other tissues might represent an alternative or perhaps superior source of therapeutically relevant cell populations is not addressed.

It has been demonstrated that adipose tissue contains a population multipotent stem cells (Huang, Beanes et al. 2002; Mizuno, Zuk et al. 2002) (Zuk, Zhu et al. 2001). Zuk et al. (Zuk et al., (In Press) Human Adipose Tissue Is A Source Of Multipotent Stem Cells, Molecular Biology of the Cell) and others have previously shown that this tissue is a source of endothelial cells (Kern, Knedler et al. 1983; Hutley, Herington et al. 2001) [U.S. Pat. No. 5,372,945 Alchas et al, 1994] though these latter documents did not examine and do not speak in any way to endothelial precursor cells.

Stem cells are the master cells of the body. Stem cells from embryos or embryonic stem cells (ESCs) are know to become many if not all of the cell and tissue types of the body. These early fetal cells not only contain all the genetic information of the individual but also contain the nascent capacity to become any of the 200+ cells and tissues of the body. Ongoing research suggests that these cells have tremendous scientific and clinical potential.

However, ESCs have theoretic limitations to their use. If used clinically they would necessarily be derived from another individual, an embryo. When stem cells or tissues derived from them are transplanted into another person, toxic immune suppressing drugs may be needed by the cell recipient to prevent rejection. In addition, another individual's cells can carry viruses or other rare but significant diseases that can be transmitted to the recipient. Also, ESC-like cells (eg. teratomas) are known to form tumors.

Recently, non-embryonic or adult stem cells have been identified and represent an important potential alternative to the clinical use of ESCs. These cells reside quietly in many if not all tissues, presumably waiting to respond to trauma or other destructive disease processes so that they can heal the injured tissue. Emerging scientific evidence indicates that each individual carries a pool of stem cells that may share with ESCs the ability to become many if not all types of cells and tissues.

Adult stem cell populations have been shown to be present in one or more of skin, muscle, marrow, liver, brain, and adipose tissue. To date proposed application of such cells in tissue engineering involve increasing cell number, purity, and maturity by processes of cell purification and cell culture. These steps are necessary to compensate for the rarity of stem cells in most tissues. For example, mesenchymal stem cell frequency in bone marrow is estimated at between 1 in 100,000 and 1 in 1 million nucleated cells. Similarly, extraction of stem cells from skin involves a complicated series of cell culture steps over several weeks. Use of skeletal muscle-derived stem cells in clinical trials of heart disease employs a two to three week culture phase in which cell number is increased to clinically relevant numbers and cell differentiation into muscle is promoted.

These expansion and differentiation steps may provide increased cell number, purity, and maturity, but they do so at a cost. This cost can include one or more of: loss of cell function due to cell aging, loss of potentially useful non-stem cell cell populations, delays in potential application of cells to patients, increased monetary cost, and increased risk of contamination of cells with environmental microorganisms during culture. While human data is now becoming available with marrow-derived cells that have not been manipulated but rather used as essentially whole marrow (Horwitz, Prockop et al. 1999; Horwitz, Prockop et al. 2001) (Strauer, Brehm et al. 2002), the clinical benefit derived has been suboptimal, an outcome almost certainly related to the limited cell dose and purity available from marrow.

A number of devices have been developed for harvesting cells from adipose tissue, but these devices can suffer from one or more of inability to optimally accommodate an aspiration device for removal of adipose tissue, lack of partial or full automation from the harvesting of adipose tissue phase through the processing of tissue phases, lack of volume capacity greater than 100 ml of adipose tissue, lack of a partially or completely closed system from the harvesting of adipose tissue phase through the processing of tissue phases, and lack of disposability of components to attenuate concomitant risks of cross-contamination of material from one sample to another.

There is need for alternate approaches in which a population of active cells with increased yield, consistency and/or purity can be prepared rapidly and reliably, and whereby the need for post-extraction manipulation of the cells can be reduced or eliminated. Ideally this cell population would be obtained in a manner that is suitable for their direct placement into a recipient.

SUMMARY OF THE INVENTION

The present invention is directed to compositions, methods, and systems for using cells derived from adipose tissue that are placed directly into a recipient along with such additives necessary to promote, engender, or support a therapeutic, structural, or cosmetic benefit.

In one embodiment, adipose tissue processing occurs in a system that maintains a closed, sterile fluid/tissue pathway. This is achieved by use of a pre-assembled, linked set of closed, sterile containers and tubing allowing for transfer of tissue and fluid elements within a closed pathway. This processing set can be linked to a series of processing reagents (e.g., saline, enzymes, etc.) inserted into a device which can control the addition of reagents, temperature, and timing of processing thus relieving operators of the need to manually manage the process. In a preferred embodiment the entire procedure from tissue extraction through processing and placement into the recipient would all be performed in the same facility, indeed, even within the same room of the patient undergoing the procedure.

In accordance with one aspect of the invention, raw adipose tissue is processed to substantially remove mature adipocytes and connective tissue thereby obtaining a heterogeneous plurality of adipose tissue-derived cells suitable for placement within the body of a recipient. The cells may be placed into the recipient in combination with other cells, tissue, tissue fragments, or other stimulators of cell growth and/or differentiation. In a preferred embodiment, the cells, with any of the above mentioned additives, are placed into the person from whom they were obtained in the context of a single operative procedure with the intention of deriving a therapeutic, structural, or cosmetic benefit to the recipient.

In one embodiment, a method of treating a patient includes steps of: a) providing a tissue removal system; b) removing adipose tissue from a patient using the tissue removal system, the adipose tissue having a concentration of stem cells; c) processing at least a part of the adipose tissue to obtain a concentration of stem cells other than the concentration of stem cells of the adipose tissue before processing; and d) administering the stem cells to a patient without removing the stem cells from the tissue removal system before being administered to the patient.

In another embodiment, a method of treating a patient includes: a) providing an adipose tissue removal system; b) removing adipose tissue from a patient using the adipose tissue removal system, the adipose tissue having a concentration of stem cells; c) processing the adipose tissue to increase the concentration of stem cells in the adipose tissue; d) mixing the adipose tissue having the concentrated stem cells with another unit portion of adipose tissue; and e) administering the adipose tissue with the increased concentration of stem cells to a patient.

A system in accordance with the invention herein disclosed includes a) a tissue collection container including i) a tissue collecting inlet port structured to receive adipose tissue removed from a patient; and ii) a filter disposed within the container and being structured to retain adipose tissue removed from a patient and to pass non-adipose tissue removed from the patient; b) a mixing container coupled to the tissue collection container to receive stem cells obtained from the adipose tissue without removal of the stem cells from the tissue removal system, and including an additive port for the administration of at least one additive to mix with the stem cells contained therein; and c) an outlet structured to permit the cells in the mixing container to be removed from the tissue collection system for administration to a patient.

A composition of the invention includes a first portion of adipose tissue removed from a patient that has a concentration of stem cells, and a second portion of adipose tissue removed from the patient having a concentration of stem cells greater than the first portion of adipose tissue.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

DETAILED DESCRIPTION OF THE PREFERRED EMBODIMENT

Figure 1:
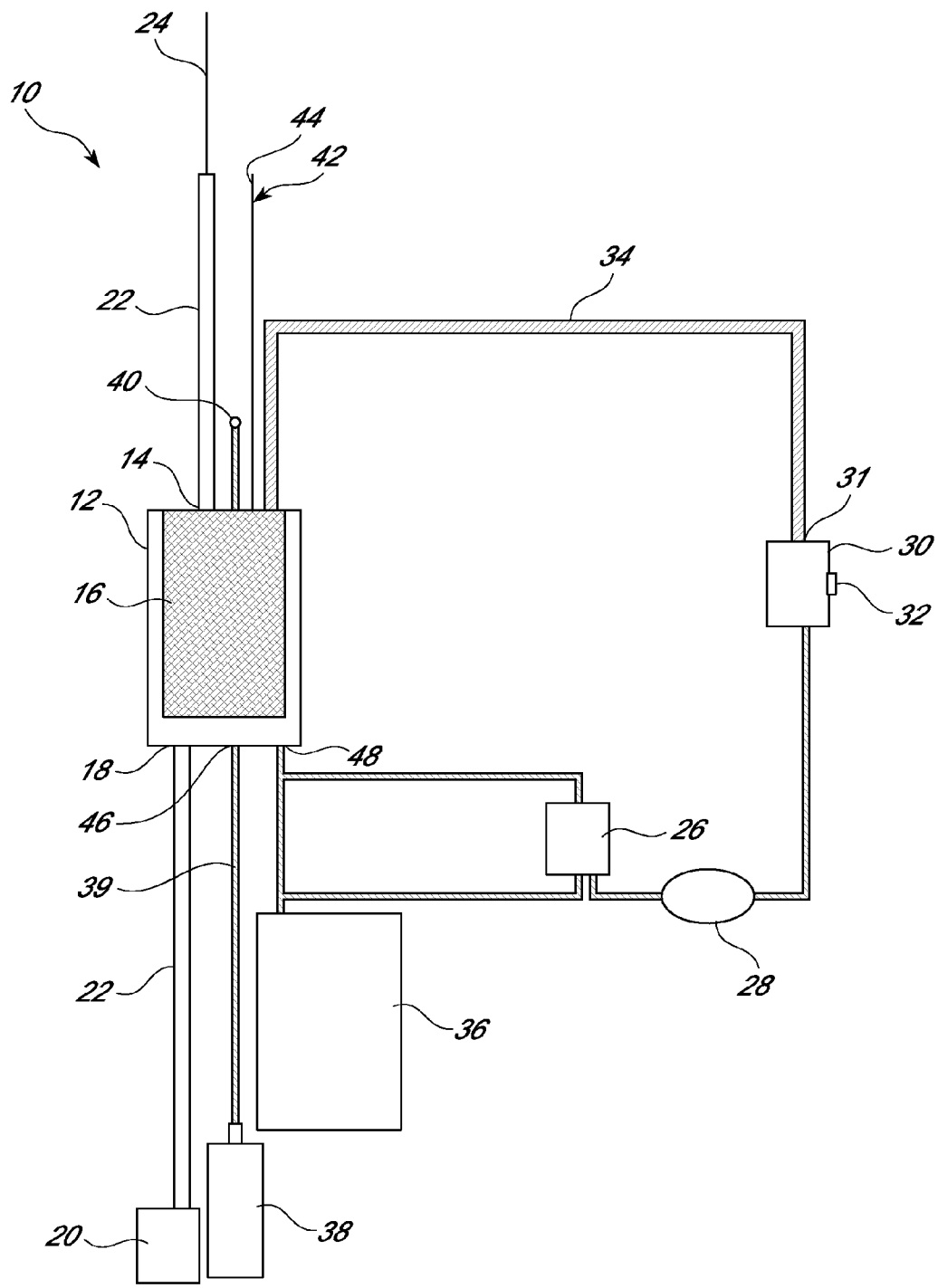
FIG. 1 depicts a tissue removal system for processing adipose tissue.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be practiced in conjunction with various cell or tissue separation techniques that are conventionally used in the art, and only so much of the commonly practiced process steps are included herein as are necessary to provide an understanding of the present invention.

The present invention is directed to a cell population present in adipose tissue, and systems and methods for administering the cell population into a human or animal patient. The cell population of the adipose tissue may be used as a source of cells for therapeutic and cosmetic applications. Among other things, the cells may be used for regenerative medicine, such as diseases that can be treated with regenerating cells. The cells of the population may be administered to a patient without other adipocytes or connective tissue, or may be administered mixed together with adipose tissue in a concentrated amount, as discussed herein.

It has been discovered that adipose tissue is an especially rich source of stem cells. This finding may be due, at least in part, to the ease of removal of the major non-stem cell component of adipose tissue, the adipocyte. Thus, in both human and animal studies, processed lipoaspirate (PLA) contains stem cells at a frequency of at least 0.1%, and more typically greater than 0.5%. In certain embodiments of the invention, PLA has been obtained which contains between about 2-12% stem cells. In even further embodiments, the PLA is processed to obtain a population of cells where the stem cells constitute between up to 100% of the cells in the population. The amount of stem cells obtained in accordance with the invention herein disclosed is substantially greater than the published frequency of 1 in 100,000 (0.001%) in marrow (Castro-Malaspina, Ebell et al. 1984) (Muschler, Nitto et al. 2001). Furthermore, collection of adipose tissue is associated with lower morbidity than collection of a similar volume of marrow (Nishimori, Yamada et al. 2002). In addition, adipose tissue contains endothelial precursor cells, which are capable of providing therapy to patients (see e.g., Masuda, H., C. Kalka, and T. Asahara, Endothelial progenitor cells for regeneration. Hum Cell, 2000. 13(4): p. 153-60; Kaushal, S., et al., Functional small-diameter neovessels created using endothelial progenitor cells expanded ex vivo. Nat Med, 2001. 7(9): p. 1035-40; and Kawamoto, A., et al., Therapeutic potential of ex vivo expanded endothelial progenitor cells for myocardial ischemia. Circulation, 2001. 103(5): p. 634-7.

As used herein, "adipose tissue" refers to a tissue containing multiple cell types including adipocytes and microvascular cells. Adipose tissue includes stem cells and endothelial precursor cells. Accordingly, adipose tissue refers to fat including the connective tissue that stores the fat.

As used herein, "unit of adipose tissue" refers to a discrete or measurable amount of adipose tissue. A unit of adipose tissue may be measured by determining the weight and/or volume of the unit. Based on the data identified above, a unit of processed lipoaspirate, as removed from a patient, has a cellular component in which at least 0.1% of the cellular component is stem cells. In reference to the disclosure herein, a unit of adipose tissue may refer to the entire amount of adipose tissue removed from a patient, or an amount that is less than the entire amount of adipose tissue removed from a patient. Thus, a unit of adipose tissue may be combined with another unit of adipose tissue to form a unit of adipose tissue that has a weight or volume that is the sum of the individual units.

As used herein, "portion" refers to an amount of a material that is less than a whole. A minor portion refers to an amount that is less than 50%, and a major portion refers to an amount greater than 50%. Thus, a unit of adipose tissue that is less than the entire amount of adipose tissue removed from a patient is a portion of the removed adipose tissue.

As used herein, "stem cell" refers to a multipotent cell with the potential to differentiate into a variety of other cell types, which perform one or more specific functions and have the ability to self-renew. Some of the stem cells disclosed herein may be pluripotent.

As used herein, "processed lipoaspirate" (PLA) refers to adipose tissue that has been processed to separate the active cellular component (e.g., the component containing stem cells) from the mature adipocytes and connective tissue. Typically, PLA refers to the pellet of cells obtained by washing and separating the cells from the adipose tissue. The pellet is typically obtained by centrifuging a suspension of cells so that the cells aggregate at the bottom of a centrifuge container.

In practicing the methods disclosed herein, the cells that are administered to a patient are obtained from adipose tissue. Adipose tissue can be obtained by any method known to a person of ordinary skill in the art. For example, adipose tissue may be removed from a patient by suction-assisted lipoplasty, ultrasound-assisted lipoplasty, and excisional lipectomy. In addition, the procedures may include a combination of such procedures, such as a combination of excisional lipectomy and suction-assisted lipoplasty. As the tissue or some fraction thereof is intended for reimplantation into a patient the adipose tissue should be collected in a manner that preserves the viability of the cellular component and that minimizes the likelihood of contamination of the tissue with potentially infectious organisms, such as bacteria and/or viruses. Thus, the tissue extraction should be performed in a sterile or aseptic manner to minimize contamination. Suction assisted lipoplasty may be desirable to remove the adipose tissue from a patient as it provides a minimally invasive method of collecting tissue with minimal potential for stem cell damage that may be associated with other techniques, such as ultrasound assisted lipoplasty.

For suction-assisted lipoplastic procedures, adipose tissue is collected by insertion of a cannula into or near an adipose tissue depot present in the patient followed by aspiration of the adipose into a suction device. In one embodiment, a small cannula may be coupled to a syringe, and the adipose tissue may be aspirated using manual force. Using a syringe or other similar device may be desirable to harvest relatively moderate amounts of adipose tissue (e.g., from 0.1 ml to several hundred milliliters of adipose tissue). Procedures employing these relatively small devices have the advantage that the procedures can be performed with only local anesthesia, as opposed to general anesthesia. Larger volumes of adipose tissue above this range (e.g., greater than several hundred milliliters) may require general anesthesia at the discretion of the donor and the person performing the collection procedure. When larger volumes of adipose tissue are desired to be removed, relatively larger cannulas and automated suction devices may be employed in the procedure.

Excisional lipectomy procedures include, and are not limited to, procedures in which adipose tissue-containing tissues (e.g., skin) is removed as an incidental part of the procedure; that is, where the primary purpose of the surgery is the removal of tissue (e.g., skin in bariatric or cosmetic surgery) and in which adipose tissue is removed along with the tissue of primary interest.

The adipose tissue that is removed from a patient is collected into a device for further processing. As discussed herein, and in one embodiment, the device is designed for and dedicated to the purpose of collecting tissue for manufacture of a processed adipose tissue cell population, which includes stem cells and/or endothelial precursor cells. In other embodiments, the device may be any conventional device that is typically used for tissue collection by physicians performing the extraction procedure.

The amount of tissue collected will be dependent on a number of variables including, but not limited to, the body mass index of the donor, the availability of accessible adipose tissue harvest sites, concomitant and pre-existing medications and conditions (such as anticoagulant therapy), and the clinical purpose for which the tissue is being collected. Experience with transplant of hematopoietic stem cells (bone marrow or umbilical cord blood-derived stem cells used to regenerate the recipient's blood cell-forming capacity) shows that engraftment is cell dose-dependent with threshold effects. Thus, it is likely that the general principle that "more is better" will be applied within the limits set by other variables and that where feasible the harvest will collect as much tissue as possible.

It has been discovered that the stem cell percentage of 100 ml of adipose tissue extracted from a lean individual is greater than that extracted from an obese donor (Table 1). This reflects a dilutive effect of the increased fat content in the obese individual. Therefore, it may be desirable, in accordance with one aspect of the invention, to obtain larger amounts of tissue from overweight donors compared to the amounts that would be withdrawn from leaner patients. This observation also indicates that the utility of this invention is not limited to individuals with large amounts of adipose tissue.

TABLE 1

Effect of Body Mass Index on Tissue and Cell Yield Amount of Tissue

| Body Mass Index Status | Amount of Tissue Obtained | Total Cell Yield ($\times 10^7$) |
|---|---|---|
| Normal | 641 ± 142 | 2.1 ± 0.4 |
| Obese | 1,225 ± 173 | 2.4 ± 0.5 |
| p vaule | 0.03 | 0.6 |

Patients undergoing treatment in accordance with the disclosure herein receive a different concentration of stem cells than other treatments employing adipose tissue or stem cells derived from adipose tissue. Thus, the adipose tissue that is removed from a patient is processed to change the concentration of stem cells that are administered to the patient. In a preferred embodiment of the invention, patients receive a higher concentration of stem cells than the concentration of stem cells typically present in adipose tissue transplants and other similar stem cell based therapies. The concentrated stem cells may be administered in a composition comprising adipo-derived stem cells and/or endothelial precursor cells substantially free from mature adipocytes and connective tissue, or, as another example, the concentrated stem cells may be administered in a composition comprising a unit of adipose tissue with an increased amount of stem cells. A composition of the invention includes a concentration of stem cells that is greater than the concentration of stem cells found in an equivalent unit of non-processed adipose tissue. In certain embodiments, the composition has a cellular component in which at least 0.1% of the cells are stem cells. In other embodiments, the composition has a cellular component in which the stem cells comprise between about 2% and 12% of the cellular component. Higher concentrations of stem cells, such as up to 100%, are also included in different compositions. The composition may include additional components, such as cell differentiation factors, growth promoters, immunosuppressive agents, or medical devices, as discussed herein. To obtain certain compositions in which the composition primarily contains one type of cell (e.g., adipo-derived stem cells or adipo-derived endothelial precursor cells), any suitable method for separating the different cell types may be employed, such as the use of cell-specific antibodies that recognize and bind antigens present on either stem cells or endothelial precursor cells.

For most applications preparation of the active cell population will require depletion of the mature fat-laden adipocyte component of adipose tissue. This is typically achieved by a series of washing and disaggregation steps in which the tissue is first rinsed to reduce the presence of free lipids (released from ruptured adipocytes) and peripheral blood elements (released from blood vessels severed during tissue harvest), and then disaggregated to free intact adipocytes and other cell populations from the connective tissue matrix. In certain embodiments, the entire adipocyte component, or non-stem cell component, is separated from the stem cell component of the adipose tissue. In other embodiments, only a portion or portions of the adipocyte component is separated from the stem cells. Thus, in certain embodiments, the stem cells can be administered with endothelial precursor cells.

Rinsing is an optional, but preferred, step in which the tissue is mixed with solutions to wash off free lipid and single cell components, such as those components in blood, leaving behind intact adipose tissue fragments. In one embodiment, the adipose tissue that is removed from the patient is mixed with isotonic saline or other physiologic solution(s) (e.g., PLASMALYE®), of BAXTER® Inc. or NORMSO®. of Abbott Labs). Intact adipose tissue fragments can be separated from the free lipid and cells by any means known to persons or ordinary skill in the art including, but not limited to, filtration, decantation, sedimentation, or centrifugation. In the illustrated embodiment of the invention, the adipose tissue is separated from non-adipose tissue by employing a filter disposed within a tissue collection container, as discussed herein. In other embodiments, the adipose tissue is separated from non-adipose tissue using a tissue collection container that utilizes decantation, sedimentation, and/or centrifugation techniques to separate the materials.

The intact tissue fragments are then disaggregated using any conventional techniques or methods, including mechanical force (mincing or shear forces), enzymatic digestion with single or combinatorial proteolytic enzymes, such as collagenase, trypsin, lipase, liberase HI, as disclosed in U.S. Pat. No. 5,952,215, and pepsin, or a combination of mechanical and enzymatic methods. For example, the cellular component of the intact tissue fragments may be disaggregated by methods using collagenase-mediated dissociation of adipose tissue, similar to the methods for collecting microvascular endothelial cells in adipose tissue, as disclosed in U.S. Pat. No. 5,372,945. Additional methods using collagenase that may be used in practicing the invention are disclosed in U.S. Pat. Nos. 5,830,714 and 5,952,215, and by Williams, S. K., S. McKenney, et al. (1995). "Collagenase lot selection and purification for adipose tissue digestion." *Cell Transplant* 4(3): 281-9. Similarly, a neutral protease may be used instead of collagenase, as disclosed in Twentyman, P. R. and J. M. Yuhas (1980). "Use of bacterial neutral protease for disaggregation of mouse tumours and multicellular tumor spheroids." *Cancer Lett* 9(3): 225-8. Furthermore, methods may employ a combination of enzymes, such as a combination of collagenase and trypsin, as disclosed in Russell, S. W., W. F. Doe, et al. (1976). "Inflammatory cells in solid murine neoplasms. I.

Tumor disaggregation and identification of constituent inflammatory cells." *Int J Cancer* 18(3): 322-30; or a combination of an enzyme, such as trypsin, and mechanical dissociation, as disclosed in Engelholm, S. A., M. Spang-Thomsen, et al. (1985). "Disaggregation of human solid tumours by combined mechanical and enzymatic methods." *Br J Cancer* 51(1): 93-8.

The active cell population (processed lipoaspirate) may then be obtained from the disaggregated tissue fragments by reducing the presence of mature adipocytes. A suspension of the processed lipoaspirate and the liquid in which the adipose tissue was disaggregated is then passed to another container, such as a cell collection container. The suspension may flow through one or more conduits to the cell collection container by using a pump, such as a peristaltic pump, that withdraws the suspension from the tissue collection container and urges it to the cell collection container. Other embodiments may employ the use of gravity or a vacuum while maintaining a closed system. Separation of the cells in the suspension may be achieved by buoyant density sedimentation, centrifugation, elutriation, differential adherence to and elution from solid phase moieties, antibody-mediated selection, differences in electrical charge; immunomagnetic beads, flourescence activated cell sorting (FACS), or other means. Examples of these various techniques and devices for performing the techniques may be found in Hemstreet, G. P., 3rd, P. G. Enoch, et al. (1980). "Tissue disaggregation of human renal cell carcinoma with further isopyknic and isokinetic gradient purification." Cancer Res 40(4): 1043-9; Schweitzer, C. M., van, et al. (1995). "Isolation and culture of human bone marrow endothelial cells." Exp Hematol 23(1): 41-8; Gryn, J., R. K. Shadduck, et al. (2002). "Factors affecting purification of CD34(+) peripheral blood stem cells using the BAXTER® ISOLEX™ 300i." J Hematother Stem Cell Res 11(4): 719-30; Prince, H. M., J. Bashford, et al. (2002). "ISOLEX™ 300i CD34-selected cells to support multiple cycles of high-dose therapy." Cytotherapy 4(2): 137-45; Watts, M. J., T. C. Somervaille, et al. (2002). "Variable product purity and functional capacity after CD34 selection: a direct comparison of the CLINIMACS® (v2.1) and ISOLEX™ 300i (v2.5) clinical scale devices." Br J Haematol 118(1): 117-23; Mainwaring, G. and A. F. Rowley (1985). "Separation of leucocytes in the dogfish (*Scyliorhinus canicula*) using density gradient centrifugation and differential adhesion to glass coverslips." Cell Tissue Res 241(2): 283-90; Greenberg, A. W. and D. A. Hammer (2001). "Cell separation mediated by differential rolling adhesion." Biotechnol Bioeng 73(2): 111-24; and U.S. Pat. Nos. 6,277,060; 6,221,315; 6,043,066; 6,451,207; 5,641,622; and 6,251,295. In the illustrated embodiment, the cells in the suspension are separated from the acellular component of the suspension using a spinning membrane filter. In other embodiments, the cells in the suspension are separated from the acellular component using a centrifuge. In one such exemplary embodiment, the cell collection container may be a flexible bag that is structured to be placed in a centrifuge (e.g., manually or by robotics). In other embodiments, a flexible bag is not used. After centrifugation, the cellular component forms a pellet, which may then be resuspended with a buffered solution so that the cells can be passed through one or more conduits to a mixing container, as discussed herein. The resuspension fluids may be provided by any suitable means. For example, a buffer may be injected into a port on the cell collection container, or the cell collection container may include a reserve of buffer that can be mixed with the pellet of cells by rupturing the reserve. When a spinning membrane filter is used, resuspension is optional since the cells remain in a volume of liquid after the separation procedure.

Although certain embodiments of the invention are directed to methods of fully disaggregating the adipose tissue to separate the active cells from the mature adipocytes and connective tissue, additional embodiments of the invention are directed to methods in which the adipose tissue is only partially disaggregated. For example, partial disaggregation may be performed with one or more enzymes, which are removed from the at least a part of the adipose tissue early, relative to an amount of time that the enzyme would otherwise be left thereon to fully disaggregate the tissue. Such a process may require less processing time.

In one particular embodiment, the tissue is washed with sterile buffered isotonic saline and incubated with collagenase at a collagenase concentration, temperature, and time sufficient to provide adequate disaggregation. In a preferred embodiment, the collagenase enzyme used will be approved for human use by the relevant authority (e.g., the U.S. Food and Drug Administration). Suitable collagenase preparations include recombinant and non-recombinant collagenase. Non-recombinant collagenase may be obtained from F. Hoffmann-La Roche Ltd, Indianapolis, Ind. and/or Advance Biofactures Corp., Lynbrook, N.Y. Recombinant collagenase may also be obtained as disclosed in U.S. Pat. No. 6,475,764.

In one embodiment, solutions contain collagenase at concentrations from about 10 μg/ml to about 50 μg/ml and are incubated at from about 30° C. to about 38° C. for from about 20 minutes to about 60 minutes. These parameters will vary according to the source of the collagenase enzyme, optimized by empirical studies, in order to validate that the system is effective at extracting the desired cell populations in an appropriate time frame. A particular preferred concentration, time and temperature is 20 μg/ml collagenase BLENDZYME® 1, Roche) incubated for 45 minutes, at about 37° C. In a particularly preferred embodiment the collagenase enzyme used is material approved for human use by the relevant authority (e.g., the U.S. Food and Drug Administration). The collagenase used should be free of microorganisms and contaminants, such as endotoxin.

Following disaggregation the active cell population may be washed/rinsed to remove additives and/or by-products of the disaggregation process (e.g., collagenase and newly-released free lipid). The active cell population could then be concentrated by centrifugation or other methods known to persons of ordinary skill in the art, as discussed above. These post-processing wash/concentration steps may be applied separately or simultaneously.

In one embodiment, the cells are concentrated and the collagenase removed by passing the cell population through a continuous flow spinning membrane system or the like, such as, for example, the system disclosed in U.S. Pat. Nos. 5,034,135; and 5,234,608.

In addition to the foregoing, there are many post-wash methods that may be applied for further purifying the active cell population. These include both positive selection (selecting the target cells), negative selection (selective removal of unwanted cells), or combinations thereof.

In one embodiment, a solid phase material with adhesive properties selected to allow for differential adherence and/or elution of a subpopulation of cells within the processed lipoaspirate is inserted into the system after the cell washing step. This general approach has been performed in clinical blood transfusion in which filters differentially capturing leukocytes are used to deplete transfused red cells of contaminating white blood cell (Soli, M., et al., A multicentre evaluation of a new filtration protocol for leucocyte depletion of high-haematocrit red blood cells collected by an automated blood collection system. Vox Sang, 2001. 81(2): p. 108-12;

Smith, J. W., Apheresis techniques and cellular immunomodulation. Ther Apher, 1997. 1(3): p. 203-6). Filters of this type are distributed by Pall Bedical (LEUKOGRAD® RS and PURECELL™ RCQ) and Asahi (RS2000). Differential adherence has also been applied to positive selection of monocytes (Berdel, W. E., et al., Purification of human monocytes by adherence to polymeric fluorocarbon. Characterization of the monocyte-enriched cell fraction. Immunobiology, 1982. 163(5): p. 511-20) and epidermal stem cells (Bickenbach, J. R. and E. Chism, Selection and extended growth of murine epidermal stem cells in culture. Exp Cell Res, 1998. 244(1): p. 184-95). In this embodiment the processed lipoaspirate would be passed through a filter material under flow and buffer conditions pre-determined to promote differential adherence of target cells and unwanted cell populations. For positive selection the filter material and conditions would allow preferential adherence of target cells while unwanted material would pass freely through the filter and be washed away with excess buffer. Target cells would be eluted from the filter by changing the conditions such as flow rate, pH, ionic strength, and/or presence of cations necessary for adhesion. The filter material could be in the form of a three-dimensional mesh, packed cassette of small particles, hollow-fibers or other mechanism with high surface area. In a preferred embodiment, this filter device would be an integral part of the disposable set shown in FIG. 1 and would be inserted into the device shown in FIG. 4. Both the set and device would have to be modified slightly from those examples shown in the specified figures; FIG. 1 to include the filter and housing and FIG. 4 to allow for insertion of the filter housing and tubing (including valves) necessary for maintenance of a closed, sterile fluid pathway. Alternatively the mixing chamber (Component 108 of FIG. 4; component 30 of FIG. 1) could be replaced by the device fittings and filter/housing respectively.

An alternate embodiment of this differential adherence approach would include use of antibodies and/or combinations of antibodies recognizing surface molecules differentially expressed on target and unwanted cells. Selection on the basis of expression of specific cell surface markers (or combinations thereof) is another commonly applied technique in which antibodies are attached (directly or indirectly) to a solid phase support structure (Geiselhart, A., et al., Positive selection of CD56+ lymphocytes by magnetic cell sorting. Nat Immun, 1996. 15(5): p. 227-33; Formanek, M., et al., Magnetic cell separation for purification of human oral keratinocytes: an effective method for functional studies without prior cell subcultivation. Eur Arch Otorhinolaryngol, 1998. 255(4): p. 211-5; Graepler, F., U. Lauer, and M. Gregor, Magnetic cell sorting for parietal cell purification using a new monoclonal antibody without influence on cell function. J Biochem Biophys Methods, 1998. 36(2-3): p. 143-55; Kobari, L., et al., CD133+ cell selection is an alternative to CD34+ cell selection for ex vivo expansion of hematopoietic stem cells. J Hematother Stem Cell Res, 2001. 10(2): p. 273-81; Mohr, M., et al., Simultaneous immunomagnetic CD34+ cell selection and B-cell depletion in peripheral blood progenitor cell samples of patients suffering from B-cell non-Hodgkin's lymphoma. Clin Cancer Res, 2001. 7(1): p. 51-7; and Pugh, R. E., et al., CD19 selection improves the sensitivity of B cell lymphoma detection. J Hematother, 1998. 7(2): p. 159-68). This approach has obvious applications in both positive and negative selection in which, for example, residual white blood cells might be removed by use of the CD45 antibody). Similarly, Reyes et al have applied a complex blend of antibodies in the selection of a multipotential adult progenitor cell from human bone marrow (Reyes, M., et al., Purification and ex vivo expansion of postnatal human marrow mesodermal progenitor cells. Blood, 2001. 98(9): p. 2615-25). For example, an antibody such as AP2 (Joyner, C. J., et al., Development of a monoclonal antibody to the aP2 protein to identify adipocyte precursors in tumours of adipose differentiation. Pathol Res Pract, 1999. 195(7): p. 461-6) which specifically binds to adipocytic cells could be employed to preferentially deplete residual adipocytic cells (including immature adipocytes and adipoblasts). Positive selection could be applied by use of antibodies specific for the target cell population(s). For example, Quirici et al have used antibodies to the Nerve Growth Factor Receptor to enrich bone marrow-derived mesenchymal stem cells (Quirici, N., et al., Isolation of bone marrow mesenchymal stem cells by anti-nerve growth factor receptor antibodies. Exp Hematol, 2002. 30(7): p. 783-91).

In one embodiment of an antibody-based approach, an antibody (for example AP2) or a cocktail of antibodies (for example AP2, CD3, CD19, CD11b) would be added to the processed lipoaspirate. Many other antibodies and combinations of antibodies will be recognized by one skilled in the art and these examples are provided by way of example only. After incubation, under conditions pre-determined to allow for optimal binding of these antibodies to their cognate antigens, the cells would be washed by passing through the spinning membrane filter or other embodiment of the cell washing chamber to remove unbound, excess antibody. The cells would then be passed over a solid phase structure similar to that described in the embodiment above but in which the solid phase has attached a secondary antibody capable of high affinity attachment to the primary antibodies now bound to the cell surface. Target cells, for example the adipose tissue-derived stem cell, would pass freely through this filter by virtue of the absence of expression of cell surface antigens recognized by the selected antibody (antibody cocktail) thereby creating a negative selection system. In this embodiment the disposable set (FIG. 3) and device (FIG. 4) would be subject to minor modifications very similar to those described in the above embodiment.

An antibody-mediated positive selection embodiment could be achieved in very similar fashion by including a third additive that facilitates detachment of the cells from the solid phase support. In this embodiment, the enzyme papain or cymopapain could be added to cleave the antibody molecules and release cells from the solid phase support (Civin, C. I., et al., Positive stem cell selection--basic science. Prog Clin Biol Res, 1990. 333(387): p. 387-401; discussion 402). Another alternative would be the use of specific peptides that would compete with the cell surface antigen for binding to the antibodies, as described by Tseng-Law et al, U.S. Pat. No. 6,017, 719.

In another embodiment the cell pellet could be resuspended, layered over (or under) a fluid material formed into a continuous or discontinuous density gradient and placed in a centrifuge for separation of cell populations on the basis of cell density. Examples of media suitable for formation of such gradients include PERCOLL® and FICOLL-PAQUE™ (Qian, X., L. Jin, and R. V. Lloyd, PERCOLL® Density Gradient-Enriched Populations of Rat Pituitary Cells: Interleukin 6 Secretion, Proliferative Activity, and Nitric Oxide Synthase Expression. Endocr Pathol, 1998. 9(1): p. 339-346; Smits, G., W. Holzgreve, and S. Hahn, An examination of different PERCOLL® density gradients and magnetic activated cell sorting (MACS®) for the enrichment of fetal erythroblasts from maternal blood. Arch Gynecol Obstet, 2000. 263(4): p. 160-3) or FICOLL-PAQUE™ (Lehner, M. and W. Holter, Endotoxin-free purification of monocytes for dendritic cell generation via discontinuous density gradient centrifugation based on diluted FICOLL-PAQUE™ Plus. Int Arch Allergy Immunol, 2002. 128(1): p. 73-6). Van Merris et al, (Van Merris, V., et al., Separation of bovine bone marrow into maturation-related myeloid cell fractions. Vet. Immunol. Immunopathol, 2001. 83(1-2): p. 11-7) employed a discontinuous three-step PERCOLL® gradient to separate bovine myeloid cells according to their maturation state on this basis. This embodiment would be capable of separating out certain residual blood cell populations and immature adipocytes (pre-adipocytes) from the cell population.

In a similar embodiment continuous flow approaches such as apheresis (Smith, J. W., Apheresis techniques and cellular immunomodulation. Ther Apher, 1997. 1(3): p. 203-6) and elutriation (with or without counter-current) (Lasch, J., G. Kullertz, and J. R. Opalka, Separation of erythrocytes into age-related fractions by density or size? Counterflow centrifugation. Clin Chem Lab Med, 2000. 38(7): p. 629-32; Ito, Y. and K. Shinomiya, A new continuous-flow cell separation method based on cell density: principle, apparatus, and preliminary application to separation of human buffy coat. J Clin Apheresis, 2001. 16(4): p. 186-91; Dlubek, D., et al., Enrichment of normal progenitors in counter-flow centrifugal elutriation (CCE) fractions of fresh chronic myeloid leukemia leukapheresis products. Eur J Haematol, 2002. 68(5): p. 281-8) may also be employed. Such mechanisms have been used to fractionate blood cells, including separation of red blood cells on the basis of age (Lasch, J., G. Kullertz, and J. R. Opalka, Separation of erythrocytes into age-related fractions by density or size? Counterflow centrifugation. Clin Chem Lab Med, 2000. 38(7): p. 629-32) and application of this general approach to further purification of cells of interest from processed lipoaspirate will be readily apparent to one skilled in the art. This embodiment may require modification of the device in FIG. 4 and the disposable set (FIG. 3) such that the device would be integrated with a second device providing the apheresis or elutriation capability.

Adherence to plastic followed by a short period of cell expansion has also been applied in bone marrow-derived adult stem cell populations (Jaiswal, N., et al., Osteogenic differentiation of purified, culture-expanded human mesenchymal stem cells in vitro. J Cell Biochem, 1997. 64(2): p. 295-312; Hou, L., et al., Study of in vitro expansion and differentiation into neuron-like cells of human umbilical cord blood mesenchymal stem cells. Zhonghua Xue Ye Xue Za Zhi, 2002. 23(8): p. 415-9). This approach uses culture conditions to preferentially expand one population while other populations are either maintained (and thereby reduced by dilution with the growing selected cells) or lost due to absence of required growth conditions. Sekiya et al have described conditions which might be employed in this regard for bone marrow-derived stem cells (Sekiya, I., et al., Expansion of Human Adult Stem Cells from Bone Marrow Stroma: Conditions that Maximize the Yields of Early Progenitors and Evaluate Their Quality. Stem Cells, 2002. 20(6): p. 530-41). This approach (with or without differential adherence to the tissue culture plastic) could be applied to a further embodiment of this invention. In this embodiment the cells are removed from the device shown in FIG. 4 and placed into a second device providing the cell culture component. This could be in the form of a conventional laboratory tissue culture incubator or a Bioreactor-style device such as that described by Tsao et al, U.S. Pat. No. 6,001,642, or by Armstrong et al, U.S. Pat. No. 6,238,908. In an alternative embodiment, the mixing component (component 108 of the device shown in FIG. 4; component 30 in FIG. 3) could be replaced by a Bioreactor component allowing for short-term adherence and/or cell culture of the processed lipoaspirate. This alternate embodiment would permit integration of the Bioreactor component to the device and remove the need for removing the cells from this device and placement within another.

In certain embodiments, the active cell population is administered directly into the patient. In other words, the active cell population (e.g., the stem cells and/or endothelial precursor cells) are administered to the patient without being removed from the system or exposed to the external environment of the system before being administered to the patient. Providing a closed system reduces the possibility of contamination of the material being administered to the patient. Thus, processing the adipose tissue in a closed system provides advantages over existing methods because the active cell population is more likely to be sterile. In such an embodiment, the only time the stem cells and/or endothelial precursor cells are exposed to the external environment, or removed from the system, is when the cells are being withdrawn into an application device and being administered to the patient. In one embodiment, the application device can also be part of the closed system. Thus, the cells used in these embodiments are not processed for culturing, or cryopreserved.

The active cells that have been concentrated, as described above, may be administered to a patient without further processing, or may be administered to a patient after being mixed with other tissues or cells. In certain embodiments, the concentrated active cells (e.g., stem cells or endothelial precursor cells) are mixed with one or more units of adipose tissue that has not been similarly processed. Thus, by practicing the methods of the invention, a composition comprising adipose tissue with an enhanced concentration of active cells may be administered to the patient. The volumes of the various units of adipose tissue may be different. For example, one volume may be at least 25% greater than the volume of another unit of adipose tissue. Furthermore, one volume may be at least 50%, such as at least 100%, and even 150% or more greater than the volume of another unit of adipose tissue. In addition, the desired composition may be obtained by mixing a first unit of adipose tissue with the concentrated active cell population, which may be a cell pellet containing the active cells, with one or more other units of adipose tissue. In certain embodiments, these other units will not have an increased concentration of stem cells, or in other words, will have an active cell concentration less than that contained in the first unit of adipose tissue. In other embodiments, one of the units is cryopreserved material that contains, for example, an increased concentration of active cells.

In other embodiments, at least a portion of the active cell population is stored for later implantation/infusion. The population may be divided into more than one aliquot or unit such that part of the population of stem cells and/or endothelial precursor cells is retained for later application while part is applied immediately to the patient. Moderate to long-term storage of all or part of the cells in a cell bank is also within the scope of this invention, as disclosed in U.S. patent application Ser. No. 10/242,094, entitled PRESERVATION OF NON EMBRYONIC CELLS FROM NON HEMATOPOIETIC TISSUES, filed Sep. 12, 2002, which claims the benefit of U.S. Provisional Patent Application No. 60/322,070 filed Sep. 14, 2001, which is commonly assigned, and the contents of which are expressly incorporated herein by reference. In such an embodiment, the cells may be mixed with one or more units of fresh or preserved adipose tissue to provide a composition containing the stem cells at a higher concentration than a unit of adipose tissue prior to processing.

At the end of processing, the concentrated cells may be loaded into a delivery device, such as a syringe, for placement into the recipient by either subcutaneous, intravenous, intramuscular, or intraperitoneal techniques. In other words, cells may be placed into the patient by any means known to persons of ordinary skill in the art, for example, they may be injected into blood vessels for systemic or local delivery, into tissue (e.g., cardiac muscle, or skeletal muscle), into the dermis (subcutaneous), into tissue space (e.g., pericardium or peritoneum), or into tissues (e.g., periurethral emplacement), or other location. Preferred embodiments include placement by needle or catheter, or by direct surgical implantation in association with additives such as a preformed matrix.

The active cell population may be applied alone or in combination with other cells, tissue, tissue fragments, demineralized bone, growth factors such as insulin or drugs such as members of the thiaglitazone family, biologically active or inert compounds, resorbable plastic scaffolds, or other additive intended to enhance the delivery, efficacy, tolerability, or function of the population. The cell population may also be modified by insertion of DNA or by placement in cell culture in such a way as to change, enhance, or supplement the function of the cells for derivation of a cosmetic, structural, or therapeutic purpose. For example, gene transfer techniques for stem cells are known by persons of ordinary skill in the art, as disclosed in Mosca, J. D., J. K. Hendricks, et al. (2000). "Mesenchymal stem cells as vehicles for gene delivery." Clin Orthop (379 Suppl): S71-90, and may include viral transfection techniques, and more specifically, adeno-associated virus gene transfer techniques, as disclosed in Walther, W. and U. Stein (2000). "Viral vectors for gene transfer: a review of their use in the treatment of human diseases." Drugs 60(2): 249-71, and Athanasopoulos, T., S. Fabb, et al. (2000). "Gene therapy vectors based on adeno-associated virus: characteristics and applications to acquired and inherited diseases (review)." Int J Mol Med 6(4): 363-75. Non-viral based techniques may also be performed as disclosed in Muramatsu, T., A. Nakamura, et al. (1998). "In vivo electroporation: a powerful and convenient means of nonviral gene transfer to tissues of living animals (Review)." Int J Mol Med 1(1): 55-62.

In one aspect, the cells could be mixed with unprocessed fragments of adipose tissue and placed back into the recipient using a very large gauge needle or liposuction cannula. Transfer of autologous fat without supplementation with processed cells is a common procedure in plastic and reconstructive surgery. However, results can be unpredictable as the transferred material tends to rapidly reabsorb resulting in an unstable graft. Adipose tissue-derived cells of the invention that are, for example, substantially depleted of mature adipocytes may provide an environment that supports prolonged survival and function of the graft.

In another aspect, the cell population could be placed into the recipient and surrounded by a resorbable plastic sheath such as that manufactured by MacroPore Biosurgery™, Inc. (U.S. Pat. Nos. 6,269,716 and 5,919,234). In this setting the sheath would prevent prolapse of muscle and other soft tissue into the area of a bone fracture thereby allowing the emplaced processed adipose tissue-derived cells to promote repair of the fracture. In this aspect, the beneficial effect might be enhanced by supplementaion with additional components such as pro-osteogenic protein growth factors or biological or artificial scaffolds.

In another aspect, the cells could be combined with a gene encoding a pro-osteogenic growth factor which would allow cells to act as their own source of growth factor during bone healing or fusion. Addition of the gene could be by any technology known in the art including but not limited to adenoviral transduction, "gene guns," liposome-mediated transduction, and retrovirus or lentevirus-mediated transduction.

Particularly when the cells and/or tissue containing the cells are administered to a patient other than the patient from which the cells and/or tissue were obtained, one or more immunosuppressive agents may be administered to the patient receiving the cells and/or tissue to reduce, and preferably prevent, rejection of the transplant. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. patent Pub. No. 20020182211. Other examples include cyclosporin, myophenylate mofetil, rapamicin, and anti-thymocyte globulin.

In certain embodiments of the invention, the cells are administered to a patient with one or more cellular differentiation agents, such as cytokines and growth factors. Examples of various cell differentiation agents are disclosed in Gimble, J. M., C. Morgan, et al. (1995). "Bone morphogenetic proteins inhibit adipocyte differentiation by bone marrow stromal cells." J Cell Biochem 58(3): 393-402; Lennon, D. P., S. E. Haynesworth, et al. (1995). "A chemically defined medium supports in vitro proliferation and maintains the osteochondral potential of rat marrow-derived mesenchymal stem cells." Exp Cell Res 219(1): 211-22; Majumdar, M. K., M. A. Thiede, et al. (1998). "Phenotypic and functional comparison of cultures of marrow-derived mesenchymal stem cells (MSCs) and stromal cells." J Cell Physiol 176(1): 57-66; Caplan, A. I. and V. M. Goldberg (1999). "Principles of tissue engineered regeneration of skeletal tissues." Clin Orthop (367 Suppl): S12-6; Ohgushi, H. and A. I. Caplan (1999). "Stem cell technology and bioceramics: from cell to gene engineering." J Biomed Mater Res 48(6): 913-27; Pittenger, M. F., A. M. Mackay, et al. (1999). "Multilineage potential of adult human mesenchymal stem cells." Science 284(5411): 143-7; Caplan, A. I. and S. P. Bruder (2001). "Mesenchymal stem cells: building blocks for molecular medicine in the 21st century." Trends Mol Med 7(6): 259-64; Fukuda, K. (2001). "Development of regenerative cardiomyocytes from mesenchymal stem cells for cardiovascular tissue engineering." Artif Organs 25(3): 187-93; Worster, A. A., B. D. Brower-Toland, et al. (2001). "Chondrocytic differentiation of mesenchymal stem cells sequentially exposed to transforming growth factor-beta1 in monolayer and insulin-like growth factor-I in a three-dimensional matrix." J Orthop Res 19(4): 738-49; Zuk, P. A., M. Zhu, et al. (2001). "Multilineage cells from human adipose tissue: implications for cell-based therapies." Tissue Eng 7(2): 211-28; and Mizuno, H., P. A. Zuk, et al. (2002). "Myogenic differentiation by human processed lipoaspirate cells." Plast Reconstr Surg 109(1): 199-209; discussion 210-1.

By administering the stem cells and/or endothelial precursor cells to a patient, one can treat numerous diseases, including, and not limited to, bone-related disorders, diseases, or injuries, including slow/non-union fractures, osteoporosis (age-related or chemotherapy-induced), inherited diseases of bone (osteogenesis imperfecta); adipose related disorders or diseases; liver related diseases, disorders, or injuries, including liver failure, hepatitis B, and hepatitis C; myocardial infarctions, including heart attack or chronic heart failures; renal diseases or kidney damage; retinal diseases or damage or necrosis; wound healing (e.g., from surgery or diabetic ulcers); skeletal muscle disorders both traumatic and inherited; cartilage and joint repair both traumatic and autoimmune; lung injuries; diabetes; intestinal disorders; nervous system disorders, diseases, or injuries, such as central nervous systems disorders, diseases, or injuries, including spinal cord injuries, Parkinson's disease, Alzheimer's disease, and stroke.

The stem cells may also be administered to a patient for cosmetic purposes, such as by enhancing or improving physical features, including reducing wrinkles, enhancing organ mass, and the like.

A tissue removal system for removing adipose tissue from a patient is illustrated in FIG. 1. In a broad embodiment, tissue removal system 10 includes a tissue collecting container 12 and a mixing container 30 coupled to the tissue collecting container 12. The coupling between mixing container 30 and tissue collecting container 12 preferably defines a closed system in which the tissue that is directed from tissue collecting container 12 to mixing container 30 is not exposed to the external environment. System 10 also includes an outlet 32 that is structured to permit concentrated stem cells to be removed from tissue collection system 10 to be administered to a patient. The tissue collection container 12 includes a tissue collecting inlet port 14 and a filter 16. Filter 16 is disposed within the container, and is structured to retain adipose tissue and to pass non-adipose tissue as, for example, the tissues are removed from the patient. More specifically, filter 16 allows passage of free lipid, blood, and saline, while retaining fragments of adipose tissue during, or in another embodiment after, the initial harvesting of the adipose tissue. In that regard, filter 16 includes a plurality of pores, of either the same or different sizes, but ranging in size from about 20 μm to 5 mm. In a preferred embodiment, the filter is a medical grade polyester mesh of around 200 μm thickness with a pore size of around 265 μm and around 47% open area. This material holds the tissue during rinsing but allows cells to pass out through the mesh following tissue disaggregation. Thus, when the tissues are aspirated from the patient, the non-adipose tissue may be separated from the adipose tissue. Mixing container 30 includes an additive port 31 that is structured to allow a user to administer an additive to the mixing container 30 to mix with stem cells contained in the mixing container 30. In a preferred embodiment, the dimensions of the tissue collection container 12 should be such as to allow retention of approximately 1 liter of tissue fragments within the filter. In other embodiments, the tissue collection container 12 may be sized to hold a greater or smaller volume of tissue fragments; for example, the tissue collection container may be sized to store at least 100 mL of adipose tissue fragments, and up to about 2 L of adipose tissue fragments.

Referring to additional features present in system 10 of FIG. 1, tissue inlet port 14 is coupled to cannula 24 by way of tubing 22 to define a tissue removal line. In the illustrated embodiment, cannula 24 is an integrated, single-use liposuction cannula, and the tubing is a flexible tubing. The cannula is dimensioned to be inserted into a patient to remove adipose tissue from the patient. The tubing 22 used in the system should be capable of withstanding negative pressure associated with suction assisted lipoplasty to reduce the likelihood of collapsing. Tissue collection container 12 also includes an aspiration port 18 disposed on the opposite side of filter 16 from tissue inlet port 14. Aspiration port 18 is structured to be coupled to a suction device 20, which may be manually or automatically operated. Suction device 20 may be a syringe or may be an electric vacuum, among other things. Suction device 20 should be capable of providing a sufficient negative pressure to container 12 and cannula 24 to aspirate tissue from a patient. As illustrated, suction device 20 is coupled to aspiration port 18 by way of tubing 22.

Tissue removal system 10 is illustrated as also including a cell collection container 26 positioned between tissue collection container 12 and mixing container 30. Cell collection container 26 is positioned within system 10 so that cells, such as stem cells, pass from tissue collection container 12 to the cell collection container 26 before being passed to mixing container 30. In the illustrated embodiment, cell collection container 26 is coupled to tissue collection container 12 by way of cell collecting port 48. In one embodiment of system 10, cell collection container 26 includes a cell concentrator (not shown) that facilitates separation of the cells in a suspension. An example of a cell concentrator is a centrifuge device that may separate cells from other materials based on, for example, the size or density of the cells. Another example is a spinning membrane filter, as discussed above. System 10 is also illustrated as including a filter 28 structured to pass the cells from cell collection container 26 to mixing container 30, and to prevent passage of material that is, for example, larger than, the cells. Cell collection container 26 also includes an outlet to waste container 36. The direction of flow of the material contained in cell collection container 26 is determined by the positioning of one or more valves which can control whether the material flows to waste container 36 or mixing container 30.

In the illustrated embodiment, cell filter 28 comprises a plurality of pores having a diameter, or length less than 200 μm. In certain embodiments, the pores may have diameters that are smaller than 200 μm. In other embodiments, the pores have diameters between 20 and 200 μm. Cell filter 28 may be spaced apart from cell collection container 26 or may be contained within cell collection container 26. Cell filter 28 may also be integrally formed in cell collection container 26. Additional embodiments of system 10 do not include filter 28. Cell collection container may be fabricated from any suitable material. For example, cell collection container 26 may be a plastic bag, such as those conventionally used in processing blood in blood banks; or in other embodiments, it may be structurally rigid. In certain embodiments, cell collection container 26 may include a component preparation chamber and a cell washing/separation chamber.

In certain embodiments, the component preparation chamber includes one or more ports for addition of agents that can enhance the process of separating stem cells for administering to a patient, such as growth factors or buffers for resuspending the cells, as discussed above. In these embodiments, component preparation chamber preferably includes a mixing device to mix or agitate the cells and additives in the container. Component preparation chamber also includes one or more ports for removing the cells collected therein. One port may be provided to pass the cells toward mixing container 30. Other ports may be provided to direct cells, or a portion of the cells, to other targets, such as implant materials, including bone fragments, or to cell culturing or purification devices. In one embodiment, the cell washing/separation chamber includes a spinning membrane filter component, which may be used as the cell concentrator in addition to or, preferably, as an alternative to a centrifuge device.

System 10 is also illustrated as including a tissue retrieval line 34 which is positioned to provide a conduit from tissue collection container 12 to mixing container 30. Thus, tissue retrieval line 34 passes or directs tissue contained within tissue collection container 12 to mixing container 30 where the tissue can be mixed with cells obtained from cell collection container 26. In the illustrated embodiment, tissue retrieval line 34 extends into tissue container 12 to remove adipose tissue that is contained in filter 16. Tissue is passed or directed through tissue retrieval line 34 using one or more pumps or suction devices to pass adipose tissue that has been rinsed, but not necessarily disaggregated.

In one embodiment, system 10 includes a temperature control device that is positioned with respect to system 10 to adjust the temperature of the material contained in the tissue collection container 12. In certain embodiments, the temperature control device is a heater, and in other embodiments, temperature control device is a cooler. In additional embodiments, the temperature control device may be able to switch between a heater and a cooler. The temperature control device may be a device that adjusts the temperature of the adipose tissue contained in tissue collecting container 12, or may be a device that is positioned to change the temperature of fluid being delivered to tissue collecting container 12. It has been found that heating the adipose tissue facilitates disaggregation of the tissue to enhance the separation of the active cell component. In addition, it is desirable in certain embodiments to cool a portion of the tissue, preferably the active cell component to provide protection to the cells. Even mild cooling of the cells may provide suitable protection to enhance cell survival during the processing.

Outlet 32 of tissue removal system 10 is illustrated as being a component of mixing container 30. In additional embodiments, outlet 32 is spaced apart from mixing container 30. Outlet 32 preferably comprises a closure that maintains the sealed configuration of tissue removal system 10, and in certain embodiments, outlet 32 comprises a fluid impermeable membrane (e.g., a membrane that is impermeable to liquid and air). Outlet 32 should be structured to pass the composition in mixing container 30 to a patient under the appropriate conditions. For example, if a syringe is used to withdraw the composition, outlet 32 should be able to accommodate a needle of the syringe without compromising the sterility of the system or composition. In additional embodiments, if the outlet is coupled to a device that is configured to administer the composition, but not to withdraw the composition, such as a cannula that administers the composition by applying positive pressure to displace the composition through the cannula, outlet 32 should be configured to allow the composition contained in mixing container 30 to be passed into the cannula. In other embodiments, outlet 32 may comprise, or be coupled in a closed-system fashion to, the device for administering the composition, such as a needle of a syringe or a cannula for administering the composition by applying positive pressure.

Tissue removal system 10 is also illustrated as including a waste container 36 positioned to collect waste from tissue collection container 12. In the illustrated embodiment, waste container 36 is also coupled and positioned to receive waste from cell collection container 26. A wash container 38 is provided in fluid communication with wash line 39 to deliver a washing fluid, such as saline or any other suitable buffer, via wash port 46 to tissue collection container 12. Tissue collection container 12 also includes an air inlet 40 for controlling the amount of pressure within tissue collection container 12. An additive line 42 is provided on tissue collection container 12 to permit an additive to be added to tissue collection container 12. In reference to the methods disclosed herein, additive line 42 is provided to deliver one or more enzymes to tissue collection container 12 to facilitate the separation of the active cell component from the rest of the adipose tissue contained in filter 16. As illustrated, additive line 42 comprises a needle 44 which can be used to receive the enzyme from a suitable container.

Figure 2:
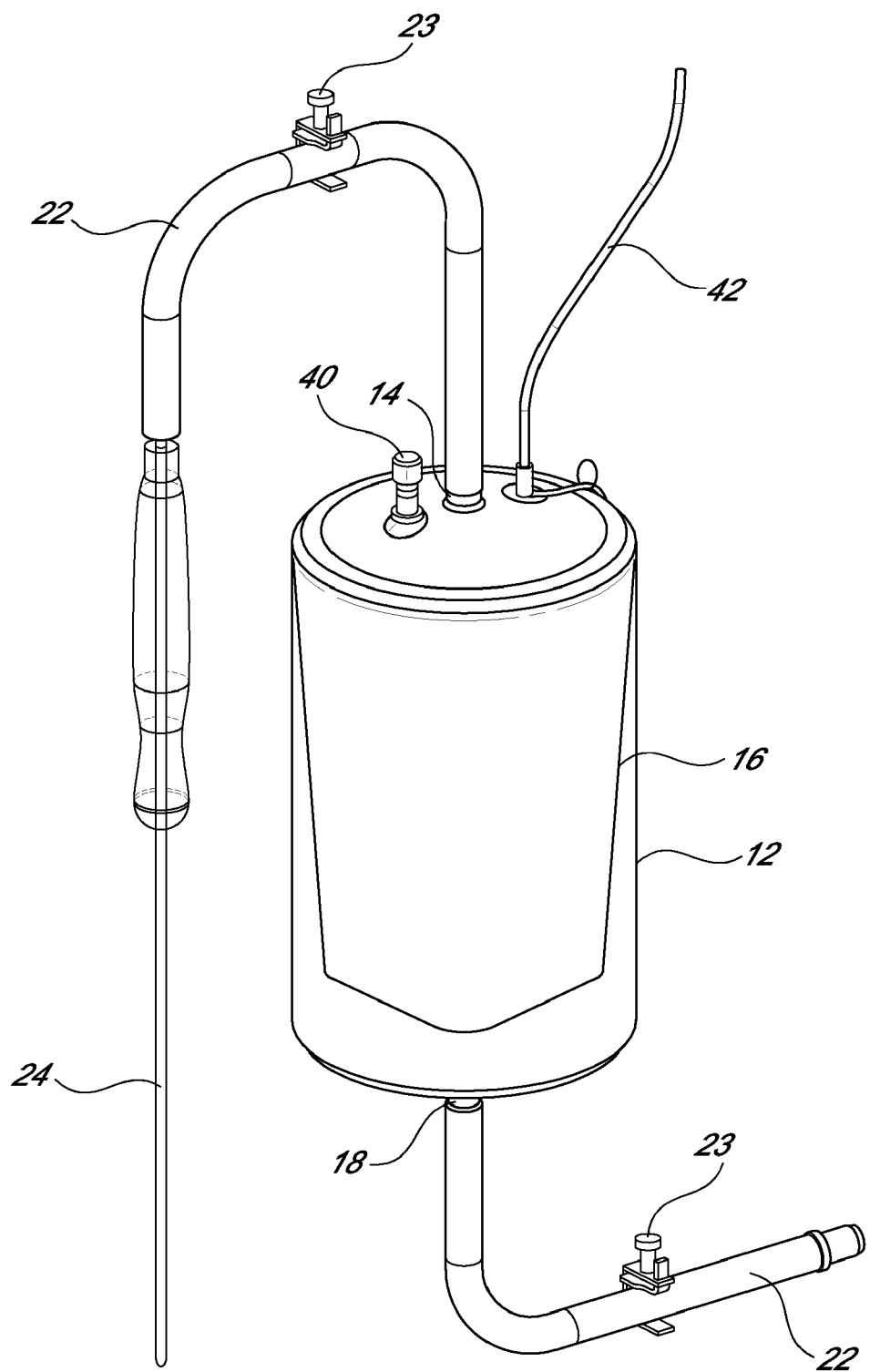
FIG. 2 depicts a tissue collection container of the tissue removal system of FIG. 1.
Figure 3:
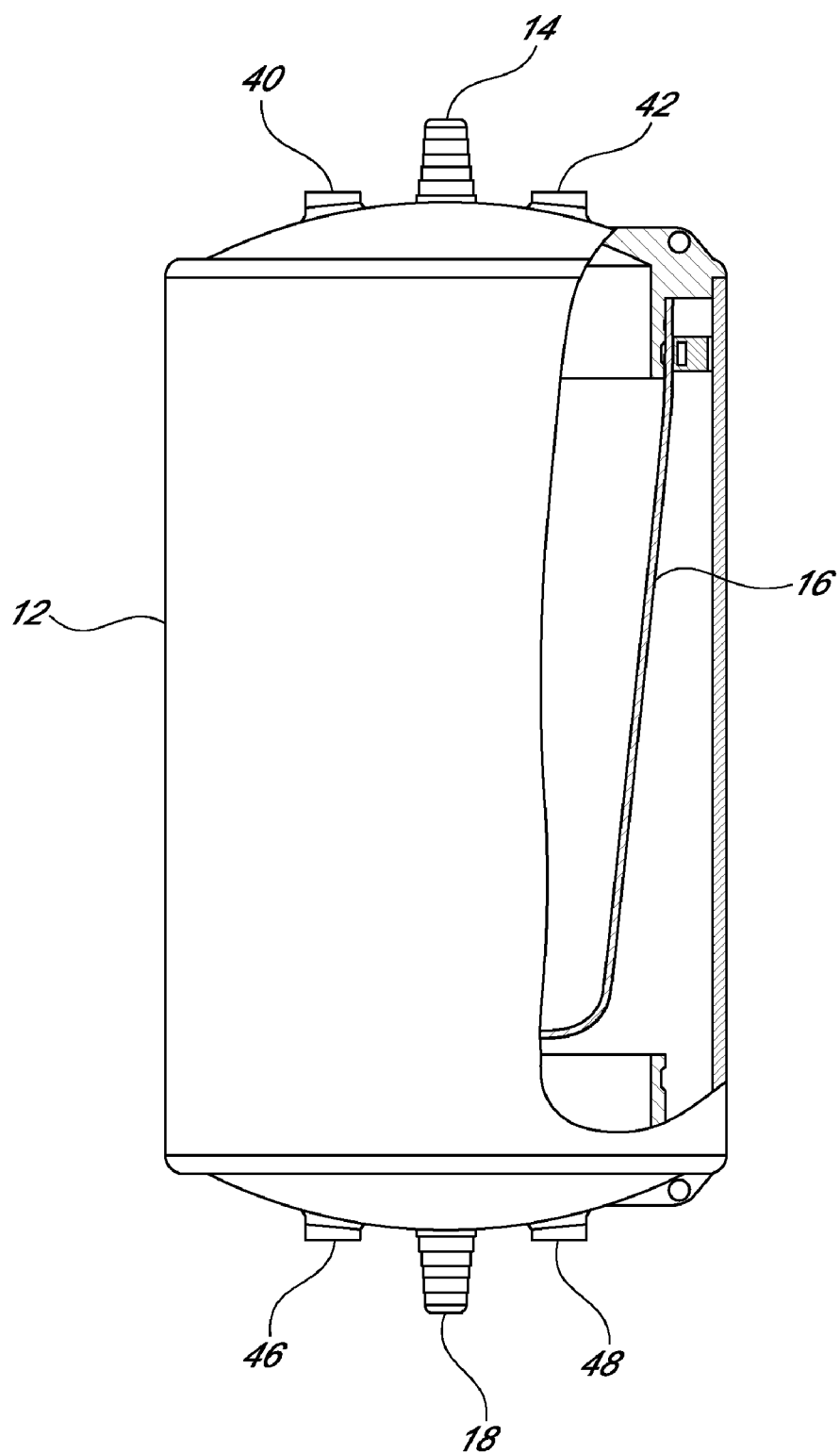
FIG. 3 is a partial cross-sectional view of the tissue collection container of FIG. 2.

A particular embodiment of components of tissue removal system 10 are illustrated in FIGS. 2 and 3 where like numbers represent like parts. In the particular embodiment of FIGS. 2 and 3, tissue collection container 12 includes a body that retains its form when suction is applied to the container. More specifically, tissue collection container 12 includes a rigid body, for example, a body constructed of a medical grade polycarbonate containing a roughly conical filter pocket of medical grade polyester with a mesh size of 275 μm. The rigid tissue collection container may have a size of approximately eight inches high and approximately five inches in diameter; the wall thickness may be about 0.125 inches. The interior of the cylinder is accessed through two ports for suction tubing, two ports with tubing for connection through sterile docking technology, and two ports for needle puncture access through a rubber septum. The same functionality could be achieved with different materials, mesh size, and the number and type of ports. For example, mesh pore sizes smaller than 100 μm or as large as several thousand microns would achieve the same purpose of allowing passage of saline and blood cells while retaining adipose tissue aggregates and fragments. Similarly, the device purpose could be achieved by use of an alternative rigid plastic material, by substitution of the disposable cannula with a non-disposable, multi-use sterile cannula, or by many other modifications that would be known to those skilled in the art. However, in other embodiments of tissue removal system 10, tissue collection container 12 may include a collapsible body, such as a tissue collection bag. In such systems, the bag is preferably provided with a support, such as an internal or external frame, that helps reduce the likelihood that the bag will collapse upon the application of suction to the bag.

In order to reduce contamination within tissue removal system 10, one or more clamps 23 may be provided on the various lines or conduits to control the flow of material through the lines to the various components of the system. Clamps 23 permit a user to effectively seal various regions of tissue removal system 10. In a preferred embodiment, one or more of the components of system 10 are disposable. Avoiding reusing the components in this embodiment helps to reduce contamination that may be associated with repeated use of various components. In addition, providing the components in a disposable set provides an advantage of being able to sterilize all of the components at a single time, which may substantially reduce the time required 10 for practicing the methods disclosed herein. In fully or partially automated embodiments, computer-controlled valves may be implemented in addition to or as an alternative to clamps 23.

In addition, tissue removal system 10 may include additional devices or components that permit, among other things, determination of the volume of material retained in the filter 16, to allow recording of written information regarding the extraction or processing procedure, or perform other supplementary functions such as attaching the device to a stand or bedding during operation.

The components of the tissue removal system 10 should be made of materials that are non-reactive with biological fluids or tissues, and non-reactive with agents used in processing biological fluids and tissues. In addition, the materials from which the various components are made should be capable of withstanding sterilization, such as by autoclaving, and irradiation, including but not limited to beta- or gamma-irradiation. The tubing and the cannula handle may be made of any suitable material, such as polyethylene. The cannula may be made of stainless steel.

In accordance with the invention herein disclosed, the tissue removal system 10 provides a closed system that is convenient for removal, processing, and administration of stem cells found in adipose tissue. The system can be placed near the patient for removal of adipose tissue, and the tissue can be processed without requiring the tissue to be removed from the system. Thus, a system is provided can provide fresh stem cell enhanced compositions to a patient, and reduces potential risks associated with culturing and or preserving stem cells.

Referring to the disclosure herein, a method for extracting tissue from a patient may include the following steps: (i) preparing the patient as for traditional lipoplasty; (ii) removing the cannula and the tissue removal system from the packaging materials to the sterile field; (iii) connecting a liposuction pump (with conventional trap and in-line microbial filters) to the hose adaptor leading from the tissue collection container; (iv) ensuring that the tubing screw clamps are not engaged on the suction ports of the tissue collection container; (v) using the cannula as a regular liposuction cannula to remove unwanted adipose tissue; (vi) applying in a manual operation embodiment two tubing screw clamps to seal the tissue collection container after the desired amount of adipose tissue have been collected with the tissue collection container; and (vii) ensuring that the tissue collection container is properly labeled with a patient identification label, and recording other information on the label (date and time of procedure, etc.) in accordance with institutional practice.

Referring to the illustrated tissue removal system 10, tissue is collected directly into the processing components by attaching the tubing 22 to the suction source 20 with an in-line fluid trap and inserting the cannula 24 into the harvest site. Adipose tissue is then aspirated into the tissue collecting container 12 where it is retained by the filter 16 held within the tissue collection container 12. Following tissue collection the collected adipose tissue can be rinsed with a washing fluid, such as sterile isotonic saline, contained in wash container 38 added to tissue collection container 12 via wash line 39. When the tissue collecting container 12 is made of a rigid material in the illustrated embodiment to support collection under suction, the air displaced from the housing during addition of saline can be vented through the air-inlet port 40. Alternatively the air may be displaced into the waste container 36 or similar holding place. Once the tissue is rinsed the waste material can be allowed to flow into the waste container 36.

In certain embodiments, units of intact adipose tissue may be removed from tissue collection container 12 prior to disaggregating the adipose tissue in collection container 12. The units of intact adipose tissue may be passed along tissue retrieval line 34 so that the units can be delivered to mixing container 30. In these embodiments, the intact tissue can be mixed with the stem cells prior to administration to a patient.

After the tissue has been collected, needle 44 can be inserted into a sterile vial of collagenase-containing enzyme solution which is then passed into tissue collection container 12 where it is mixed with the adipose tissue at or around 37° C. for 30-60 minutes. Washing steps may be repeated as needed and the disaggregated tissue may be washed following elution of the active cell population in order to maximize yield. At the end of tissue disaggregation the tissue collection container 12 is placed upright to allow flotation of the adipocytes. The active cell population is then allowed to flow into cell collection container 26 where the cells are separated from collagenase and residual free lipid. Cells may be washed and/or concentrated by any method known to persons of ordinary skill in the art including but not limited to sequential centrifugation/re-suspension washes or continuous flow mechanisms. The concentrated, washed cells are then allowed to flow into mixing container 30 where they can be mixed with intact tissue from tissue retrieval line 34 and/or any intended additives before being removed through the outlet 32 for administration to a patient. The material contained in cell collecting container 26 may be filtered using cell filter 28 following washing to enhance removal of unwanted residual cell and tissue aggregates that could lead to embolism upon application.

During the processing, one or more additives may be added to the various containers as needed to enhance the results. Some examples of additives include agents that optimize washing and disaggregation, additives that enhance the viability of the active cell population during processing, antimicrobial agents (e.g., antibiotics), additives that lyse adipocytes and/or red blood cells, or additives that enrich for cell populations of interest (by differential adherence to solid phase moieties or to otherwise promote the substantial reduction or enrichment of cell populations).

In the above embodiment, the tissue collecting container 12 is intrinsic to the processing components of the tissue removal system 10. Alternatively a separate tissue collecting container, such as that described in patent application Ser. No. 10/242,094, entitled PRESERVATION OF NON EMBRYONIC CELLS FROM NON HEMATOPOIETIC TISSUES, filed Sep. 12, 2002, which claims the benefit of U.S. Provisional Patent Application No. 60/322,070 filed Sep. 14, 2001, which is commonly assigned, and the contents of which are expressly incorporated herein by reference could be employed in whole or in part with subsequent transference of the disaggregated material to the processing components. Additional potential tissue collecting containers are disclosed in U.S. Pat. Nos. 6,316,247 and 5,372,945.

As indicated above, in certain embodiments of the invention, the methods may be automated by providing one or more additional devices that can automatically perform the steps of the methods. In such embodiments, a processing device (e.g., microprocessor or personal computer) is a device to partially or completely automate the steps described above. Examples of steps amenable to such automation include, but are not limited to, controlling the ingress and egress of fluids and tissues along particular tubing paths by controlling pumps and valves of the system or processing device; detecting blockages with pressure sensors; mixing mechanisms, measuring the amount of tissue and/or fluid to be moved along a particular pathway using volumetric mechanisms; maintaining temperatures of the various components using heat control devices; washing and concentrating the cell, and integrating the process with timing and software mechanisms. In one embodiment, software can control the parameters of the process to allow production of a cell population prepared to specific operator-defined parameters. Thus, the automation device or devices improve the performance of the procedures, and provide automatic harvesting of adipose tissue and processing of the adipose tissue for administration to a patient.

Figure 4:
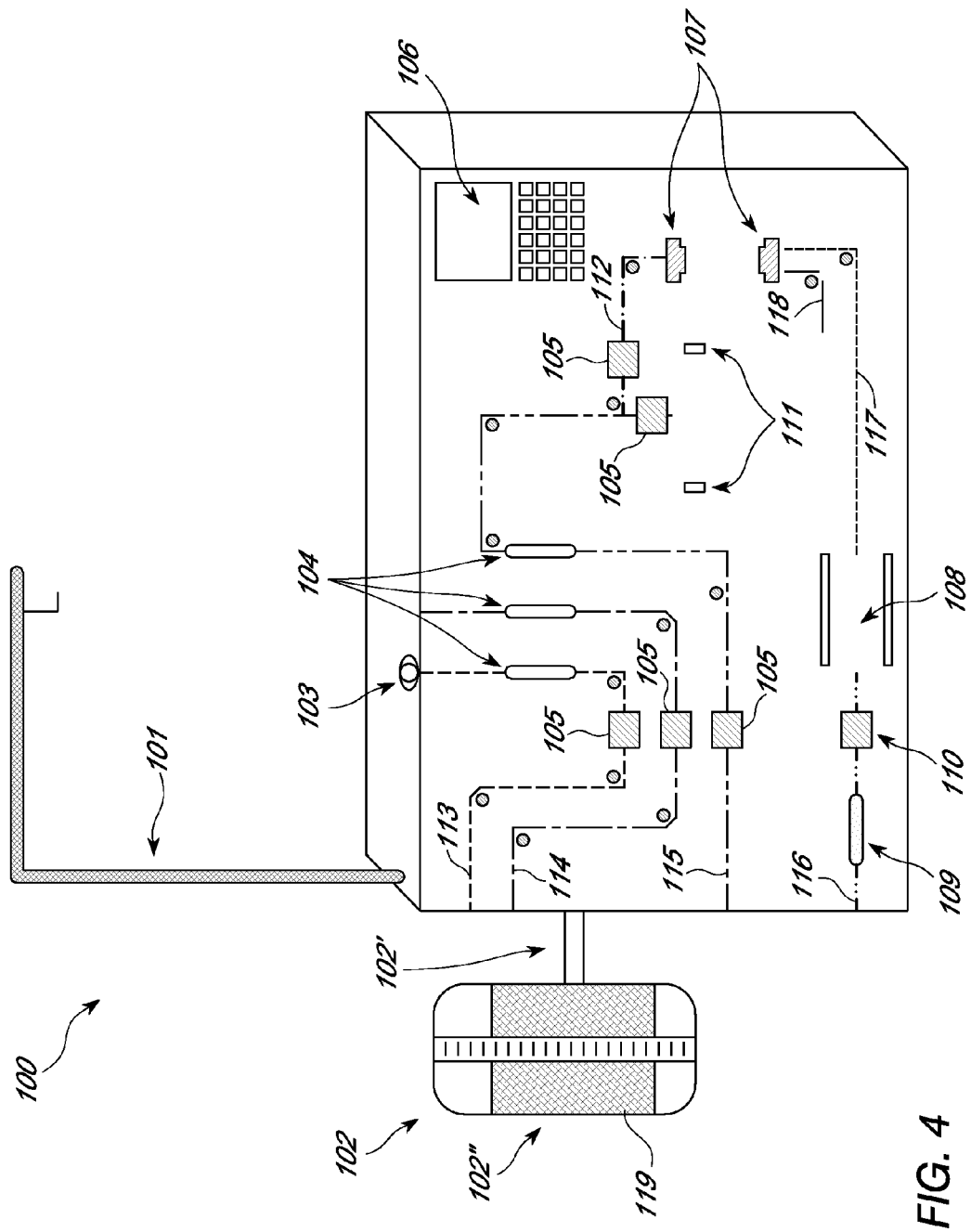
FIG. 4 depicts a processing device for automating the operation of a tissue removal system.

One particular automation device is illustrated in FIG. 4. A tissue removal container (not shown) is placed into a device 100 using color-coded guide marks 112-118 to properly align and insert the tubing into appropriate paths. Device 100 includes a plurality of valves 105 and 110, and a plurality of pumps 104 and 109. Tubing is placed into a series of valves 105, 110 and pumps 104, 109 which are controlled by an integrated microprocessor system to coordinate fluid and tissue flow in accordance with the user defined program. Program selection is mediated through a user interface panel 106. A saline container is placed onto a holding structure 101 and attached to the tissue collection container. A vial or tube of collagenase or other tissue dissociation medium or mixture (not shown) is inserted into the tissue collection container at point 103. A waste bag (not shown) is inserted into a holding structure 111, the cell separation chamber/cell collection container is placed into a holding structure 107, and the tissue/ cell mixing container is placed into the holding structure 108. The tissue collection container is placed into the agitation/incubation chamber 102. Adipose tissue may be collected into the tissue collecting container while the container is in position within the device or prior to placement within the device. The device may contain an optional transparent insert 119 or other device allowing determination of the volume of tissue within the tissue collecting container. Alternatively volume may be determined by measurement of the weight of material contained in the agitation/incubation chamber 102 (corresponding to tissue collecting container 12). This volume may be displayed on the user interface screen 106.

The microprocessor then opens the valves 105 on lines 114 and 115 and activates the pumps 104 on line 114 for introduction of saline into the collection chamber 102 and removal of waste material 115 to the waste bag 111. During this process the collection chamber is agitated by rocking, and is maintained at a programmed temperature by warming devices integrated into the chamber 102. In certain embodiments, tissue processing may use pre-warmed saline in which case the role of the warming device of the agitation/incubation chamber is to maintain temperature at the determined preprogrammed point rather than to increase the temperature. Once the tissue is washed some fraction from 0% to 100% of the intact, washed adipose tissue may be removed from the incubation chamber 102 by activation of the pump 109 and valve 110 on line 116. Material withdrawn at this time is held in the mixing chamber 108.

Dissociation medium 103 is added to material remaining in the chamber 102 by opening the valve 105 on line 113, closing other valves and activating pump 104 on line 113. After addition of dissociation medium the chamber 102 is agitated and maintained at temperature as described above. At the conclusion of the programmed incubation period agitation is halted to allow flotation of adipocytes. Additional saline may be added to facilitate this process. Following flotation of adipocytes, the valves on lines 112 and 115 are opened to allow removal of the target cell population from the chamber 102 into the cell washing chamber 107. Washed cells are removed through line 117 into the mixing chamber 108, supernatant and washing solution are removed into the waste chamber 111 through line 118. Additional saline is passed into the system through line 114 to complete the washing process. Cells are mixed in the chamber 108 with any intact tissue removed through line 116 earlier in processing. Mixing may be achieved by any means known to those skilled in the art including but not limited to agitation rocking/inversion of chamber, or by compression pulsed or by moving rollers. Mixed material may then be removed through the port in the mixing chamber of the disposable set.

The device includes a microprocessor-controlled mechanism for automating the process according to pre-programmed parameters 106. This system would also include use of pressure sensors for detection of blockages and similar safety and quality control mechanisms. In a preferred embodiment the software component of the system would include automated collection of "run data" including, for example, the lot numbers of disposable components, temperature and volume measurements, tissue volume and cell number parameters, dose of enzyme applied, incubation time, operator identity, date and time, patient identity, etc. In a preferred embodiment of the device a bar code reading system would be integrated to permit data entry of these variables (for example disposable set lot number and expiration date, lot number and expiration date of the Collagenase, patient/sample identifiers, etc.) into the device controller as part of documentation of processing. This would reduce the opportunity for data entry errors. This device could be easily incorporated into the controller system using a USB or other interface port and system known to the art. In this way the device would provide integrated control of the data entry and documentation of the process. A print-out report of these parameters would be part of the user-defined parameters of a programmed operation of the device. Naturally this would require integration of a printer component (hardware and driver) or printer driver in software plus an interface output connector for a printer (e.g., a USB port) in the hardware of the device.

In a further embodiment, software incorporated into the controller would prompt users through the steps necessary for proper insertion of tubing and other elements into the device. Software would also initiate automated testing to confirm correct insertion of tubing, absence of blockages, etc.

The general approach to processing in this device would use the same parameters as those described elsewhere in this disclosure for manual cell processing.

Many other conformations of the staged mechanisms used for cell processing will be apparent to one skilled in the art and the present description is included as one example only. For example, mixing of tissue and saline during washing and disaggregation may occur by agitation as in the present example or by fluid recirculation. Cell washing may be mediated by a continuous flow mechanism such as the spinning membrane approach, differential adherence, differential centrifugation (including, but not limited to differential sedimentation, velocity, or gradient separation), or by a combination of means. Similarly, additional components to allow further manipulation of cells including addition of growth factors or other biological response modifiers (Lind, M., Growth factor stimulation of bone healing. Effects on osteoblasts, osteomies, and implants fixation. Acta Orthop Scand Suppl, 1998. 283: p. 2-37; Hanada, K., J. E. Dennis, and A. I. Caplan, Stimulatory effects of basic fibroblast growth factor and bone morphogenetic protein-2 on osteogenic differentiation of rat bone marrow-derived mesenchymal stem cells. J Bone Miner Res, 1997. 12(10): p. 1606-14; Lieberman, J. R., et al., Regional gene therapy with a BMP-2-producing murine stromal cell line induces heterotopic and orthotopic bone formation in rodents. J Orthop Res, 1998. 16(3): p. 330-9), mixing of cells with other structural components (e.g., bone fragments (Jean, J. L., S. J. Wang, and M. K. Au, Treatment of a large segmental bone defect with allograft and autogenous bone marrow graft. J Formos Med Assoc, 1997. 96(7): p. 553-7), collagen (Saadeh, P. B., et al., Repair of a Critical Size Defect in the Rat Mandible Using Allogenic Type I Collagen. J Craniofac Surg, 2001. 12(6): p. 573-579) and/or synthetic components intended for implant with the cells into the recipient (Petite, H., et al., Tissue-engineered bone regeneration. Nat Biotechnol, 2000. 18(9): p. 959-63. taf/dynapage.taf?file=/ncb/biotech/v1-8/n9/full/nbt0900.sub.--959.html taf/dynapage.taf?file=/ncb/biotech/v18/n9-/abs/nbt0900.sub.--959.html; Gao, J., et al., Tissue-Engineered Fabrication of an Osteochondral Composite Graft Using Rat Bone Marrow-Derived Mesenchymal Stem Cells. Tissue Eng, 2001. 7(4): p. 363-71; Ohgushi, H. and A. I. Caplan, Stem cell technology and bioceramics: from cell to gene engineering. J Biomed Mater Res, 1999. 48(6): p. 913-27; Caplan, A. I. and V. M. Goldberg, Principles of tissue engineered regeneration of skeletal tissues. Clin Orthop, 1999 (367 Suppl): p. S12-6). Post-processing manipulation may also include cell culture (Caplan, A. I. and S. P. Bruder, Mesenchymal stem cells: building blocks for molecular medicine in the 21st century. Trends Mol Med, 2001. 7(6): p. 259-64; Petite, supra; Zuk, P. A., et al., Multilineage cells from human adipose tissue: implications for cell-based therapies. Tissue Eng, 2001. 7(2): p. 211-28), gene transfer (Luskey, B. D., et al., Gene transfer into murine hematopoietic stem cells and bone marrow stromal cells. Ann N Y Acad Sci, 1990. 612(398): p. 398-406; Grompe, M., et al., Therapeutic trials in the murine model of hereditary tyrosinaemia type I: a progress report. J Inherit Metab Dis, 1998. 21(5): p. 518-31; Gazit, D., et al., Engineered pluripotent mesenchymal cells integrate and differentiate in regenerating bone: a novel cell-mediated gene therapy. J Gene Med, 1999. 1(2): p. 121-33; Mosca, J. D., et al., Mesenchymal stem cells as vehicles for gene delivery. Clin Orthop, 2000(379 Suppl): p. S71-90), or further cell purification (Greenberg, A. W. and D. A. Hammer, Cell separation mediated by differential rolling adhesion. Biotechnol Bioeng, 2001. 73(2): p. 111-24; Mainwaring, G. and A. F. Rowley, Separation of leucocytes in the dogfish (Scyliorhinus canicula) using density gradient centrifugation and differential adhesion to glass coverslips. Cell Tissue Res, 1985. 241(2): p. 283-90; Schweitzer, C. M., et al., Isolation and culture of human bone marrow endothelial cells. Exp Hematol, 1995. 23(1): p. 41-8). Mechanisms for performance of such functions may be integrated within the device shown in FIG. 4 or may be incorporated in separate devices.

In additional embodiments of the invention, tissue collected into a conventional adipose tissue trap could be transferred into a processing set designed for processing other tissues. For example, BAXTER® Inc. manufacture and sell a series of plastic bags and filters intended for use in the setting of a bone marrow transplant harvest ("Bone Marrow Collection Kit with Flexible Pre-Filters and Inline Filters", Product Code, 4R2107, U.S. Pat. Nos. 4,346,703 and 5,724,988). This bag set contains a large conical bag with an integrated 800 μm filter which could be used for washing the collected adipose tissue. In this example adipose tissue fragments larger than 800 μm would be retained in the bag. These fragments could then be washed by repeated addition of saline (or other washing solution) followed by removal of waste material through ports below the filter. Mixing could be achieved manually or by use of a benchtop rocking device and warming could be applied by use of a heating pad. Disaggregation could occur within the lumen of this bag. Following disaggregation cells would pass through the integrated 800 μm filter (and optionally through one or more filters of smaller mesh size provided with the kit) and collected into a collection bag (also provided). This bag could then be placed into a centrifuge (e.g., a Sorval RC-3C) where cells could be serially washed and concentrated. Cells could also be washed using existing cell washing devices (largely developed for washing human blood products) such as those sold by BAXTER® Inc (CYTOMATE® or BAXTER® CS3000) or by Cobe Inc. (COBE SPECTRA™). The disposable elements may be integrated using the fittings provided by the manufacturer or they may be linked by use of a sterile connecting device such as those manufactured by TERUMO™ Inc. Similarly the mechanisms described in this less integrated approach could be linked to a central controller and assembled as components of a more integrated device. A peristaltic pump or battery of pumps could be used to automate fluid flow with use of manual or automated clamping to open and close fluid pathways.

In a preferred embodiment of the invention, the tissue removal system and processing set would be present in the vicinity of the patient receiving the treatment, such as the operating room or out-patient procedure room (effectively at the patient's bedside). This allows rapid, efficient tissue harvest and processing, remove the opportunity for specimen handling/labeling error and thereby allow for performance of the entire process in the course of a single surgical procedure.

The following examples are provided to demonstrate particular situations and settings in which this technology may be applied and are not intended to restrict the scope of the invention and the claims included in this disclosure

EXAMPLE 1

Autologous Fat Transfer

Autologous fat transfer is a relatively common cosmetic and structural procedure involving the harvest of adipose tissue (fat) from one location and reimplantation in another location within the same individual (Coleman, S. R. (1995). "Long-term survival of fat transplants: controlled demonstrations." Aesthetic Plast Surg 19(5): 421-5; Coleman, S. R. (2001). "Structural fat grafts: the ideal filler?" Clin Plast Surg 28(1): 111-9; Coleman, W. P., 3rd (1991). "Autologous fat transplantation." Plast Reconstr Surg 88(4): 736.). However, as indicated above, this procedure is frequently compromised by inconsistent engraftment such that the implanted material is fully or partially resorbed or is replaced by scar tissue (Eremia, S. and N. Newman (2000). "Long-term follow-up after autologous fat grafting: analysis of results from 116 patients followed at least 12 months after receiving the last of a minimum of two treatments." Dermatol Surg 26(12): 1150-8). At least part of the loss of function can be attributed to necrosis of implanted fat tissue during the time it takes for new blood vessels to form and feed the implant. Thus tissue implanted into highly vascular areas such as muscle beds shows better engraftment than when implanted into less well perfused tissues (Guerrerosantos, J., A. Gonzalez-Mendoza, et al. (1996). "Long-term survival of free fat grafts in muscle: an experimental study in rats." Aesthetic Plast Surg 20(5): 403-8).

Processed lipoaspirate prepared as described in this disclosure addresses this issue by supplementing the implant with additional endothelial precursors and stem cells. Extracted adipose tissue fragments from inbred Wistar rats were mixed with processed lipoaspirate in accordance with the methods disclosed herein. This composition was then implanted subcutaneously into the thigh and under the scalp of recipient rats. As controls an equal number of animals received adipose tissue alone (no processed lipoaspirate) under the scalp while animals receiving an implant in the thigh had the contralateral thigh implanted with adipose tissue alone. Grafts were harvested one month post-implantation.

Figure 5:
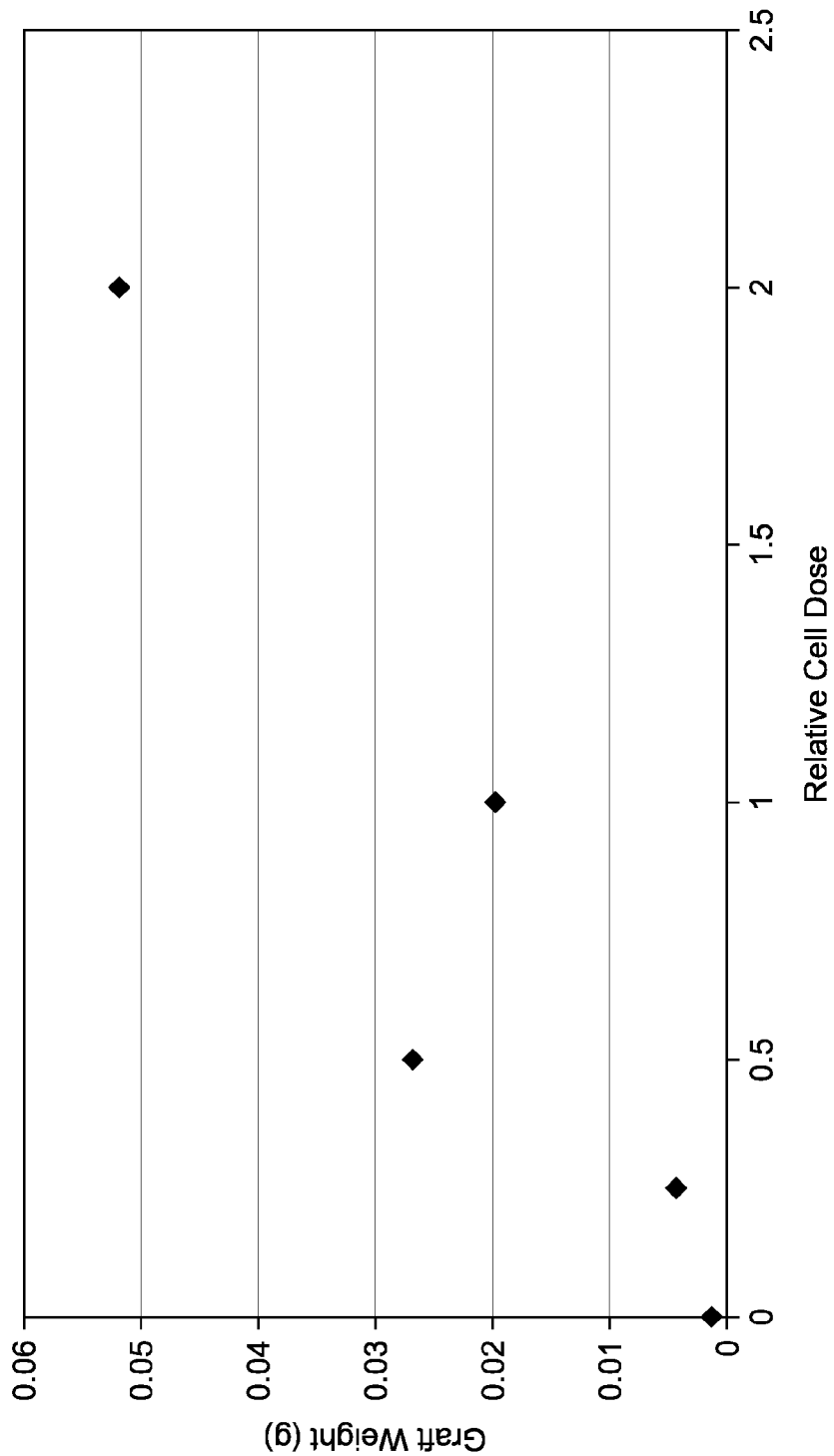
FIG. 5 is a graph depicting graft weight versus cell dose.

The results (FIG. 5) show a trend of increasing graft weight of thigh implants with increasing dose of processed lipoaspirate. Histologic examination of the implants showed improved vascularity of grafts supplemented with processed lipoaspirate. A similar correlation was observed with scalp implants albeit with lower overall retention due to the low vascularity of the dorsal skull in these rats.

In a clinical application of this technology, processed lipoaspirate derived according to this disclosure is prepared and mixed with intact (non-disaggregated) adipose tissue fragments, as disclosed above. The composition comprising the mixture of adipose tissue and the stem cells may be implanted into the recipient to provide an autologous soft tissue filler for correction of contour defects (wrinkles, "divots," pockmarks, and larger deficits) (Coleman, S. R. (2001). "Structural fat grafts: the ideal filler?" Clin Plast Surg 28(1): 111-9) or for providing support to damaged structures such as the urethra (Palma, P. C., C. L. Riccetto, et al. (1997). "Repeated lipoinjections for stress urinary incontinence." J Endourol 11(1): 67-70; Lee, P. E., R. C. Kung, et al. (2001). "Periurethral autologous fat injection as treatment for female stress urinary incontinence: a randomized double-blind controlled trial." J Urol 165(1): 153-8).

EXAMPLE 2

Acute Liver Injury

Figure 6:
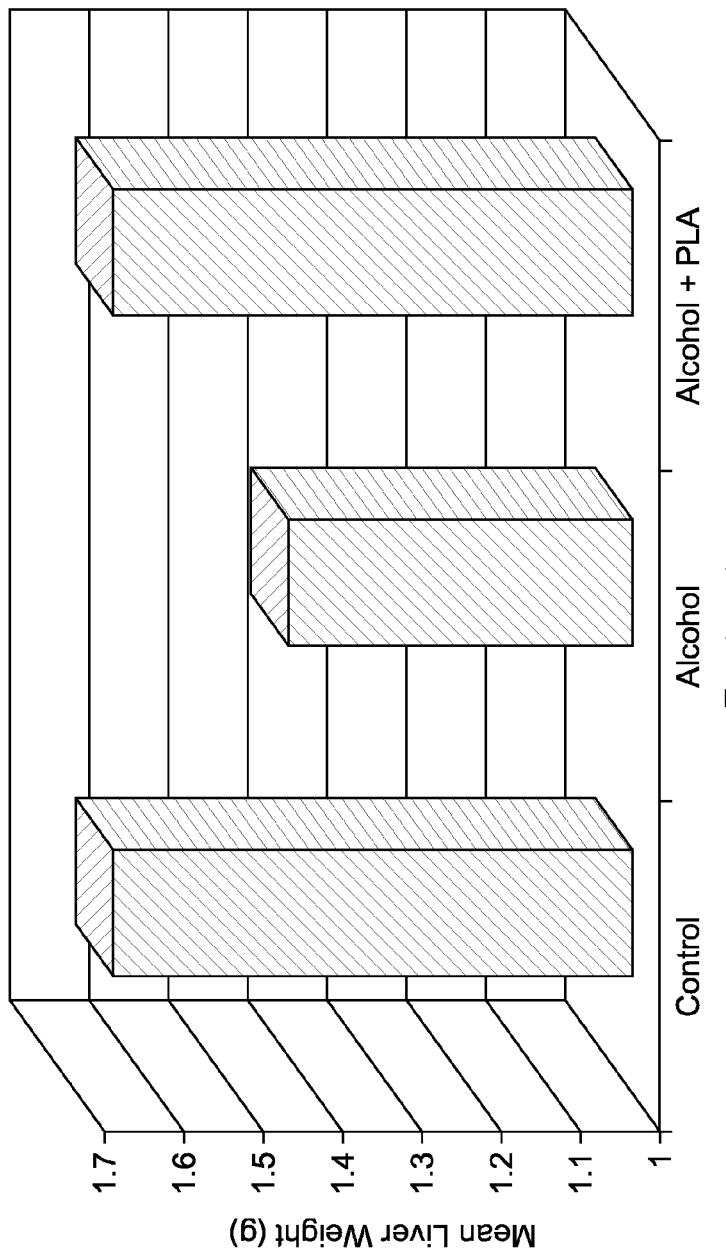
FIG. 6 is a graph depicting the effects of processed lipoaspirate on alcohol treated mice
Figure 7:
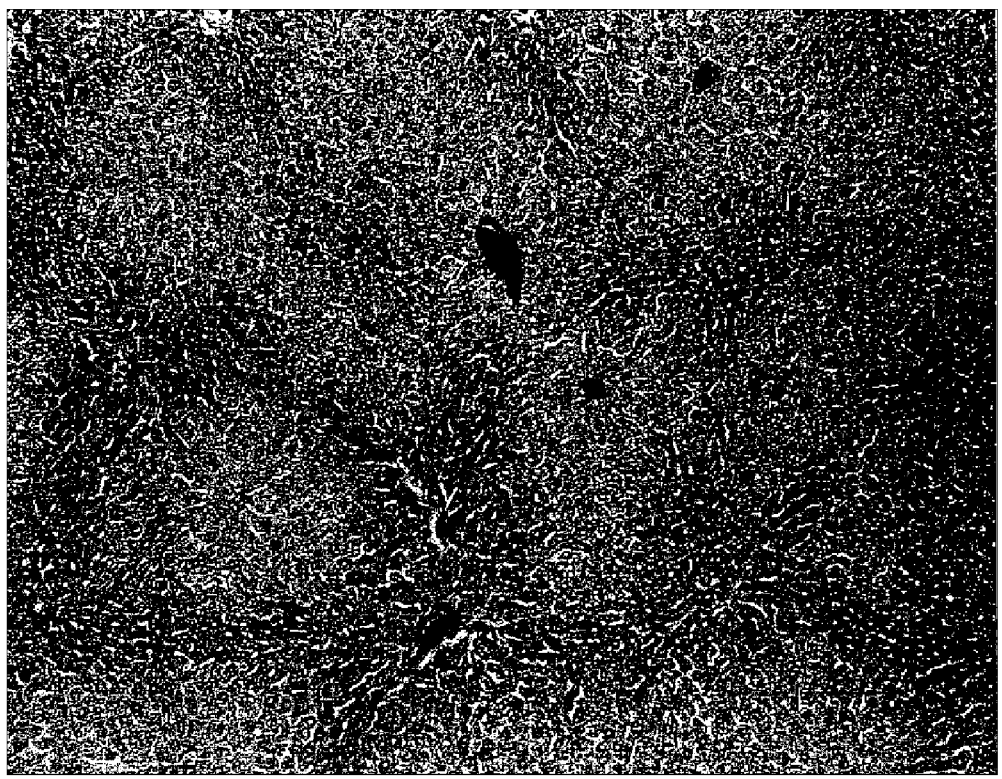
FIG. 7 is a photomicrograph of liver tissue of an alcohol treated mouse that received processed lipoaspirate

Liver damage induced by intraperitoneal injection with allyl alcohol is a common model of periportal acute liver injury (Lee, J. H., Z. Ilic, et al. (1996). "Cell kinetics of repair after allyl alcohol-induced liver necrosis in mice." Int J Exp Pathol 77(2): 63-72; Werlich, T., K. J. Stiller, et al. (1999). "Experimental studies on the stem cell concept of liver regeneration. II." Exp Toxicol Pathol 51(1): 93-8.; Yin, L., D. Lynch, et al. (1999). "Participation of different cell types in the restitutive response of the rat liver to periportal injury induced by allyl alcohol." J Hepatol 31(3): 497-507). This model has been used to demonstrate the presence of a population of stem cells that is critical to liver regeneration (Yavorkovsky, L., E. Lai, et al. (1995). "Participation of small intraportal stem cells in the restitutive response of the liver to periportal necrosis induced by allyl alcohol." Hepatology 21(6): 1702-12; Werlich, T., K. J. Stiller, et al. (1999). "Experimental studies on the stem cell concept of liver regeneration. II." Exp Toxicol Pathol 51(1): 93-8). We modified this model in Swiss Webster mice in which alcohol-induced injury was followed by injection of processed lipoaspirate. Animals were sacrificed at one week and the livers were removed, weighed, and prepared for histologic examination. The results (FIGS. 6 and 7) show substantially improved liver weight in those animals receiving processed lipoaspirate. Histologic analysis showed normal histology within the treated animals with no evidence of leukocyte infiltrate or any other mechanism that might aberrantly increase liver weight.

In a clinical setting, a patient with liver damage would have adipose tissue extracted and processed according to this disclosure. Processed lipoaspirate could then be injected intravenously for systemic delivery or targeted to the liver through the hepatic circulatory system.

EXAMPLE 3

Acute Heart Damage

Acute myocardial infarct (heart attack) results in ischemic injury to the myocardium. Tissue damage can be minimized by reperfusion of the damaged tissue and by regeneration of myocardial tissue (Murry, C. E., R. W. Wiseman, et al. (1996). "Skeletal myoblast transplantation for repair of myocardial necrosis." J Clin Invest 98(11): 2512-23; Orlic, D., J. Kajstura, et al. (2001). "Bone marrow cells regenerate infarcted myocardium." Nature 410(6829): 701-5; Rajnoch, C., J. C. Chachques, et al. (2001). "Cellular therapy reverses myocardial dysfunction." J Thorac Cardiovasc Surg 121(5): 871-8; Strauer, B. E., M. Brehm, et al. (2002). "Repair of infarcted myocardium by autologous intracoronary mononuclear bone marrow cell transplantation in humans." Circulation 106(15): 1913-8). The bedside approach described in this disclosure would provide a potentially superior source of regenerative cells in that cells could be provided in greater numbers and purity without the morbidity associated with a marrow harvest.

EXAMPLE 4

Allogeneic Application for Inherited Disease

Horwitz et al have demonstrated that stem cells from bone marrow can provide clinical benefit to patients with a non-hematopoietic disorder, specifically Osteogenesis imperfecta (Horwitz, E. M., D. J. Prockop, et al. (1999). "Transplantability and therapeutic effects of bone marrow-derived mesenchymal cells in children with osteogenesis imperfecta." Nat Med 5(3): 309-13; Horwitz, E. M., D. J. Prockop, et al. (2001). "Clinical responses to bone marrow transplantation in children with severe osteogenesis imperfecta." Blood 97(5): 1227-31). In these studies the authors attempted to compensate for the low number and frequency of non-hematopoietic stem cells in marrow by growing cells in culture to expand and purify the MSC component. However, as mentioned above, growing cells in culture is associated with substantial technical and clinical concerns and the potential of adipose tissue, processed in accordance with this disclosure, to provide a source a large number of stem cells without requiring cell culture represents a potential substantive improvement in patient care. In this model a suitably matched donor unaffected by the genetic disease (normal genotype or asymptomatic carrier), preferably a sibling or other first degree relative, would be the source of donor cells although use of unrelated donors is within the scope of this invention. Cells would be extracted from the adipose tissue for infusion into a patient with an inherited disease resulting in compromised tissue function or regeneration. Examples include, but are not limited to Osteogenesis imperfecta, Duschenes Muscular Dystrophy (and other Muscular Dystrophies), inherited retinal degenerative diseases, hereditary tyrosinemia, and numerous other inherited diseases.

A corollary of this is that application of gene therapy approaches in which autologous (self) processed lipoaspirate is modified by insertion of a gene into the stem cell compartment would obviate the need for an allogeneic (no-self) donor. Such an approach could also be used in the treatment of infectious disease in which a novel gene is inserted into the stem cells. For example an antisense or ribozyme construct could be used to generate cells capable of providing an anti-HIV effect. This approach could also be used to generate stem cells capable of acting as drug delivery vehicles.

REFERENCES

Avital, I., D. Inderbitzin, et al. (2001). "Isolation, characterization, and transplantation of bone marrow-derived hepatocyte stem cells." Biochem Biophys Res Commun 288(1): 156-64.

Carmeliet, P. and A. Luttun (2001). "The emerging role of the bone marrow-derived stem cells in (therapeutic) angiogenesis." Thromb Haemost 86(1): 289-97.

Castro-Malaspina, H., W. Ebell, et al. (1984). "Human bone marrow fibroblast colony-forming units (CFU-F)." Prog Clin Biol Res 154: 209-36.

Coleman, S. R. (1995). "Long-term survival of fat transplants: controlled demonstrations." Aesthetic Plast Surg 19(5): 421-5.

Coleman, S. R. (2001). "Structural fat grafts: the ideal filler?" Clin Plast Surg 28(1): 111-9.

Coleman, W. P., 3rd (1991). "Autologous fat transplantation." Plast Reconstr Surg 88(4): 736.

Connolly, J. F. (1998). "Clinical use of marrow osteoprogenitor cells to stimulate osteogenesis." Clin Orthop(355 Suppl): S257-66.

Eremia, S. and N. Newman (2000). "Long-term follow-up after autologous fat grafting: analysis of results from 116 patients followed at least 12 months after receiving the last of a minimum of two treatments." Dermatol Surg 26(12): 1150-8.

Fukuda, K. (2001). "Development of regenerative cardiomyocytes from mesenchymal stem cells for cardiovascular tissue engineering." Artif Organs 25(3): 187-93.

Guerrerosantos, J., A. Gonzalez-Mendoza, et al. (1996). "Long-term survival of free fat grafts in muscle: an experimental study in rats." Aesthetic Plast Surg 20(5): 403-8.

Horwitz, E. M., D. J. Prockop, et al. (1999). "Transplantability and therapeutic effects of bone marrow-derived mesenchymal cells in children with osteogenesis imperfecta." Nat Med 5(3): 309-13.

Horwitz, E. M., D. J. Prockop, et al. (2001). "Clinical responses to bone marrow transplantation in children with severe osteogenesis imperfecta." Blood 97(5): 1227-31.

Huang, J. I., S. R. Beanes, et al. (2002). "Rat extramedullary adipose tissue as a source of osteochondrogenic progenitor cells." Plast Reconstr Surg 109(3): 1033-41; discussion 1042-3.

Hutley, L. J., A. C. Herington, et al. (2001). "Human adipose tissue endothelial cells promote preadipocyte proliferation." Am J Physiol Endocrinol Metab 281(5): El 037-44.

Kern, P. A., A. Knedler, et al. (1983). "Isolation and culture of microvascular endothelium from human adipose tissue." J Clin Invest 71(6): 1822-9.

Lee, J. H., Z. Ilic, et al. (1996). "Cell kinetics of repair after allyl alcohol-induced liver necrosis in mice." Int J Exp Pathol 77(2): 63-72.

Lee, P. E., R. C. Kung, et al. (2001). "Periurethral autologous fat injection as treatment for female stress urinary incontinence: a randomized double-blind controlled trial." J Urol 165(1): 153-8.

Mizuno, H., P. A. Zuk, et al. (2002). "Myogenic differentiation by human processed lipoaspirate cells." Plast Reconstr Surg 109(1): 199-209; discussion 210-1.

Murayama, T., O. M. Tepper, et al. (2002). "Determination of bone marrow-derived endothelial progenitor cell significance in angiogenic growth factor-induced neovascularization in vivo." Exp Hematol 30(8): 967-72.

Murry, C. E., R. W. Wiseman, et al. (1996). "Skeletal myoblast transplantation for repair of myocardial necrosis." J Clin Invest 98(11): 2512-23.

Muschler, G. F., H. Nitto, et al. (2001). "Age- and gender-related changes in the cellularity of human bone marrow and the prevalence of osteoblastic progenitors." J Orthop Res 19(1): 117-25.

Nishimori, M., Y. Yamada, et al. (2002). "Health-related quality of life of unrelated bone marrow donors in Japan." Blood 99(6): 1995-2001.

Orlic, D., J. Kajstura, et al. (2001). "Transplanted adult bone marrow cells repair myocardial infarcts in mice." Ann N Y Acad Sci 938: 221-9; discussion 229-30.

Orlic, D., J. Kajstura, et al. (2001). "Bone marrow cells regenerate infarcted myocardium." Nature 410(6829): 701-5.

Palma, P. C., C. L. Riccetto, et al. (1997). "Repeated lipoinjections for stress urinary incontinence." J Endourol 11(1): 67-70.

Pittenger, M. F., A. M. Mackay, et al. (1999). "Multilineage potential of adult human mesenchymal stem cells." Science 284(5411): 143-7.

Prockop, D. J., S. A. Azizi, et al. (2000). "Potential use of marrow stromal cells as therapeutic vectors for diseases of the central nervous system." Prog Brain Res 128: 293-7.

Rajnoch, C., J. C. Chachques, et al. (2001). "Cellular therapy reverses myocardial dysfunction." J Thorac Cardiovasc Surg 121(5): 871-8.

Shi, Q., S. Rafii, et al. (1998). "Evidence for circulating bone marrow-derived endothelial cells." Blood 92(2): 362-7.

Strauer, B. E., M. Brehm, et al. (2002). "Repair of infarcted myocardium by autologous intracoronary mononuclear bone marrow cell transplantation in humans." Circulation 106(15): 1913-8.

Takahashi, T., C. Kalka, et al. (1999). "Ischemia- and cytokine-induced mobilization of bone marrow-derived endothelial progenitor cells for neovascularization." Nat Med 5(4): 434-8.

Thomas, E. D. (1994). "Stem Cell Transplantation: Past, Present and Future." Stem Cells 12: 539-544.

Werlich, T., K. J. Stiller, et al. (1999). "Experimental studies on the stem cell concept of liver regeneration. II." Exp Toxicol Pathol 51(1): 93-8.

Yavorkovsky, L., E. Lai, et al. (1995). "Participation of small intraportal stem cells in the restitutive response of the liver to periportal necrosis induced by allyl alcohol." Hepatology 21(6): 1702-12.

Yin, L., D. Lynch, et al. (1999). "Participation of different cell types in the restitutive response of the rat liver to periportal injury induced by allyl alcohol." J Hepatol 31(3): 497-507.

Zuk, P. A., M. Zhu, et al. (2001). "Multilineage cells from human adipose tissue: implications for cell-based therapies." Tissue Eng 7(2): 211-28.

Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages or features will be embodied in any particular embodiment of the present invention. Additional advantages and aspects of the present invention are apparent in the following detailed description and claims.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

A number of publications and patents have been cited hereinabove. Each of the cited publications and patents are hereby incorporated by reference in their entireties.

What is claimed is:

1. A method of making an enhanced, autologous fat graft comprising extracting from a subject a first portion of adipose tissue to be used as a fat graft then supplementing said fat graft with a population of concentrated, disaggregated, adipose-derived stem cells and endothelial precursor cells in a buffered solution, wherein said stem cells and endothelial precursor cells are prepared by disaggregating and concentrating the stem cells and endothelial precursor cells from a second portion of extracted adipose tissue from said subject, so as to make said enhanced, autologous fat graft.

2. The method of claim 1, wherein said disaggregated adipose-derived stem cells and endothelial precursor cells are prepared by:
   (a) disaggregating said second portion of extracted adipose tissue to generate a cell suspension; and (b) separating a population of adipose-derived cells that comprises stem cells and endothelial precursor cells from the cell suspension by buoyant density sedimentation, filtration, or centrifugation.

3. The method of claim 2, wherein the second portion of extracted adipose tissue is disaggregated in (a) by enzymatic digestion or mechanical force.

4. The method of claim 2, further comprising reducing the presence of mature adipocytes in the cell suspension generated at step (a) prior to step (b).

5. The method of claim 2, wherein the population of adipose-derived cells that comprises stem cells and endothelial precursor cells in (b) is separated by centrifugation.

6. The method of claim 2, wherein the second portion of extracted adipose tissue is disaggregated in (a) by enzymatic digestion.

7. The method of claim 2, wherein said population of concentrated, disaggregated, adipose-derived stem cells and endothelial precursor cells is prepared in a device that operates in a closed system.

8. The method of claim 1, wherein said first portion of extracted adipose tissue is supplemented with said population of concentrated, disaggregated adipose-derived stem cells and endothelial precursor cells in a device that operates in a closed system.

9. The method of claim 1, wherein said population of concentrated, disaggregated adipose-derived stem cells and endothelial precursor cells is not cultured.

10. A method of making an enhanced, autologous fat graft comprising:
(a) disaggregating a first portion of extracted adipose tissue from a subject with an enzyme or mechanical force to generate a cell suspension;
(b) concentrating the cells in said cell suspension by buoyant density sedimentation, filtration or centrifugation to obtain a population of concentrated, disaggregated adipose-derived stem cells and endothelial precursor cells in a buffered solution; and
(c) supplementing a second portion of extracted adipose tissue to be used as a fat graft from said subject with the population of concentrated, disaggregated adipose-derived stem cells and endothelial precursor cells in the buffered solution, so as to make said enhanced, autologous fat graft.

11. The method of claim 10, wherein the population of concentrated, disaggregated adipose-derived stem cells and endothelial precursor cells in (b) is prepared by centrifugation.

12. The method of claim 10, wherein said population of concentrated, disaggregated adipose-derived stem cells and endothelial precursor cells is prepared in a device that operates in a closed system.

13. The method of claim 10, wherein said second portion of extracted adipose tissue is supplemented with said population of concentrated, disaggregated adipose-derived stem cells and endothelial precursor cells in a device that operates in a closed system.

14. The method of claim 10, further comprising reducing the presence of mature adipocytes in the cell suspension generated at step (a) prior to step (b).

15. The method of claim 10, wherein said population of concentrated, disaggregated adipose-derived stem cells and endothelial precursor cells is not cultured.

16. A method of making an enhanced, autologous fat graft comprising extracting from a subject a first portion of adipose tissue to be used as a fat graft then supplementing said fat graft with a population of concentrated, disaggregated adipose-derived stem cells in a buffered solution, wherein said stem cells are prepared by disaggregating and concentrating the stem cells from a second portion of extracted adipose tissue from said subject, so as to make said enhanced, autologous fat graft.

17. The method of claim 16, wherein said population of concentrated, disaggregated adipose-derived stem cells is not cultured.

18. The method of claim 16, wherein said population of concentrated, disaggregated adipose-derived stem cells is prepared in a device that operates in a closed system.

19. The method of claim 16, wherein said second portion of extracted adipose tissue is supplemented with said population of concentrated, disaggregated stem cells in a device that operates in a closed system.

20. The method of claim 1, wherein the enhanced, autologous fat graft further comprises an additive.

21. The method of claim 10, wherein the enhanced, autologous fat graft further comprises an additive.

22. The method of claim 16, wherein the enhanced, autologous fat graft further comprises an additive.

* * * * *